US009737246B2

(12) United States Patent
Kato

(10) Patent No.: US 9,737,246 B2
(45) Date of Patent: Aug. 22, 2017

(54) APPARATUS AND PROGRAM FOR EVALUATING BIOLOGICAL FUNCTION

(71) Applicant: Toshinori Kato, Tokyo (JP)

(72) Inventor: Toshinori Kato, Tokyo (JP)

(*) Notice: Subject to any disclaimer, the term of this patent is extended or adjusted under 35 U.S.C. 154(b) by 973 days.

(21) Appl. No.: 13/688,715

(22) Filed: Nov. 29, 2012

(65) Prior Publication Data
US 2013/0150687 A1 Jun. 13, 2013

Related U.S. Application Data

(63) Continuation of application No. PCT/JP2011/062466, filed on Nov. 2, 2011.

(30) Foreign Application Priority Data

May 31, 2010 (JP) .................... 2010-125412

(51) Int. Cl.
*A61B 5/1455* (2006.01)
*G01N 21/359* (2014.01)
(Continued)

(52) U.S. Cl.
CPC ........ *A61B 5/14552* (2013.01); *A61B 5/0042* (2013.01); *A61B 5/0205* (2013.01); *A61B 5/14535* (2013.01); *A61B 5/14546* (2013.01); *A61B 5/14551* (2013.01); *A61B 5/4064* (2013.01); *A61B 5/4519* (2013.01); *A61B 5/7225* (2013.01); *A61B 5/7278* (2013.01);
(Continued)

(58) Field of Classification Search
CPC .............. A61B 5/1455; A61B 5/14551; A61B 5/14552; A61B 5/72
See application file for complete search history.

(56) References Cited

U.S. PATENT DOCUMENTS 5,954,053 A * 9/1999 Chance .............. A61B 5/14553
600/310
6,149,618 A 11/2000 Sato
(Continued)

FOREIGN PATENT DOCUMENTS

JP 2670421 B2 10/1997
WO 2006009178 A1 1/2006

*Primary Examiner* — Eric Winakur
(74) *Attorney, Agent, or Firm* — Amin, Turocy & Watson, LLP

(57) ABSTRACT

An apparatus and a program are provided which are capable of simultaneously measuring, evaluating, imaging and displaying the biological function of sites with different biological functions, such as the brain and the muscle, different parts of the brain or different muscle locations, using near-infrared spectroscopy. In an apparatus for evaluating biological function K, physiological indices, including parameters derived from changes in deoxyhemoglobin concentration and changes in oxyhemoglobin concentration, are calculated by a calculating part of a controller. To measure simultaneously, evaluate, image and display the biological functions of sites with different biological function, such as the brain and the muscle, different parts of the brain or different muscle locations, these physiological indices from different sites of the living body are adjusted in such a way that they can be compared with each other by the calculating part and displayed by a display part.

35 Claims, 66 Drawing Sheets

(51) Int. Cl.
*A61B 5/00* (2006.01)
*A61B 5/0205* (2006.01)
*A61B 5/145* (2006.01)
*A61B 10/00* (2006.01)
*G01N 21/31* (2006.01)

(52) U.S. Cl.
CPC ........... A61B 5/743 (2013.01); G01N 21/359 (2013.01); *A61B 10/0045* (2013.01); *G01N 2021/3144* (2013.01)

(56) References Cited

U.S. PATENT DOCUMENTS

| | | | | |
|---|---|---|---|---|
| 7,725,145 | B2* | 5/2010 | Kawasaki | A61B 5/14546 600/336 |
| 2008/0262327 | A1 | 10/2008 | Kato | |
| 2011/0105912 | A1* | 5/2011 | Widman | A61B 5/14553 600/483 |
| 2012/0065485 | A1* | 3/2012 | Benni | A61B 5/14551 600/323 |

* cited by examiner (A) Change in oxygen exchange at rest (B) Change in blood volume at rest Ratio of ΔBV and ΔOE standard deviations: $SD_{OE}/SD_{BV} = 8.1$ Ratio of ΔBV and ΔOE standard deviations: $SD_{OE}/SD_{BV} = 1.2$ (A) Area surrounding the motor area
(B) Motor area

APPARATUS AND PROGRAM FOR EVALUATING BIOLOGICAL FUNCTION

CROSS-REFERENCE TO RELATED APPLICATIONS

The present patent application is a continuation of International application No. PCT/JP2011/062466, filed May 31, 2011, published in Japanese, which is based on, and claims priority from, Japanese Patent Application No. 2010-125412, filed May 31, 2010, both of which are incorporated herein by reference in their entireties.

TECHNICAL FIELD

The present invention relates an apparatus and a program for evaluating biological function; in particular, it relates an apparatus and a program for evaluating biological function used for the purpose of simultaneously measuring, evaluating, imaging and displaying the biological functions of a plurality of sites with different biological functions, such as the brain and the muscle, different parts of the brain, different muscle locations, and the like.

BACKGROUND ART

In recent years, various apparatus have been proposed for measuring and evaluating biological function of sites of the brain, the muscles and the like.

For example, electroencephalography and magnetoencephalography are known as methods for measuring electrical activity of the brain. PET (positron CT), fMRI (functional magnetic resonance imaging), and NIRS (near-infrared spectroscopy) are known as methods utilizing cerebral blood flow, oxygen metabolism and the like.

In addition, if fMRI, PET and the like are used, $CMRO_2$ (cerebral metabolic rate of oxygen), CBF (cerebral blood flow), CBV (cerebral blood volume), and OEF (oxygen extraction fraction) can be measured simultaneously; and if NIRS is used, changes in oxyhemoglobin and deoxyhemoglobin can be measured simultaneously in real time.

In addition, a technique has been proposed wherein, by means of an apparatus for evaluating biological function invented and applied for by the present inventor and applicant (see Patent Reference 1), the extent of an exercise load is evaluated from changes in phase, using two-dimensional diagrams created based on amounts of change in concentration of oxyhemoglobin and deoxyhemoglobin in the brain, measured by means of a NIRS apparatus.

NIRS apparatus are also used for measuring muscle oxygen metabolism (referred to below as Previous Example 1).

In addition, electromyography is known as a method for measuring electrical activity of the muscle (referred to below as Previous Example 2).

In addition, as an example of a muscle training methods, a muscle training method is proposed in Patent Reference 2 that is a muscle training method intended to increase muscle size by wrapping a binding device for applying a constricting force to a muscle around a given muscle site, reducing the length of the circumference of that binding device to apply stress to the muscle, and causing muscle fatigue by means of a load applied to the muscle; and the load applied to the muscle for the purpose of causing muscle fatigue is such that blood flow to the muscle is obstructed (referred to below as Previous Example 3).

Patent document 1: International Published Patent Application No. 2006/009178
Patent document 2: Japanese Patent No. 2670421

SUMMARY OF THE INVENTION

Problems to be Solved by the Invention

There have been the following kinds of problems with Previous Example 1:

(1) With magnetoencephalography, PET, fMRI and the like, measuring must be performed with the subject in a prone position and at rest, which is not suited to brain measurements for the purpose of exercise training.

(2) As for electroencephalography, localized evaluation of the cerebrum is approximate, requiring hundreds of measurements to differentiate between the working of the primary motor area and supplementary motor areas; it lacks the sensitivity and precision needed for discussion of changes in an encephalograph from implementation of a single exercise.

(3) NIRS is capable of measuring the status of recovery after training in both the muscle and the brain in real time, but because NIRS measures light, even though different sites can be measured, issues such as differences in optical path lengths and volumetric evaluation of measured areas have been problematic. Because of this, even if NIRS measurements are taken at both the brain and the muscle, while increases and decreases in changes in oxyhemoglobin and deoxyhemoglobin can be compared qualitatively, the method has lacked quantifiability.

(4) Because $CMRO_2$, CBF, CBV and OEF could not be measured simultaneously using a single modality, it has been necessary to measure the values of CBF and CBV needed for calculating $CMRO_2$ (cerebral metabolic rate of oxygen) in separate experiments, and furthermore use estimated values for a plurality of parameters.

(5) Units for $CMRO_2$ and OEF, which are parameters concerning oxygen metabolism, are quantified in minutes, and it has not been possible to monitor them in real time in the order of milliseconds.

(6) In conventional NIRS brain functional measurements, even when, using equidistantly spaced emitter and receptor probes, the amounts of hemoglobin (light intensity) or tissue oxygen concentrations at the task starting point or the like differed at a ROI (region of interest), indicating that distances to the cerebral parenchyma from the scalp were not constant, computations have been done as if the distances were constant.

This can be said to be a problem not only for NIRS brain functional measurements, but for brain functional measurements in general.

Because distances to the cerebral parenchyma from the scalp are not constant, even with equidistantly spaced emitter and receptor probes, the amounts of hemoglobin (light intensity) measured will differ between different ROIs.

The distance from the scalp to the cerebral parenchyma in an adult, according to measurements of the human head, is around 1 cm from the scalp to the cerebral parenchyma at almost all sites (see FIG. 41); and it is thus desirable that emitter-receptor separation, as in probe arrays, be kept at around 2 cm, and at least 1 cm.

As for probes for measuring a plurality of sites, when they are used on the head, signals from the cerebral parenchyma can be included by maintaining a radius of 10-20 mm or more. For a plurality of measurement regions, a high-density arrangement of a plurality of emitter-receptor probes spaced at 1-2 cm or more makes measurement within each ROI as uniform as possible, but it has not been possible to quantify the size of a ROI.

Consequently, there has been a need for a measuring technique that would lessen the problem of non-uniform ROIs when performing NIRS measurements at a plurality of sites.

There have been the following kinds of problems with Previous Example 2.

(7) Electromyography is effective for measuring the strength and weakness of muscle contractions, but it has not been capable of differentiating and evaluating different states when the muscle is inactive.

(8) Because electromyography is not capable of simultaneously measuring the state of the brain when a muscle is not being moved, it cannot be used for simultaneous electrical measurement of the state of a muscle and the brain at rest after exercise is completed.

There have been the following kinds of problems with Previous Example 3.

(9) Pressure muscle training is a method in which a muscle is effectively trained by wrapping a rubber band around the muscle to produce hypoxia in the muscle. The present inventor, however, believes that the blind application of pressure is dangerous, because pressure training raises the blood pressure over a wide range in the brain, causing excessive pressure in the blood vessels of the brain.

A method for monitoring intracranial pressure is disclosed in Patent Reference 1.

(10) Muscles have been conventionally understood to move because of commands from the brain. It seems likely, however, that either muscle fatigue or brain fatigue might cause a muscle to stop moving. Nevertheless, it has been difficult to measure the relationship between the muscle and the brain, to see the degree of fatigue and recovery of the muscle and the brain, and thus initiate or stop training.

(11) There has been a need for a way to train the muscles while observing the brain, to see how much load applied to the muscle makes it possible to train a given brain address (site), and this has been difficult with previous techniques.

(12) Muscle training that is continued when the muscle will not move because of brain fatigue may be ineffective or the like, and it has been difficult to set muscle training levels without a load on the brain.

(13) The corticospinal tract, which connects the muscles to the cerebral cortex, is projected from the premotor area and the primary sensory cortex, as well as from M1.

In muscle training, because we do not understand, for example, which brain addresses are being trained, and the training load situation of the muscle based on the relationship with the brain, training menus, training start and finish times, and timing of breaks have not been set appropriately.

(14) There has been no NIRS simultaneous measurement apparatus for the brain and the muscle. When they are measured simultaneously, the shapes of the probes on the scalp and the probes on the muscles are different, and methods for analyzing and evaluating the data have not been discovered.

Methods for imaging and displaying functional relationships between the brain and the muscles have also not been discovered.

The present invention is for the purpose of solving the problems described above, and takes as its objective the provision of an apparatus and a program for evaluating biological function that is capable of simultaneously measuring, evaluating, imaging and displaying the biological functions of a plurality of sites with different biological functions, such as the brain and the muscle, different parts of the brain, different muscle locations, and the like.

Means for Solving the Problems

The apparatus for evaluating biological function is an apparatus for evaluating biological function having a plurality of living body probes for irradiating light to and receiving emitted light from a plurality of sites with different biological functions of a living body, and an apparatus body for entering light information detected by means of said plurality of living body probes and performing calculation, control and memory operations, and utilizing the near-infrared spectroscopy method, wherein said apparatus body comprising:

a calculating part for calculating amounts of change in oxyhemoglobin concentration and amounts of change in deoxyhemoglobin concentration and/or physiological indices including a variety of parameters derived from the relationships between them, based on light information from said plurality of living body probes;

an adjusting part for adjusting the physiological indices calculated by means of said calculating part and corresponding to said different sites of said living body in such a way that they can be compared; and a display part for displaying images based on information adjusted by means of said adjusting part.

Said adjusting part may also adjust different physiological indices at a plurality of sites with different biological functions in such a way that they can be compared.

Said adjusting part may also adjust in a comparison-capable way different physiological indices at a plurality of sites with different biological functions It may also be an apparatus in which said calculating part calculates correlation coefficients of said physiological indices at a plurality of sites with different biological functions, and said display part displays information concerning said correlation coefficients.

It may also be an apparatus in which said calculating part multiplies together the same physiological indices at a plurality of sites with different biological functions, and said display part displays information concerning products of said multiplication.

It may also be an apparatus in which said calculating part multiplies together different physiological indices at a plurality of sites with different biological functions, and said display part displays information concerning products of said multiplication.

Said plurality of sites of a living body with different biological functions further may include at least a brain site and a muscle site.

Said plurality of sites of a living body with different biological functions may include at least two different brain sites.

It may also be an apparatus in which said calculating part calculates change in blood volume concentration ($\Delta BV$) at a region of interest (ROI) by Equation 1:

$$\Delta BV = \Delta[Hb] + \Delta[HbO_2] \quad \text{(Equation 1)}$$

where $\Delta[Hb]$ is change in deoxyhemoglobin concentration, and $\Delta[HbO_2]$ is change in oxyhemoglobin concentration.

It may also be an apparatus in which said calculating part calculates the time of maximum muscle blood volume and the time of maximum cerebral blood volume at a desired region of interest (ROI) from a two-dimensional vector diagram showing the relationship between changes in blood volume concentration (ΔBV) at the brain and the muscle.

It may also be an apparatus in which said calculating part calculates change in oxygen exchange concentration (ΔOE) at a region of interest (ROI) by Equation 2:

$$\Delta OE = \Delta[Hb] - \Delta[HbO_2] \quad \text{(Equation 2)}$$

where $\Delta[Hb]$ is change in deoxyhemoglobin concentration, and $\Delta[HbO_2]$ is change in oxyhemoglobin concentration.

It may also be an apparatus in which said calculating part calculates the time of maximum muscle oxygen exchange and the time of maximum cerebral oxygen exchange at a desired region of interest (ROI) from a two-dimensional vector diagram showing the relationship between changes in oxygen exchange concentration (ΔOE) at the brain and the muscle.

It may also be an apparatus in which said calculating part calculates a ratio e, which is the ratio between change in oxygen exchange concentration (ΔOE) and change in blood volume concentration (ΔBV) at a region of interest (ROI) by Equation 3:

$$e = \Delta OE/\Delta BV = (\Delta[Hb] - \Delta[HbO_2])/(\Delta[Hb] + \Delta[HbO_2]) \quad \text{(Equation 3)}$$

where $\Delta[Hb]$ is change in deoxyhemoglobin concentration, and $\Delta[HbO_2]$ is change in oxyhemoglobin concentration.

It may also be an apparatus in which said calculating part calculates an angle E by Equation 3a:

$$E = \arctan(e) \quad \text{(Equation 3a)}$$

It may also be an apparatus in which said calculating part calculates a hybrid angle E (EH), which is an angle formed on a two-dimensional diagram, obtained by taking a first angle E of one of two different sites of a living body as the vertical axis and a second angle E of the other site as the horizontal axis and plotting them over time, between a first angle E $[E_1]$ and a second angle E $[E_2]$, by Equation 3b.

$$EH = \arctan(E_1/E_2) \quad \text{(Equation 3b)}$$

It may also be an apparatus in which said calculating part multiplies the same physiological index at two different sites and calculates a first hybrid angle ($H_1$), which is the angle formed on a two-dimensional diagram, obtained by taking the first multiplied value of one of the two different sites of a living body as the vertical axis and the second multiplied value from the other site as the horizontal axis and plotting them over time, between the first multiplied value and the second multiplied value, by Equation 3c.

$$H_1 = \arctan(\text{multiplied value}_1/\text{multiplied value}_2) \quad \text{(Equation 3c)}$$

It may also be an apparatus in which said calculating part multiplies different physiological indices at two different sites and calculates a second hybrid angle ($H_2$), which is the angle formed on a two-dimensional diagram, obtained by taking the third multiplied value of one of the two different sites of a living body as the vertical axis and the fourth multiplied value from the other site as the horizontal axis and plotting them over time, between the third multiplied value and the fourth multiplied value, by Equation 3d.

$$H_2 = \arctan(\text{multiplied value}_3/\text{multiplied value}_4) \quad \text{(Equation 3d)}$$

It may also be an apparatus in which said calculating part calculates a muscle/brain oxygen load ratio (M/B(1)) and a scalar $PL_1$ (power) during exercise at a plurality of regions of interest (ROIs) of the brain and the muscle, from on a two-dimensional diagram and by Equation 4:

$$M/B(1) = [\text{change in muscle oxygen exchange MOE}]/[\text{change in cerebral oxygen exchange COE}] \quad \text{(Equation 4)}$$

It may also be an apparatus in which said calculating part calculates a muscle/brain blood volume load ratio (M/B(2)) and a scalar $PL_2$ (power) during exercise at a plurality of regions of interest (ROIs) of the brain and the muscle, from on a two-dimensional diagram and by Equation 5:

$$M/B(2) = [\text{change in muscle blood volume MBV}]/[\text{change in cerebral blood volume CBV}] \quad \text{(Equation 5)}$$

It may also be an apparatus in which said calculating part calculates degree of oxygen saturation Y from a two-dimensional diagram, in which the horizontal axis is the amount of oxyhemoglobin (O) in a ROI and the vertical axis is the amount of deoxyhemoglobin (D) in the ROI, as the slope Y on the O/D plane, by Equation 6:

$$\text{Degree of oxygen saturation } Y = 1 - \arctan(Y \text{ angle}) \quad \text{(Equation 6)}$$

It may also be an apparatus in which said calculating part calculates a ratio E (ratio of oxygen exchange to blood volume), which is defined as the proportion of oxygen exchange (D−O) to total hemoglobin (D+O) at the measurement starting point $E_0$, from a two-dimensional diagram in which the horizontal axis is the amount of oxyhemoglobin (O) in a ROI and the vertical axis is the amount of deoxyhemoglobin (D) in the ROI, by Equation 7:

$$E = (D-O)/(D+O) \quad \text{(Equation 7)}$$

It may also be an apparatus in which said calculating part calculates change in the degree of oxygen saturation Y (ΔY), from a graph showing the relationship of change in degree of oxygen saturation Y to changes in oxyhemoglobin (ΔO) and changes in deoxyhemoglobin (D), in which the horizontal axis is the amount of oxyhemoglobin (O) in a ROI and the vertical axis is the amount of deoxyhemoglobin (D) in the ROI, by Equation 8:

$$\text{Change in oxygen saturation } \Delta Y = \arctan(\Delta Y \text{ angle}) \quad \text{(Equation 8)}$$

It may also be an apparatus in which said calculating part calculates estimated change in degree of oxygen saturation ΔY, by calculating blood volume at the start of measurement ($BV_0$) at a region of interest (ROI), from an arbitrary hypothetical maximum change in the hematocrit ($\Delta Ht_{max}$) with respect to the maximum change in blood volume, which is an actual measured value ($\Delta BV_{max}$), by Equation 9:

$$\Delta Ht_{max} = [(\Delta O + \Delta D)/(O+D)]_{max} = \Delta BV_{max}/BV_0 \quad \text{(Equation 9)}$$

It may also be an apparatus in which said $\Delta BV_{max}$ is selected as the maximum change from within a plurality of ROIs.

An estimated hematocrit value may also be set for a desired ROI.

It may also be an apparatus in which said calculating part determines an estimated change in degree of oxygen saturation ΔY at a region of interest (ROI) by calculating the blood volume at the start of measurement ($BV_0$) in the ROI and substituting it into Equation 10 or Equation 11, and said adjusting part adjusts the graphs showing time series changes in ΔY at different sites in such a way that they can be displayed by means of said display part.

$$\Delta Y = (-1/2)[\Delta OE/(BV_0 + \Delta BV)] + \quad \text{(Equation 10)}$$
$$(E_0/2)[\Delta BV/(BV_0 + \Delta BV)]$$
$$\approx (-1/2)[\Delta OE/(BV_0 + \Delta BV)] \quad \text{(Equation 11)}$$

where $\Delta OE$ is change in oxygen exchange concentration, $BV_0$ is blood volume at the start of measurement, $\Delta BV$ is change in blood volume concentration, and $E_0$ is the ratio E (ratio of oxygen exchange to blood volume), which is defined as the ratio of oxygen exchange (D×O) to total hemoglobin (D+O), at the measurement starting point.

Said adjusting part may also adjust graphs showing time series changes in $\Delta Y$ at different sites in such a way that they can be displayed by means of said display part.

It may also be an apparatus in which
said calculating part calculates L, which is defined by Equation 12, and
said adjusting part adjusts said physiological indices from different sites in such a way that they can be compared and displayed on unit circles of the same size, based on the maximum measured value of $\Delta L$.

$$(\Delta L)^2 = (\Delta[Hb])^2 + (\Delta[HbO_2])^2 \quad \text{(Equation 12)}$$

It may also be an apparatus in which
said adjusting part adjusts graphs showing changes in the products of multiplication of said physiological indices of different sites in such a way that they can be displayed on said display part.

Said display part may also display graphs showing time series changes, in which the vertical axis is said physiological indices and the horizontal axis is time.

Said display part may also display two-dimensional diagrams obtained by taking one of the two different aforementioned physiological indices as the vertical axis and the other as the horizontal axis and plotting them over time.

Said display part may also display images that are color-coded according to the size of the values of said physiological indices.

Said display part may also display changes in said physiological indices at rest, when there is a task load on said living body, and during recovery, on the same graph.

Said display part may also display changes in said physiological indices at rest, when there is a task load on said living body, and during recovery, as a dynamic state as the wave motion and rotational motion of hemoglobin-related parameters on a vector space, and may display the direction and strength of those changes on different graphs or image displays.

The program of the present invention is wherein it implements processing by the main body of said apparatus for evaluating biological function.

Advantages of the Invention

The present invention exhibits the following excellent effects.

(1) When a plurality of sites with different biological functions, such as brain and muscle, different parts of the brain, different muscle locations and the like, are measured simultaneously by means of NIRS, it is possible to compare and evaluate biological function even if the sizes of the ROIs are not uniform.

(2) It is possible to evaluate and display the brain sites where a given exercise causes the strongest oxygen load or blood pressure load over time, and thus continue, stop, or "change gears" in exercise training.

(3) Training can be done in such a way that the load on the brain sites is less than the exercise load.

(4) The brain can be trained in a situation in which the load on the muscles is pushed almost to the limit.

(5) The recovery periods of the brain and muscle can be evaluated and classified into the following four categories before starting training, extending the rest period, or "changing gears".

| Brain | Muscle |
|---|---|
| Completely recovered | Completely recovered |
| Not recovered | Not recovered |
| Completely recovered | Not recovered |
| Not recovered | Completely recovered |

(6) Because the stages of muscle fatigue and the stages of brain fatigue are different, the relative "weight" of brain training and muscle training can be adjusted by changing the dumbbell weight, etc.

(7) The muscle and the brain can be simultaneously and efficiently trained if the training load is decided while keeping an eye on muscle and brain fatigue.

(8) Interval exercise training can be performed effectively.

(9) For people with problems such as high blood pressure or vascular problems in the brain, rehabilitation (physical therapy) can be performed effectively.

(10) A helping hand causes extreme changes in the load ratio between oxygen consumption and blood volume in the brain and the muscle (M/B [muscle/brain] ratio), and watching it allows rehabilitation to be performed more efficiently.

(11) With fMRI, brain mapping (BOLD method) has been performed to estimate changes in degree of oxygen saturation using only changes in deoxyhemoglobin, which is paramagnetic, because fMRI cannot detect changes in oxyhemoglobin, which is diamagnetic. It has become clear, however, that with a method that uses only changes in deoxyhemoglobin, accurate oxygen saturation changes were not being obtained, and thus the present invention makes possible brain functional measurements that use highly precise time series changes in oxygen saturation, using changes in both oxyhemoglobin and deoxyhemoglobin simultaneously.

(12) Furthermore, by taking oxyhemoglobin and deoxyhemoglobin measurements and capturing them as indices, the changing dynamics of which are represented as waves and movement on a vector space, it is possible to create a plurality of indices representing the relationships between changes in the two: changes in oxyhemoglobin and changes in deoxyhemoglobin.

(13) Relationships between brain and muscle function can be imaged and displayed in real time

BEST MODE FOR CARRYING OUT THE INVENTION

An embodiment of the present invention is described below with reference to the drawings.

[A Summary of the Apparatus for Evaluating Biological Function]

Figure 1:
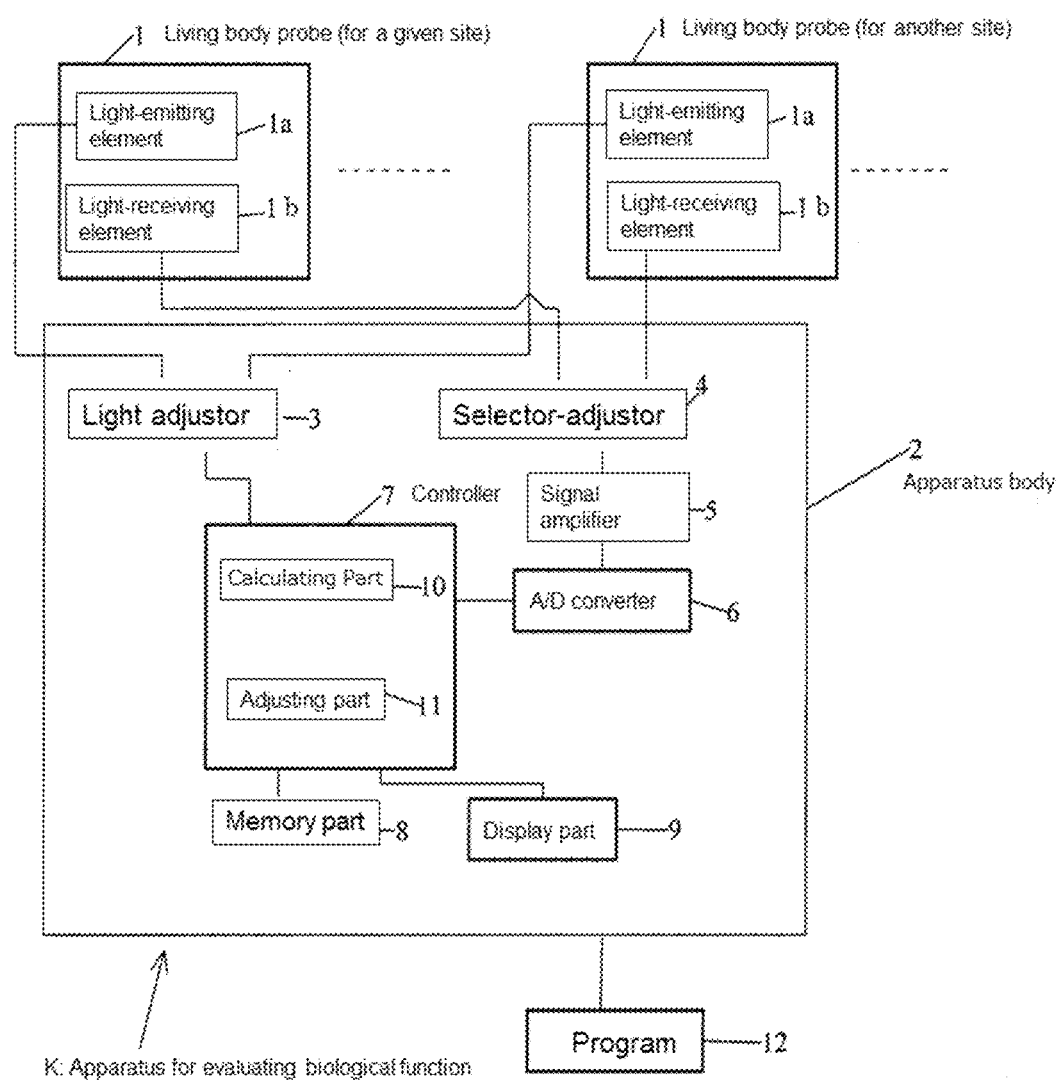
FIG. 1 is a block diagram showing the construction of an apparatus for evaluating biological function according to an embodiment of the present invention.
Figure 2:
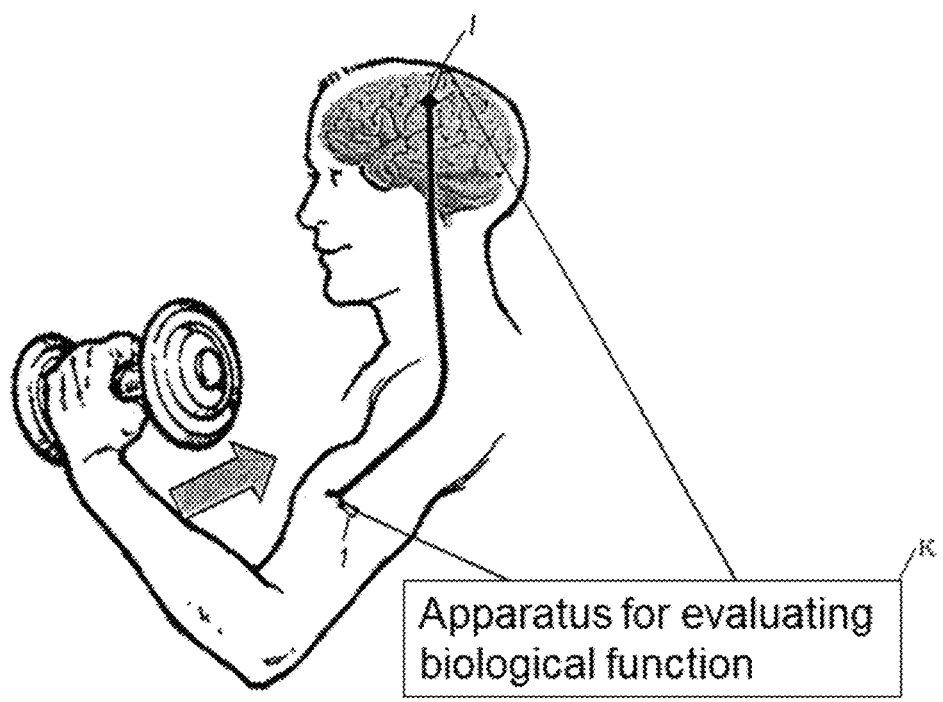
FIG. 2 is an explanatory view showing schematically an example of the use of an apparatus for evaluating biological function according to an embodiment of the present invention.

FIG. 1 is a block diagram showing the construction of an apparatus for evaluating biological function according to an embodiment of the present invention, and FIG. 2 is an explanatory view showing schematically an example of the use of an apparatus for evaluating biological function of the embodiment of the present invention.

The apparatus for evaluating biological function K of the embodiment of the present invention shown in FIGS. 1 and 2 has a plurality of living body probes 1, which irradiate light to each of a plurality of sites of the living body with different biological function and receive light that is emitted, and an apparatus body 2, into which light information detected by the plurality of living body probes 1 is input and which performs calculations and control and memory [functions]; it utilizes near-infrared spectroscopy and is used for evaluating biological function.

Each living body probe 1 is composed of at least two light-emitting elements (light-emitting diodes) 1a . . . for irradiating light to the desired measurement site (tissue) of a living body, and at least two light-receiving elements (photodiodes) 1b . . . for receiving light from the measurement site that has been transmitted, reflected, or scattered, etc., after its interaction with the living body.

Living body probes 1 may be placed on and measurements taken from the brain, the muscles of the arm, the muscles of the jaw, the muscles of the fingertips, and the like, but the shape of the living body probes, the surface area measured, how they are placed, and the like, are determined according to the locations where they are placed.

The space between light-emitting probes 1a and light-receiving probes 1b is around 1.5-3 cm when measuring the brain, around 2-3 cm when measuring a muscle of the arm or the jaw, around 5-10 mm when measuring the muscle of the fingertips, and around 2-3.5 mm when measuring the gums in the mouth.

In addition, when living body probes 1 are disposed on a muscle of the arm, if the probes are arranged parallel to the arm, specific muscle oxygen metabolism that accompanies longitudinal extension and contraction of that muscle can be measured. This is because longitudinal extension and contraction of the muscle are reflected in the direction of the longitudinal section of the muscle. If living body probes 1 are placed with the probes arranged perpendicular to the arm, specific muscle oxygen metabolism that accompanies crosswise extension and contraction of that muscle can be measured. This is because changes in the cross-sectional area accompanying flexure and extension are reflected in the cross-section of the muscle.

In addition, an array (in a matrix) of a plurality of living body probes is preferred, in which light-emitting elements 1a and light-receiving elements 1b are spaced at equal intervals. However, for the purpose of identifying brain sites having the most relevance to the muscle exercise selected—that is, identifying from among a plurality of brain measurement sites the locations where the exercise causes the greatest changes (increase/decrease) in oxygen metabolism and the locations where it causes the greatest changes (increase/decrease) in cerebral blood volume, and the sites with the highest correlation—it is not necessary that the distance between light-emitting elements 1a and light-receiving elements 1b be equal; a random arrangement is also possible.

In addition, a two-stage measuring method is possible, in which, once a site with a strong correlation is ascertained, a high-density living body probe array (short distances between light-emitting elements 1a and light-receiving elements 1b) is set up to precisely identify the corresponding site. Namely, it is possible to investigate correlations between muscle and brain and exclude the previously problematic influence of differences in light signal-to-noise ratios at different sites, differences in optical path lengths, and differences in size of the sampling regions sandwiched between living body probes 1.

The apparatus body 2 has a light intensity adjustor 3 for adjusting the intensity of light emitted from light-emitting elements 1a . . . ; a selector-adjustor 4 for selectively activating or deactivating specific light-receiving elements 1b . . . as desired, and for adjusting overall measurement sensitivity; a gain-controllable signal amplifier 5 for amplifying signals from light-receiving elements 1b . . . ; an A/D converter 6 for digitizing the output from signal amplifier 5; a controller 7 for implementing specified mathematical processing based on control processing from various parts of the apparatus and/or output from A/D converter 6; a memory part 8 used for recording output from A/D converter 7, control data from various parts of the apparatus, results of mathematical processing and the like; and a display part 9 for creating displays based on output results from A/D converter 6, results of mathematical processing and the like.

The apparatus body 2 may also have functions for printing various kinds of data and for transmitting and receiving data over a network.

Controller 7 has a calculating part 10 for calculating changes in oxyhemoglobin concentration and changes in deoxyhemoglobin concentration based on light data from the plurality of living body probes 1, and parameters derived from the relationships between them; and an adjusting part 11 for adjusting the amounts of changes and parameters corresponding to the different sites of the living body, calculated by means of calculating part 10, in such a way that they can be compared and displayed on display part 9.

As for the light-emitting probes 1a . . . of the living body probes, two types are provided: those irradiating light with a wavelength of 730 nm, and those irradiating light with a wavelength of 850 nm. (These wavelength numbers are examples; they are not limited to these, and 3 or more wavelengths may also be used in combination.) These may be disposed alternately in a linear direction, but when exploring other patterns, it is important to take into consideration wavelength-dependent attenuation in the tissue and dispose the probes in such away that the received light intensity can be measured in a balanced way. All of light-emitting elements 1a . . . are connected to light adjustor 3 of the apparatus body 2, and the emitted light intensity can be adjusted, either overall or individually.

On the other hand, all the light-receiving elements 1b . . . are connected to signal amplifier 5 through selector-adjustor 4 of the apparatus body; and the received-light signals output from each of light-receiving elements 1b . . . are output, with all or a part of them selectively adjusted by selector-adjustor 4, to signal amplifier 5, where they are amplified. Then, the amplified received-light signals are digitized by A/D converter 6 and output to controller 7.

Controller 7, after applying a low-pass filter to the digital data input from A/D converter 6 to eliminate noise, records this processed data (referred to below as "received light intensity") chronologically in memory part 8.

In addition, controller 7 executes the operations described below, based on the received light intensity obtained. First, it calculates optical density for wavelength 730 nm ($OD_{730}$) by means of Equation 13, and optical density for wavelength 850 nm ($OD_{850}$) by means of Equation 14, and at the same time it records the results of these computations chronologically in memory part 8.

$$OD_{730}=\log_{10}(I_{0\ 730}/I_{730}) \quad \text{(Equation 13)}$$

$$OD_{850}=\log_{10}(I_{0\ 850}/I_{850}) \quad \text{(Equation 14)}$$

where:
$I_{0\ 730}$ is emitted light intensity for wavelength 730 nm
$I_{730}$ is received light intensity for wavelength 730 nm
$I_{0\ 850}$ is emitted light intensity for wavelength 850 nm
$I_{850}$ is received light intensity for wavelength 850 nm The relationships between changes in oxyhemoglobin concentration, changes in deoxyhemoglobin concentration, and changes in optical density expressed by Equations 15 and 16 are known to exist from theory known in the art.

$$\Delta OD_{730}=a_1\Delta[HbO_2]+a_1'\Delta[Hb] \quad \text{(Equation 15)}$$

$$\Delta OD_{850}=a_2\Delta[HbO_2]+a_2'\Delta[Hb] \quad \text{(Equation 16)}$$

where:
$\Delta OD_{730}$ is change in optical density for wavelength 730 nm
$\Delta OD_{850}$ is change in optical density for wavelength 850 nm
$\Delta[HbO_2]$ is change in oxyhemoglobin concentration
$\Delta[Hb]$ is change in deoxyhemoglobin concentration
$a_1, a_1', a_2, a_2'$ are optical density coefficients Equations 17 and 18 can consequently be obtained from these simultaneous equations known in the art.

$$\Delta[HbO_2]=a\{\Delta OD_{730}-(a_1'/a_2')\Delta OD_{850}\} \quad \text{(Equation 17)}$$

$$\Delta[Hb]=a(a_2/a_2')[(a_1/a_2)\Delta OD_{850}-\Delta OD_{730}] \quad \text{(Equation 18)}$$

where:
$a=a_2'/(a_1a_2'-a_1'a_2)\approx 1$ (1 or a value approaching 1)

Accordingly, after determining the change in optical density for wavelength 730 nm ($\Delta OD_{730}$) and the change in optical density for wavelength 850 nm ($\Delta OD_{850}$), the change in oxyhemoglobin concentration ($\Delta[HbO_2]$) is calculated by means of Equation 17 and the change in deoxyhemoglobin concentration ($\Delta[Hb]$) by means of Equation 18, and the results of these calculations are recorded chronologically in memory part 8. The change in total hemoglobin concentration ($\Delta[\text{total Hb}]$) is shown by Equation 19.

$$\Delta[\text{total }Hb]=\Delta[HbO_2]+\Delta[Hb] \quad \text{(Equation 19)}$$

Concentration changes in oxyhemoglobin and deoxyhemoglobin in the capillaries, induced by stimulus to the tissue, can change in the 9 patterns shown below, according to the possible combinations of positive and negative.

(1) $\Delta HbO_2$ increase; $\Delta Hb$ increase
(2) $\Delta HbO_2$ increase; $\Delta Hb$ decrease
(3) $\Delta HbO_2$ increase; $\Delta Hb$ is zero
(4) $\Delta HbO_2$ decrease; $\Delta Hb$ increase
(5) $\Delta HbO_2$ decrease; $\Delta Hb$ decrease
(6) $\Delta HbO_2$ decrease; $\Delta Hb$ is zero
(7) $\Delta HbO_2$ is zero; $\Delta Hb$ increase (8) $\Delta HbO_2$ is zero; $\Delta Hb$ decrease (9) $\Delta HbO_2$ is zero; $\Delta Hb$ is zero In actuality, the above patterns of tissue metabolic activity are changing over time according to differences in such factors as the conditions of stimulus application and the physiological state at rest. $\Delta[Hb]$ and $\Delta[HbO_2]$ vary in the capillaries as blood flow and metabolic activities for taking up oxygen into the tissues from oxyhemoglobin in the capillaries.

Accordingly, in the present invention, various parameters, derived based on changes in oxyhemoglobin concentration $\Delta[HbO_2]$ and changes in deoxyhemoglobin concentration $\Delta[Hb]$, are calculated by means of the calculating part 10 of controller 7.

In addition, for the purpose of simultaneously measuring, evaluating, imaging and displaying the biological function of a plurality of sites with different biological functions, such as brain and muscle, different parts of the brain, different muscle locations or the like, adjusting part 11 adjusts the changes in concentration and parameters corresponding to the different sites in the living body and calculated by means of calculating part 10 in such a way that they can be compared and displayed on display part 9.

For example, adjusting part 11 may adjust the units and the size of the increments on the axes of a graph, the size, shape and color of an image, and the like.

Because changes and parameters in, for example, the muscle and the brain are of different magnitudes, if their units and increments and so on are changed, then things like straight line slopes will also change. However, the combination of these positive and negative values, and the direction of trajectories on a two-dimensional diagram (whether they turn right or left), will not change, nor will their phase on a two-dimensional diagram change; and thus it is possible to visualize them as composite indices and observe their dynamics.

Figure 3:
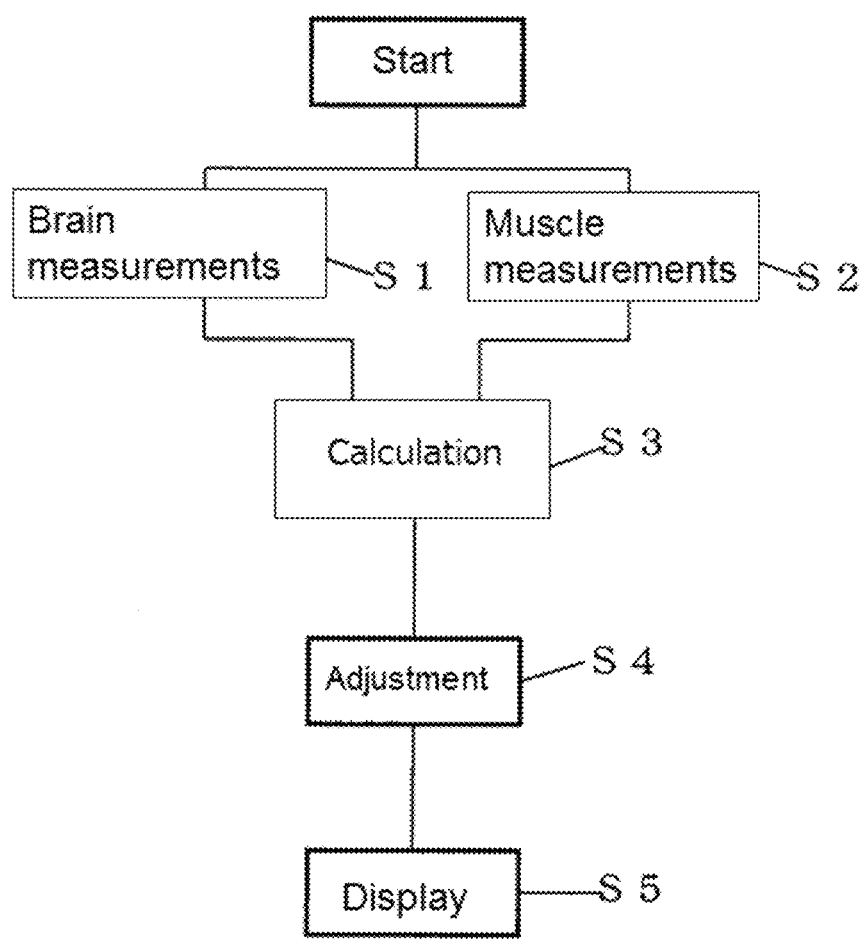
FIG. 3 is a flowchart illustrating the operation of the apparatus for evaluating biological function according to an embodiment of the present invention.

FIG. 3 is a flowchart illustrating the operation of the apparatus for evaluating biological function of the embodiment of the present invention.

As shown in FIG. 3, first, measurements are taken from a given site of a living body, for example, the primary motor area (M1) of the left brain, using a living body probe 1 (Step S1); and measurements are taken simultaneously from another site of the living body, for example, a muscle of the right arm (the biceps) using a living body probe 1 (Step S2).

Next, based on light information from each of the plurality of living body probes 1, changes in oxyhemoglobin concentration and changes in deoxyhemoglobin concentration and parameters derived from the relationships between them are calculated by means of calculating part 10 of controller 7 (Step S3).

The changes in concentration and parameters corresponding to the different sites of the living body calculated by calculating part 10 are subsequently adjusted in such a way that they can be compared, by means of adjusting part 11 of controller 7 (Step S4), and a variety of graphs and images are displayed on display part 9 (Step S5).

[Display by Means of Graphs Showing Time Series Changes]

Figure 4:
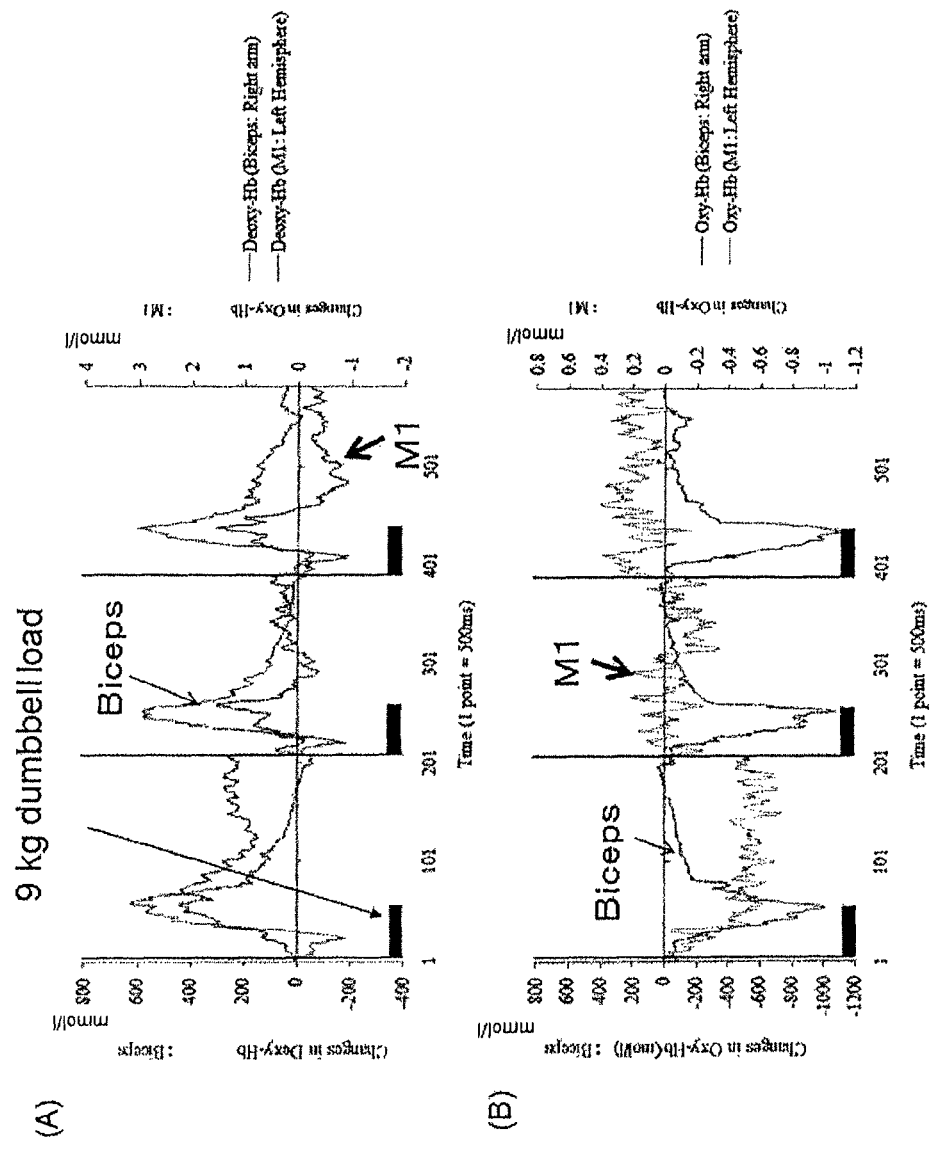
FIG. 4 shows time series changes in deoxyhemoglobin and oxyhemoglobin in the brain (left brain primary motor area) and the muscle (right arm biceps) when a subject is given a load-bearing task of lifting a 9 kg dumbbell: (A) is a graph in which the horizontal axis is time, the right vertical axis is change in deoxyhemoglobin concentration in the brain (left brain primary motor area), and the left vertical axis is change in deoxyhemoglobin concentration in the muscle (right arm); (B) is a graph in which the horizontal axis is time, the right vertical axis is change in oxyhemoglobin concentration in the brain (left brain primary motor area), and the left vertical axis is change in oxyhemoglobin concentration in the muscle (right arm).

FIG. 4 shows time series changes in deoxyhemoglobin and oxyhemoglobin in the brain (left brain primary motor area) and the muscle (right arm biceps) when [a subject] is given a load-bearing task of lifting a 9 kg dumbbell: (A) is a graph in which the horizontal axis is time, the right vertical axis is change in deoxyhemoglobin concentration in the brain (left brain primary motor area), and the left vertical axis is change in deoxyhemoglobin concentration in the muscle (right arm); (B) is a graph in which the horizontal axis is time, the right vertical axis is change in oxyhemoglobin concentration in the brain (left brain primary motor area), and the left vertical axis is change in oxyhemoglobin concentration in the muscle (right arm).

Figure 5:
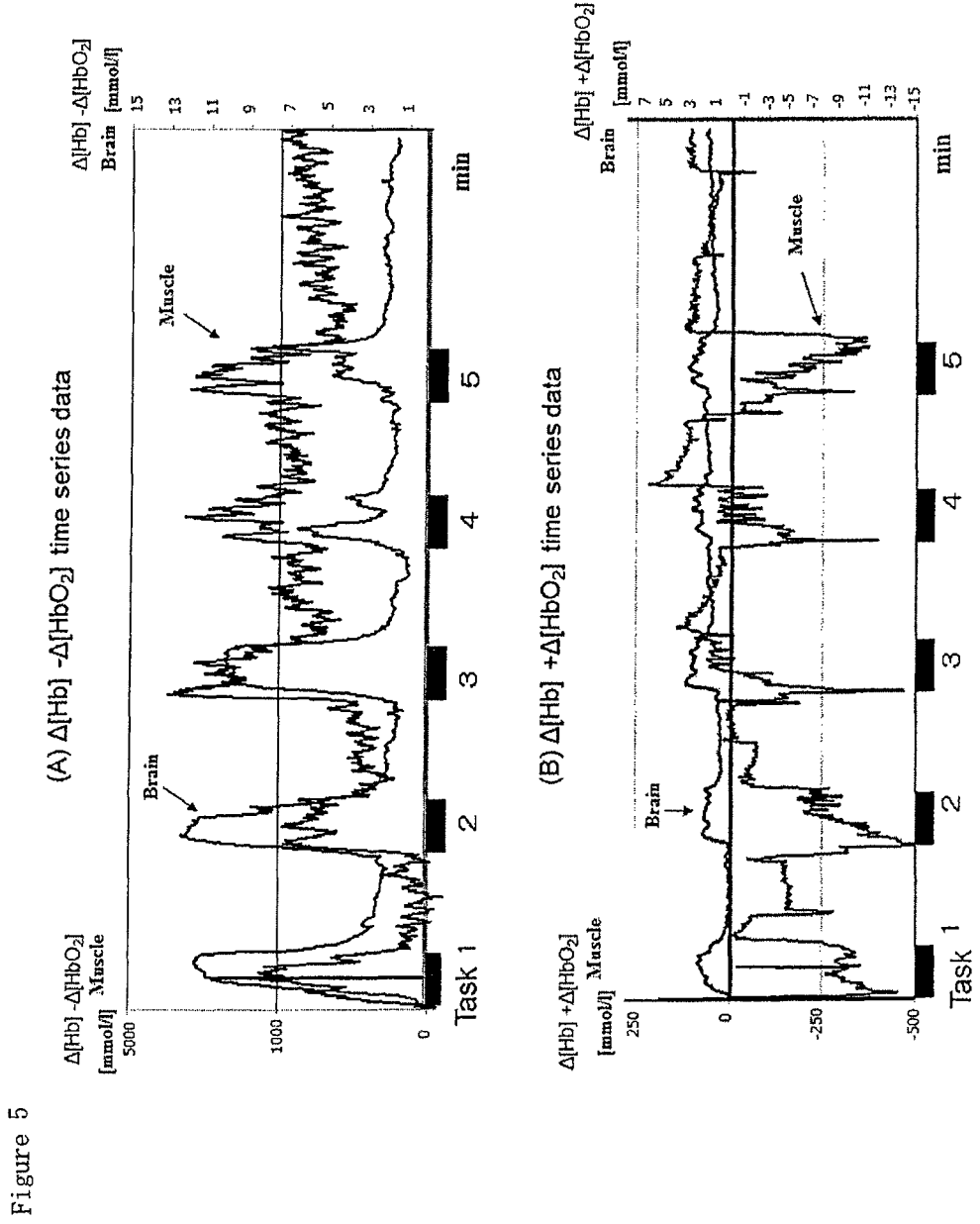
FIG. 5 shows time series changes in $\Delta[Hb]-\Delta[HbO_2]$ and $\Delta[Hb]+\Delta[HbO_2]$ in the brain (left brain primary motor area) and the muscle (right arm biceps), when [a subject] is given a task at specified intervals: (A) is a graph in which the horizontal axis is time, the right vertical axis is $\Delta[Hb]-\Delta[HbO_2]$ in the brain (left brain primary motor area M1), and the left vertical axis is $\Delta[Hb]-\Delta[HbO_2]$ in the muscle (right arm biceps); (B) is a graph in which the horizontal axis is time, the right vertical axis is $\Delta[Hb]+\Delta[HbO_2]$ in the brain (left brain primary motor area M1), and the left vertical axis is $\Delta[Hb]+\Delta[HbO_2]$ in the muscle (right arm biceps).

FIG. 5 shows time series changes in $\Delta[Hb]-\Delta[HbO_2]$ and $\Delta[Hb]+\Delta[HbO_2]$ in the brain (left brain primary motor area) and the muscle (right arm biceps), when [a subject] is given a task at specified intervals: (A) is a graph in which the horizontal axis is time, the right vertical axis is $\Delta[Hb]-\Delta[HbO_2]$ in the brain (left brain primary motor area M1), and the left vertical axis is $\Delta[Hb]-\Delta[HbO_2]$ in the muscle (right arm biceps); (B) is a graph in which the horizontal axis is time, the right vertical axis is $\Delta[Hb]+\Delta[HbO_2]$ in the brain (left brain primary motor area M1), and the left vertical axis is $\Delta[Hb]+\Delta[HbO_2]$ in the muscle (right arm biceps).

As can be seen from FIGS. 4 and 5, by displaying time series data for changes in various concentrations and the like from the brain and the muscle side by side, we can see that concentration changes, etc., increase and decrease with task loads.

Evaluating interrelationships between the brain and the muscle, however, is difficult.

Accordingly, the apparatus K for evaluating biological function of this embodiment of the present invention makes evaluation of interrelationships between different sites possible by using two-dimensional diagrams to compare changes in concentration and parameters corresponding to different sites in the living body.

[Display by Means of Two-Dimensional Diagrams]

Figure 6:
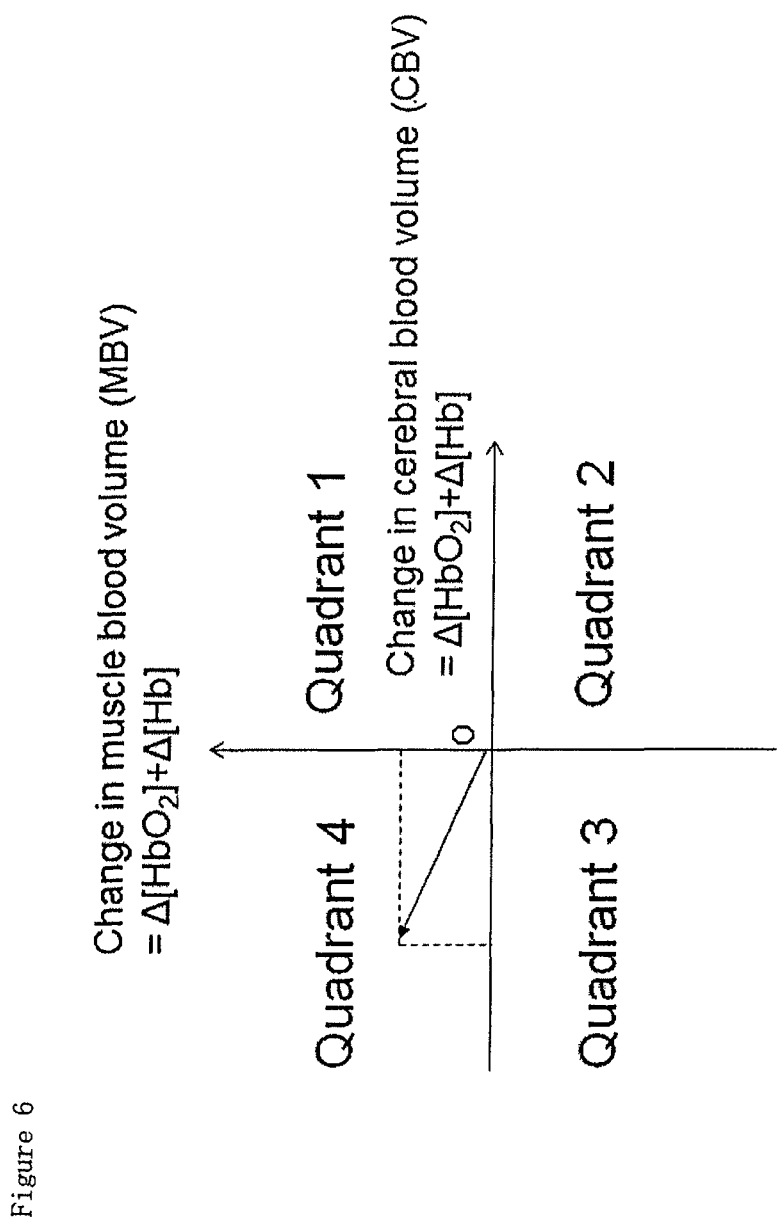
FIG. 6 is a two-dimensional diagram obtained by plotting simultaneous measurements over time, in which the horizontal axis is change in cerebral blood volume (CBV; $\Delta[Hb]+\Delta[HbO_2]$; primary motor area M1 of the brain) and the vertical axis is change in muscle blood volume (MBV; $\Delta[Hb]+\Delta[HbO_2]$; right arm biceps).
Figure 7:
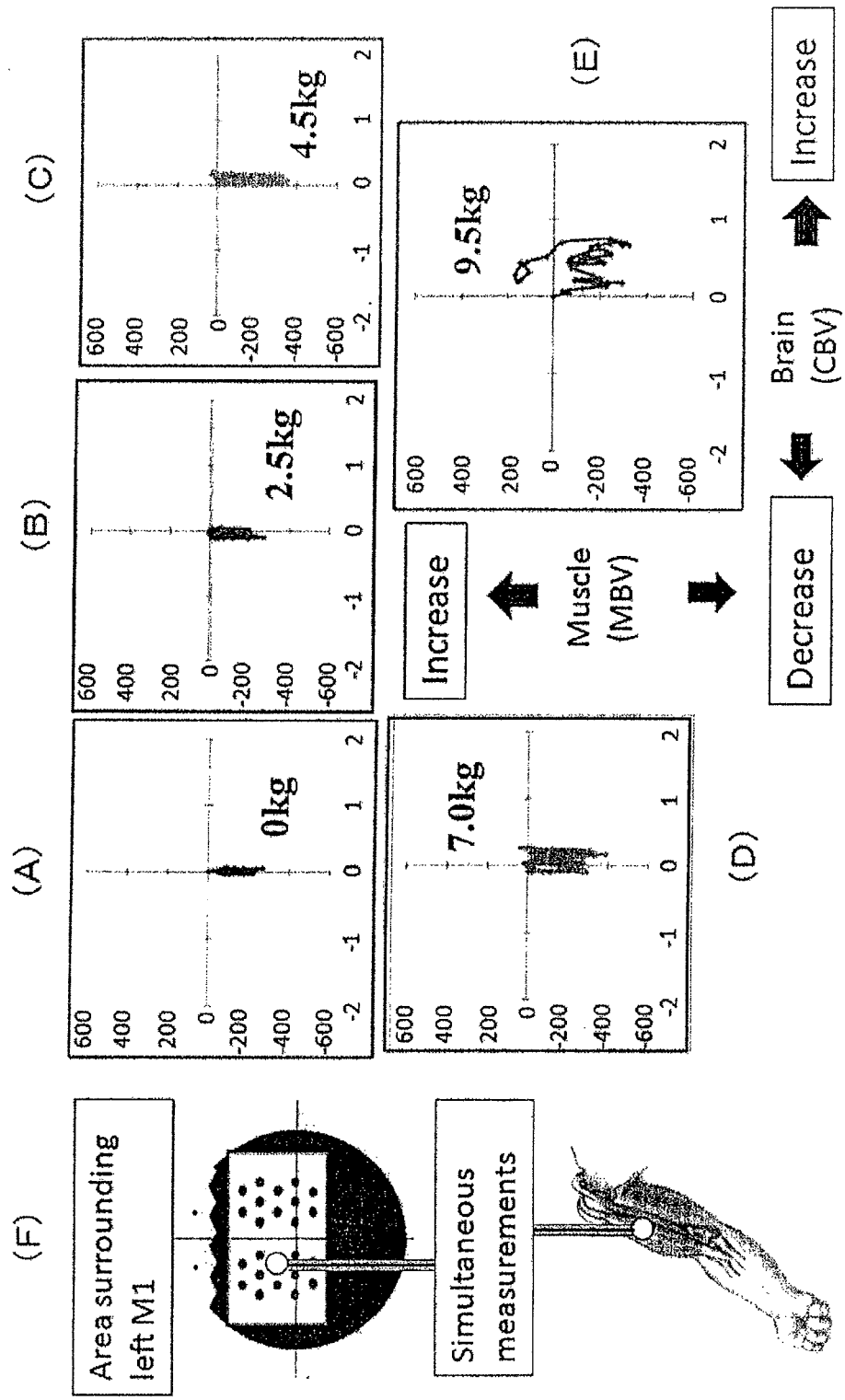
FIG. 7(A)-(E) are two-dimensional diagrams obtained by plotting simultaneous measurements over time, in which the horizontal axis is change in cerebral blood volume (CBV; $\Delta[Hb]+\Delta[HbO_2]$; area surrounding the left brain primary motor area M1) and the vertical axis is change in muscle blood volume (MBV; $\Delta[Hb]+\Delta[HbO_2]$; right arm biceps); (F) is an explanatory view.

FIG. 6 is a two-dimensional diagram obtained by plotting simultaneous measurements over time, in which the horizontal axis is change in cerebral blood volume (CBV; $\Delta[Hb]+\Delta[HbO_2]$; primary motor area M1 of the brain) and the vertical axis is change in muscle blood volume (MBV; $\Delta[Hb]+\Delta[HbO_2]$; right arm biceps).

Here, CBV is the abbreviation for cerebral blood volume, and MBV, muscle blood volume.

Here, $\Delta[Hb]$ is change in deoxyhemoglobin concentration, and $\Delta[HbO_2]$, change in oxyhemoglobin concentration.

Concentration changes in total hemoglobin ($\Delta[Hb]+\Delta[HbO_2]$) in the capillaries of the brain, induced by the stimulus of muscle exercise, can change in the 9 patterns shown below, according to the possible combinations of increase and decrease.

| | Total hemoglobin in muscle $\Delta[Hb] + \Delta[HbO_2]$ | Total hemoglobin in brain $\Delta[Hb] + \Delta[HbO_2]$ | |
|---|---|---|---|
| (1) | Increases | Increases | Quadrant 1 |
| (2) | Increases | No change(zero) | |
| (3) | Increases | Decreases | Quadrant 4 |
| (4) | Decreases | Increases | Quadrant 2 |
| (5) | Decreases | No change(zero) | |
| (6) | Decreases | Decreases | Quadrant 3 |
| (7) | No change(zero) | Increases | |
| (8) | No change(zero) | No change(zero) | |
| (9) | No change(zero) | Decreases | |

In FIG. 6, Quadrant 1 shows increasing blood pressure in the brain and the muscle; in this quadrant, the muscle is pumping, and the blood pressure in the brain is rising. Quadrant 2 shows increasing blood pressure in the brain, and ischemia and increased contraction in the muscle; in this quadrant, the oxygen loads to the brain and muscle are sufficiently ensured. Quadrant 3 shows ischemia of the brain and muscle; in this quadrant, the brain still has strength in reserve, and the oxygen load to the muscle is sufficiently ensured. Quadrant 4 shows a muscle blood pressure increase greater than the brain blood pressure decrease; in this quadrant, the brain has reserve capacity, and the muscle is pumped up.

FIG. 7(A)-(E) are two-dimensional diagrams obtained by plotting simultaneous measurements over time, in which the horizontal axis is change in cerebral blood volume (CBV; $\Delta[Hb]+\Delta[HbO_2]$; area surrounding the left brain primary motor area M1) and the vertical axis is change in muscle blood volume (MBV; $\Delta[Hb]+\Delta[HbO_2]$; right arm biceps); in (A), no dumbbell is lifted; in (B), a 2.5 kg dumbbell is lifted; in (C), a 4.5 kg dumbbell is lifted; in (D), a 7.0 kg dumbbell is lifted; in (E), a 9.5 kg dumbbell is lifted; (F) is an explanatory view.

Units on the vertical and horizontal axes are mmol/l.

Figure 8:
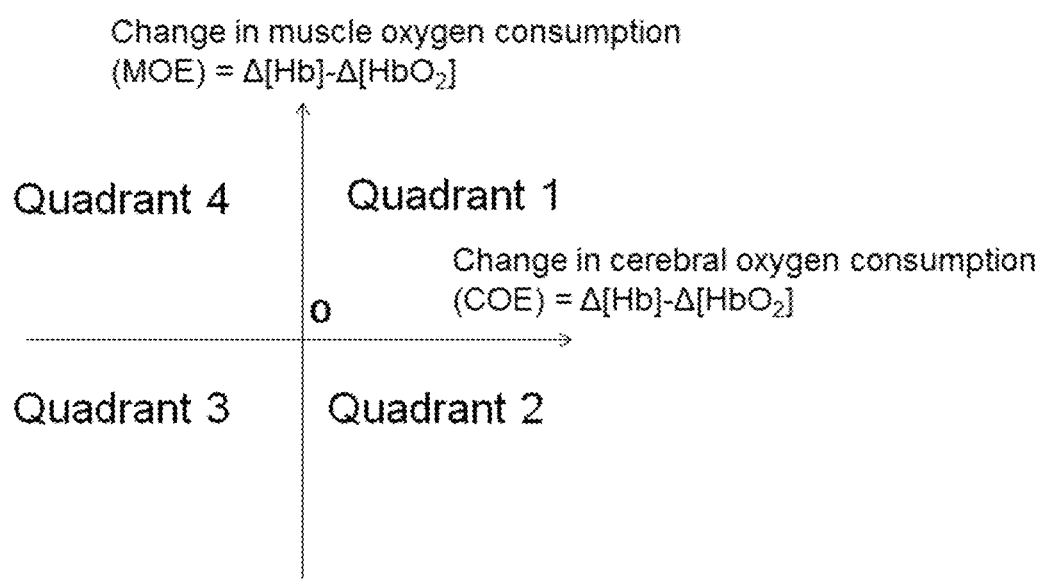
FIG. 8 is a two-dimensional diagram obtained by plotting simultaneous measurements over time, in which the horizontal axis is change in cerebral oxygen exchange (COE; $\Delta[Hb]-\Delta[HbO_2]$; primary motor area M1 of the brain) and the vertical axis is change in muscle oxygen exchange (MOE; $\Delta[Hb]-\Delta[HbO_2]$; biceps of the arm).

FIG. 8 is a two-dimensional diagram obtained by plotting simultaneous measurements over time, in which the horizontal axis is change in cerebral oxygen exchange (COE; $\Delta[Hb]-\Delta[HbO_2]$; primary motor area M1 of the brain) and the vertical axis is change in muscle oxygen exchange (MOE; $\Delta[Hb]-\Delta[HbO_2]$; biceps of the arm).

Here, COE is the abbreviation for cerebral oxygen exchange, and MOE, muscle oxygen exchange.

Concentration changes in oxygen consumption ($\Delta[Hb]-\Delta[HbO_2]$) in the capillaries of the brain, induced by stimulus in response to muscle exercise, can change in the 9 patterns shown below, according to the possible combinations of increase and decrease.

|  | Muscle oxygen consumption $\Delta[Hb] - \Delta[HbO_2]$ | Brain oxygen consumption $\Delta[Hb] - \Delta[HbO_2]$ |  |
|---|---|---|---|
| (1) | Increases | Increases | Quadrant 1 |
| (2) | Increases | No change(zero) |  |
| (3) | Increases | Decreases | Quadrant 4 |
| (4) | Decreases | Increases | Quadrant 2 |
| (5) | Decreases | No change(zero) |  |
| (6) | Decreases | Decreases | Quadrant 3 |
| (7) | No change(zero) | Increases |  |
| (8) | No change(zero) | No change(zero) |  |
| (9) | No change(zero) | Decreases |  |

In FIG. 8, Quadrant 1 shows increased activity in the brain and the muscle; in this quadrant, both brain and muscle are working efficiently. Quadrant 2 shows the brain is more active than the muscle; in this quadrant, more load can be applied to the muscle. Quadrant 3 shows reduced activity of the brain and muscle; in this quadrant, the brain and the muscle are recovering adequately. Quadrant 4 shows the muscle is more active than the brain; in this quadrant more load can be applied to the brain.

FIG. 9(A)-(E) are two-dimensional diagrams obtained by plotting simultaneous measurements over time, in which the horizontal axis is change in cerebral oxygen exchange (COE; $\Delta[Hb]-\Delta[HbO_2]$; left brain primary motor area M1) and the vertical axis is change in muscle oxygen exchange (MOE; $\Delta[Hb]-\Delta[HbO_2]$; right arm biceps); in (A), no dumbbell is lifted; in (B), a 2.5 kg dumbbell is lifted; in (C), a 4.5 kg dumbbell is lifted; in (D), a 7.0 kg dumbbell is lifted; in (E), a 9.5 kg dumbbell is lifted; (F) is an explanatory view.

Units on the vertical and horizontal axes are mmol/l.

Figure 9:
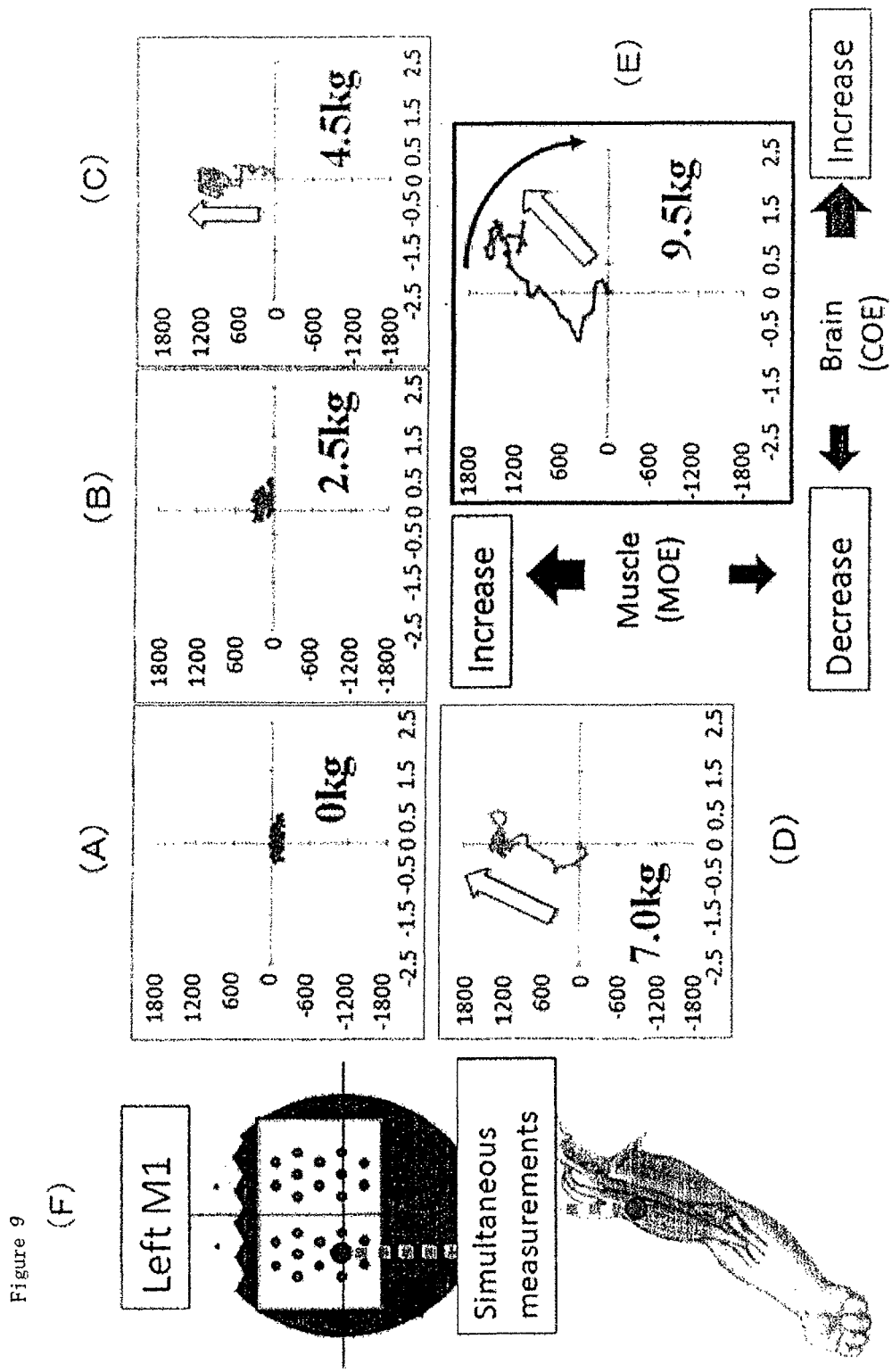
FIG. 9(A)-(E) are two-dimensional diagrams obtained by plotting simultaneous measurements over time, in which the horizontal axis is change in cerebral oxygen exchange (COE; $\Delta[Hb]-\Delta[HbO_2]$; left brain primary motor area M1) and the vertical axis is change in muscle oxygen exchange (MOE; $\Delta[Hb]-\Delta[HbO_2]$; right arm biceps); (F) is an explanatory view.

As shown in FIG. 9(E), a site where oxygen exchange increases and the load causes the M/B(1) ratio (muscle-to-brain oxygen load ratio during exercise) to approach zero in a clockwise direction becomes a target for strengthening by increasing neural activity.

Here, M/B(1) is defined as:

$M/B(1)$ (muscle-to-brain oxygen load ratio)=change in muscle oxygen exchange (MOE)/change in cerebral oxygen exchange (COE)   (Equation 20)

FIG. 10(A)-(E) are two-dimensional diagrams obtained by plotting simultaneous measurements over time, in which the horizontal axis is change in cerebral oxygen exchange (COE; $\Delta[Hb]-\Delta[HbO_2]$; area surrounding left brain primary motor area M1) and the vertical axis is change in muscle oxygen exchange (MOE; $\Delta[Hb]-\Delta[HbO_2]$; right arm biceps); in (A), no dumbbell is lifted; in (B), a 2.5 kg dumbbell is lifted; in (C), a 4.5 kg dumbbell is lifted; in (D), a 7.0 kg dumbbell is lifted; in (E), a 9.5 kg dumbbell is lifted; (F) is an explanatory view.

Units on the vertical and horizontal axes are mmol/l.

Figure 10:
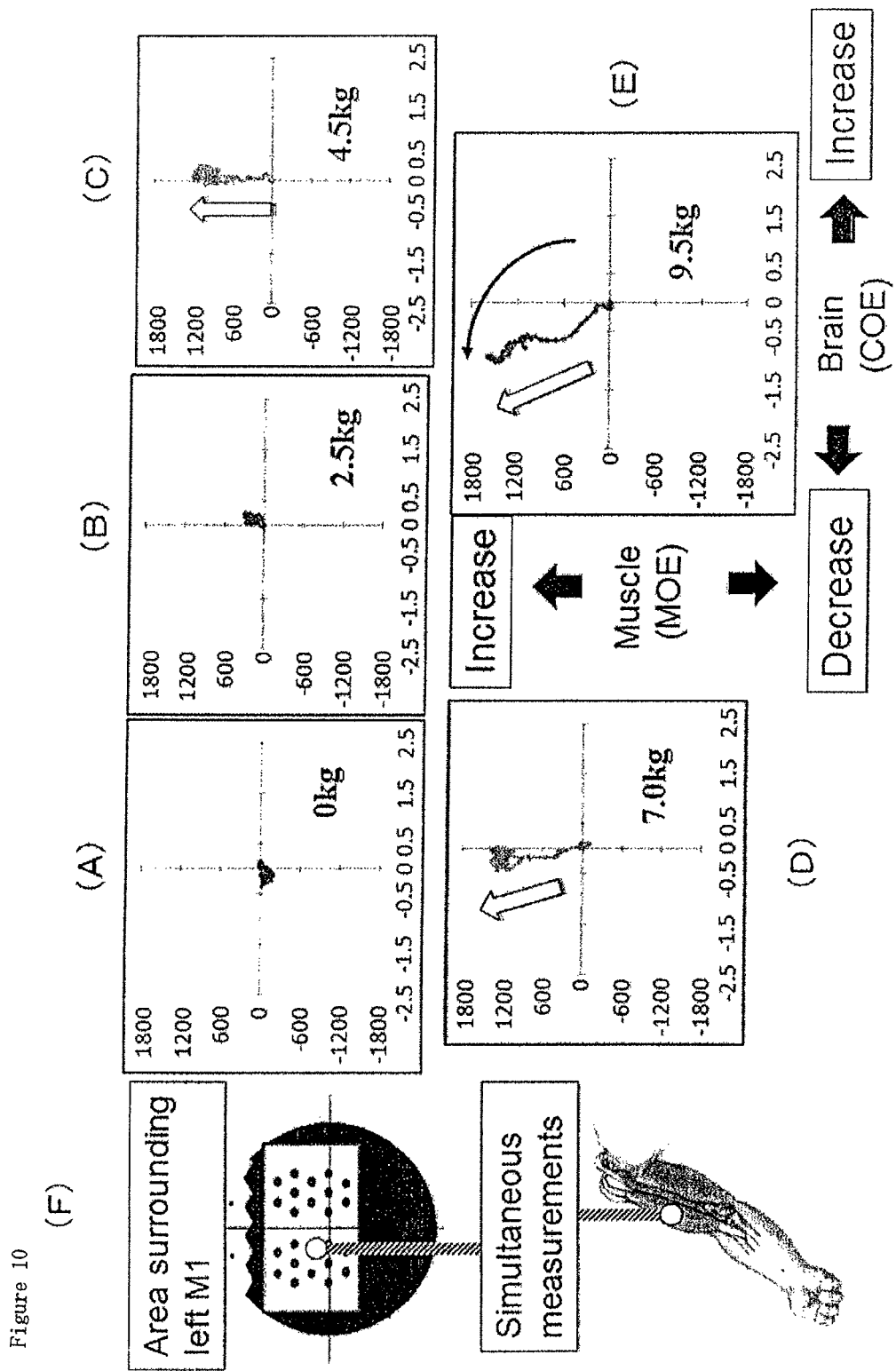
FIG. 10(A)-(E) are two-dimensional diagrams obtained by plotting simultaneous measurements over time, in which the horizontal axis is change in cerebral oxygen exchange (COE; $\Delta[Hb]-\Delta[HbO_2]$; area surrounding left brain primary motor area M1) and the vertical axis is change in muscle oxygen exchange (MOE; $\Delta[Hb]-\Delta[HbO_2]$; right arm biceps); (F) is an explanatory view.

As shown in FIG. 10(E), a site where the trajectory shifts in a counter-clockwise direction shows high oxidation, making it a target for training to cause increased blood flow.

Figure 11:
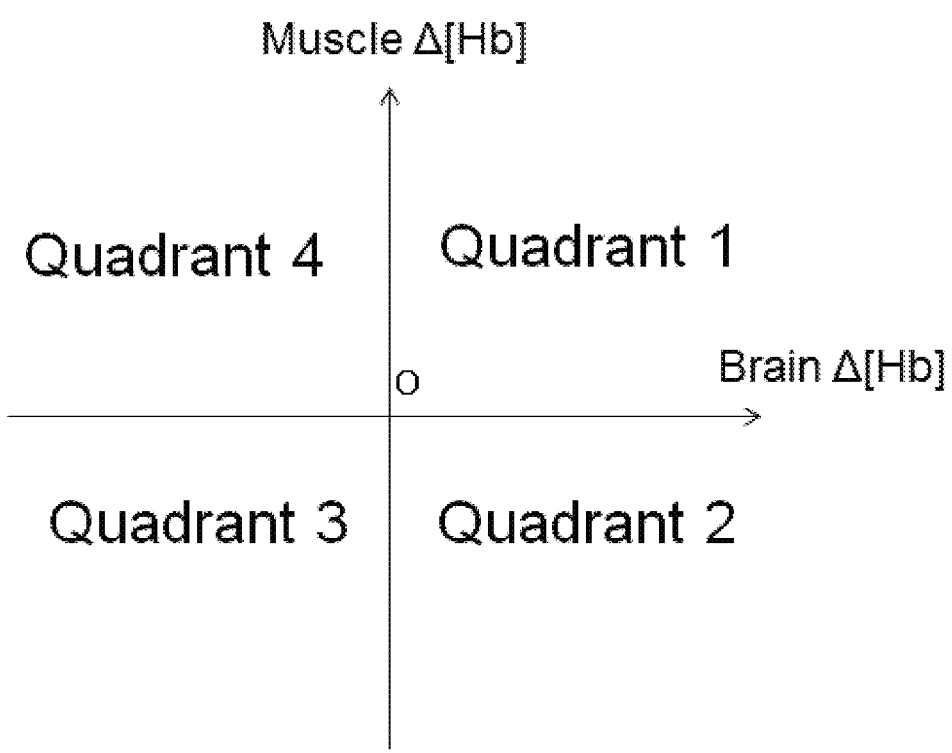
FIG. 11 is a two-dimensional diagram obtained by plotting simultaneous measurements over time, in which the horizontal axis is change in deoxyhemoglobin concentration in the brain ($\Delta[Hb]$; primary motor area M1 of the brain) and the vertical axis is change in deoxyhemoglobin concentration in the muscle ($\Delta[Hb]$; biceps of the arm).

FIG. 11 is a two-dimensional diagram obtained by plotting simultaneous measurements over time, in which the horizontal axis is change in deoxyhemoglobin concentration in the brain ($\Delta[Hb]$; primary motor area M1 of the brain) and the vertical axis is change in deoxyhemoglobin concentration in the muscle ($\Delta[Hb]$; biceps of the arm).

Concentration changes in deoxyhemoglobin in the capillaries of the brain can change, induced by stimulus in response to muscle exercise, can change in the 9 patterns shown below, according to the possible combinations of increase and decrease.

|  | Muscle deoxyhemoglobin $\Delta Hb$ | Brain deoxyhemoglobin $\Delta Hb$ |  |
|---|---|---|---|
| (1) | Increases | Increases | Quadrant 1 |
| (2) | Increases | No change(zero) |  |
| (3) | Increases | Decreases | Quadrant 4 |
| (4) | Decreases | Increases | Quadrant 2 |
| (5) | Decreases | No change(zero) |  |
| (6) | Decreases | Decreases | Quadrant 3 |
| (7) | No change(zero) | Increases |  |
| (8) | No change(zero) | No change(zero) |  |
| (9) | No change(zero) | Decreases |  |

Figure 12:
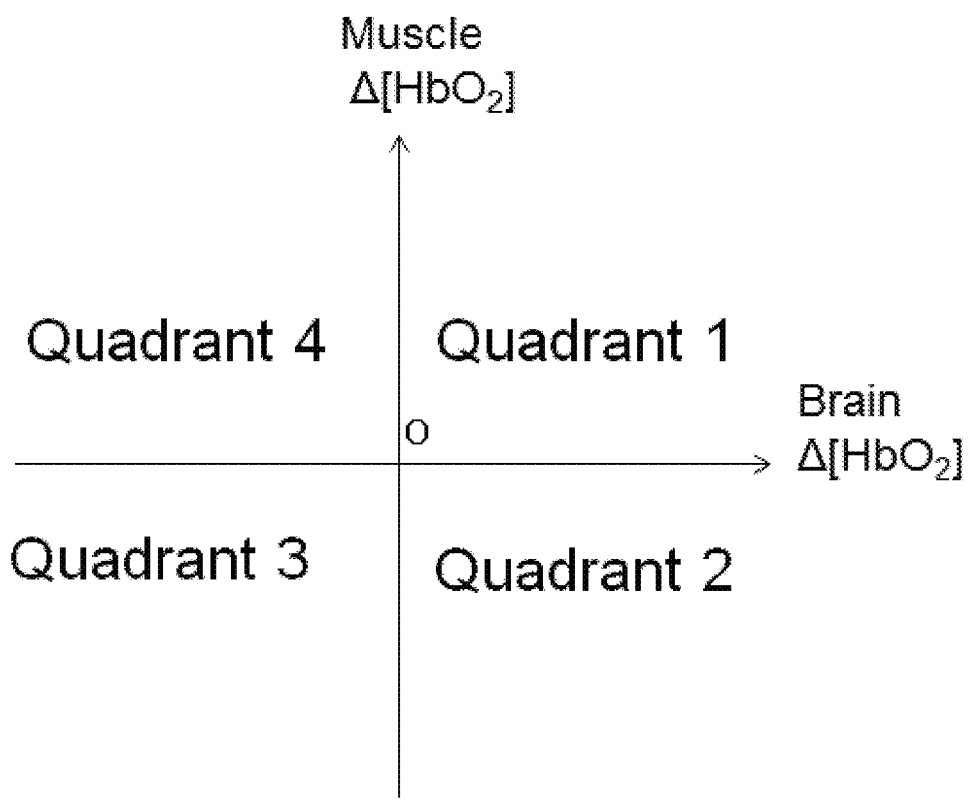
FIG. 12 is a two-dimensional diagram obtained by plotting simultaneous measurements over time, in which the horizontal axis is change in oxyhemoglobin concentration in the brain ($\Delta[HbO_2]$; primary motor area M1 of the brain) and the vertical axis is change in oxyhemoglobin concentration in the muscle ($\Delta[HbO_2]$; upper arm biceps).

FIG. 12 is a two-dimensional diagram obtained by plotting simultaneous measurements over time, in which the horizontal axis is change in oxyhemoglobin concentration in the brain ($\Delta[HbO_2]$; primary motor area M1 of the brain) and the vertical axis is change in oxyhemoglobin concentration in the muscle ($\Delta[HbO_2]$; upper arm biceps).

The ways in which the concentration changes in oxyhemoglobin in the capillaries of the brain can change, induced by stimulus in response to muscle exercise, show the 9 patterns below, according to the possible combinations of their increase and decrease.

|  | Muscle oxyhemoglobin $\Delta HbO_2$ | Brain oxyhemoglobin $\Delta HbO_2$ |  |
|---|---|---|---|
| (1) | Increases | Increases | Quadrant 1 |
| (2) | Increases | No change(zero) |  |
| (3) | Increases | Decreases | Quadrant 4 |
| (4) | Decreases | Increases | Quadrant 2 |
| (5) | Decreases | No change(zero) |  |
| (6) | Decreases | Decreases | Quadrant 3 |
| (7) | No change(zero) | Increases |  |
| (8) | No change(zero) | No change(zero) |  |
| (9) | No change(zero) | Decreases |  |

Figure 13:
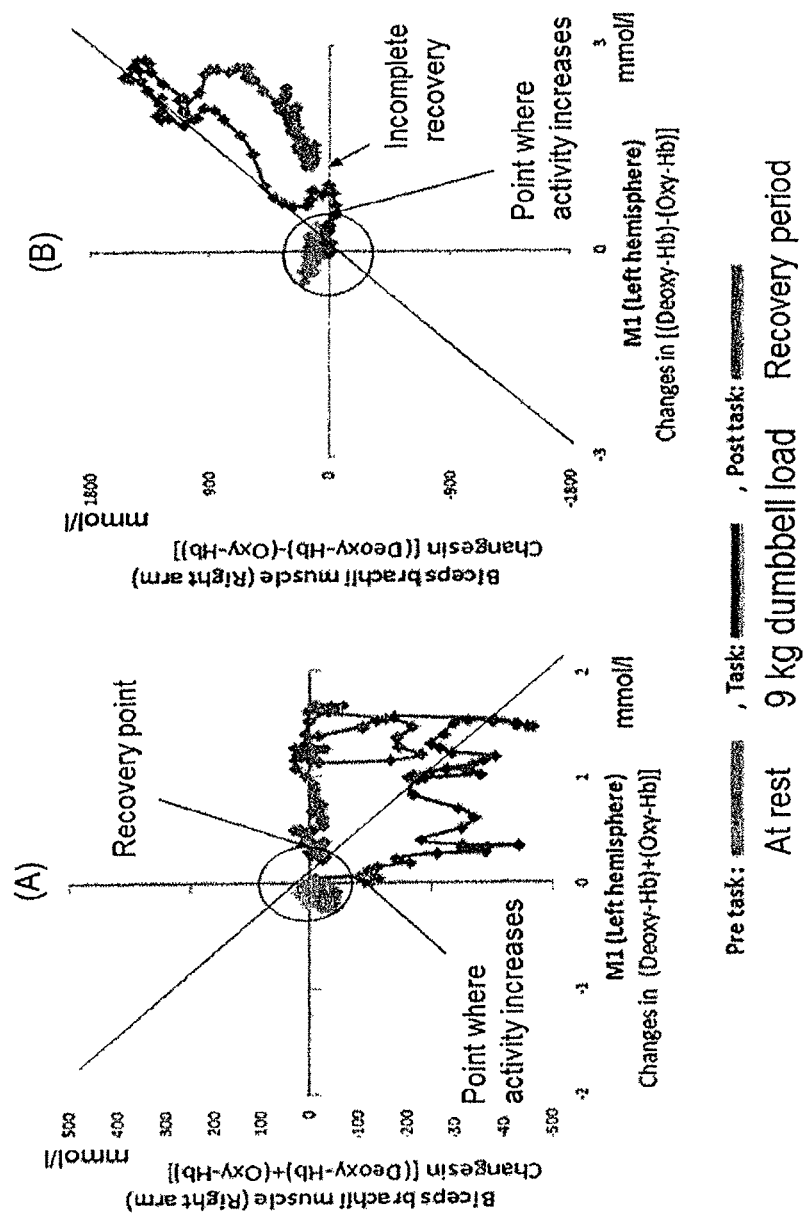
FIGS. 13(A) and (B) are two-dimensional diagrams showing time series changes in blood volume and cerebral oxygen exchange in the brain (left brain primary motor area) and the muscle (right arm biceps) when a subject is given a load-bearing task of lifting a 9 kg dumbbell (at rest, under dumbbell load, and during recovery).

FIGS. 13(A) and (B) are two-dimensional diagrams showing time series changes in blood volume and cerebral oxygen exchange in the brain (left brain primary motor area) and the muscle (right arm biceps) when a subject is given a load-bearing task of lifting a 9 kg dumbbell (at rest, under dumbbell load, and during recovery).

More specifically, FIG. 13(A) is a two-dimensional diagram obtained by plotting simultaneous measurements over time, in which the horizontal axis is change in cerebral blood volume (CBV; $\Delta[Hb]+\Delta[HbO_2]$; left brain primary motor area M1) and the vertical axis is change in muscle blood volume (MBV; $\Delta[Hb]+\Delta[HbO_2]$; right arm biceps).

FIG. 13(B) is a two-dimensional diagram obtained by plotting simultaneous measurements over time, in which the horizontal axis is change in cerebral oxygen exchange (COE; $\Delta[Hb]-\Delta[HbO_2]$; left brain primary motor area M1) and the vertical axis is change in muscle oxygen exchange (MBV; $\Delta Hb-\Delta HbO_2$; right arm biceps).

After the dumbbell load, even though the blood volume is completely recovered (see FIG. 13(A)), the oxygen exchange recovery can be seen to be incomplete (see FIG. 13(B)).

FIG. 14(A)-(F) are two-dimensional diagrams obtained by plotting simultaneous measurements over time, in which the horizontal axis is change in cerebral oxygen exchange (COE; $\Delta[Hb]-\Delta[HbO_2]$; left brain primary motor area M1) and the vertical axis is change in muscle oxygen exchange (MOE; $\Delta[Hb]-\Delta[HbO_2]$; right arm biceps). In the figures, D-O represents $\Delta[Hb]-\Delta[HbO_2]$.

Figure 14:
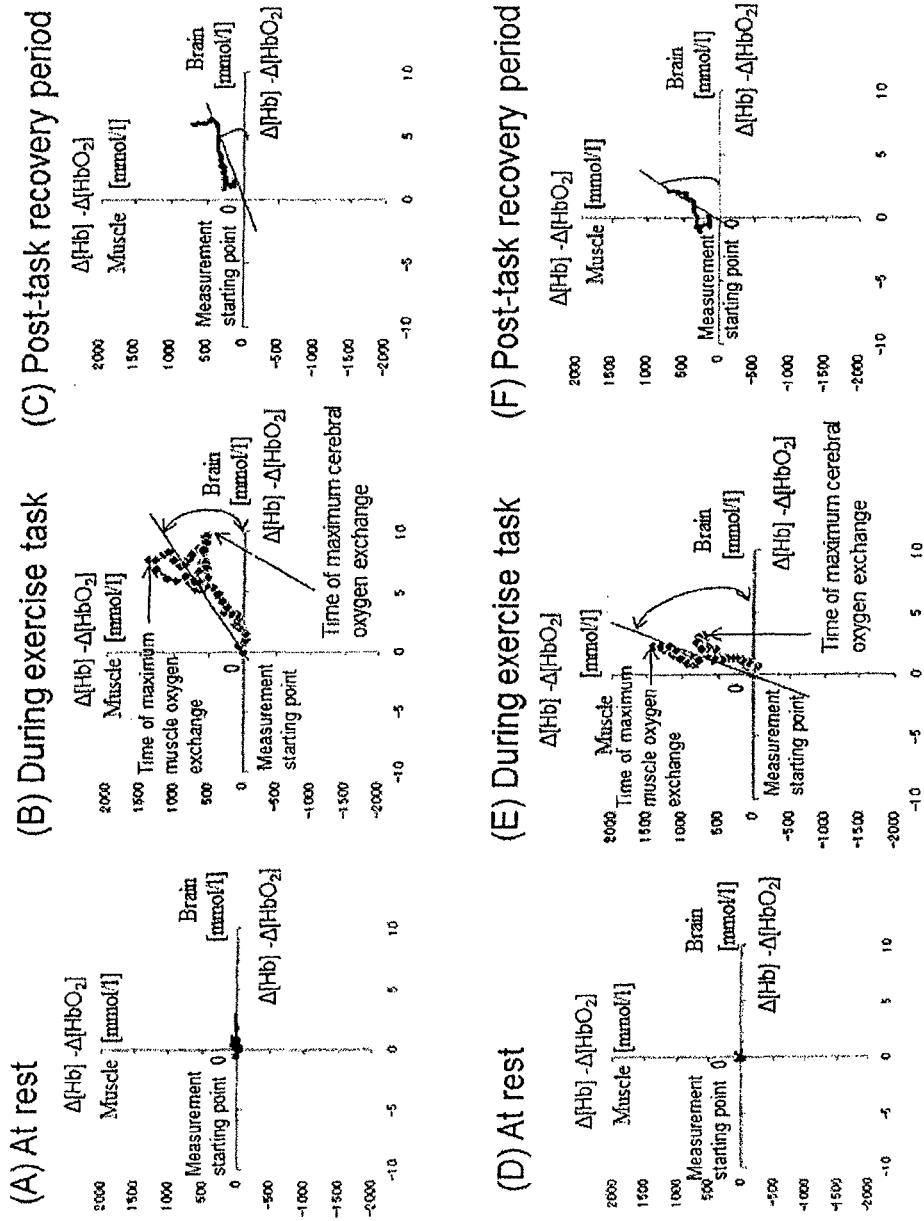
FIG. 14(A)-(F) are two-dimensional diagrams obtained by plotting simultaneous measurements over time, in which the horizontal axis is change in cerebral oxygen exchange (COE; $\Delta[Hb]-\Delta[HbO_2]$; left brain primary motor area M1) and the vertical axis is change in muscle oxygen exchange (MOE; $\Delta[Hb]-\Delta[HbO_2]$; right arm biceps). In the figures, D-O represents $\Delta[Hb]-\Delta[HbO_2]$.

FIG. 14(A) shows a two-dimensional diagram measured during training, during the rest period for the first training exercise; (B), during the exercise task; and (C), during the post-task recovery period. The content of the training was performance of a task of lifting a 14.5 kg dumbbell.

In FIG. 14(A), during the rest period, the values of PL (scalar from the measurement starting point; distance) can be seen to be small; and its maximum value is smaller than that for the PL values shown in FIG. 14(B), during the exercise task.

In the post-task recovery period, shown in 14(C), the coordinates can be seen to be in Quadrant 1, in the same way as during the exercise task, shown in FIG. 14(B), but the average M/B ratio (slope) has decreased, and the oxygen load continues more in the brain than in the muscle after completion of the task.

FIG. 14(D) shows a two-dimensional diagram measured on day 3 after the start of training, during the rest period; (E), during the exercise task; and (F), during the post-task recovery period.

As FIGS. 14(D)-(F) show, the average M/B(1) ratio (slope) has increased and $PL_1$ has become smaller in the results measured on day 3 of training. In the recovery period, the measurements have returned to their values at rest, and the subject has become able to lift a 14.5 dumbbell with much less oxygen consumption in the brain; this can be evaluated as the effect of training.

FIG. 15(A)-(F) are two-dimensional diagrams showing time series changes in blood volume (D+O) and oxygen exchange (D-O) in the brain and the muscle.

Figure 15:
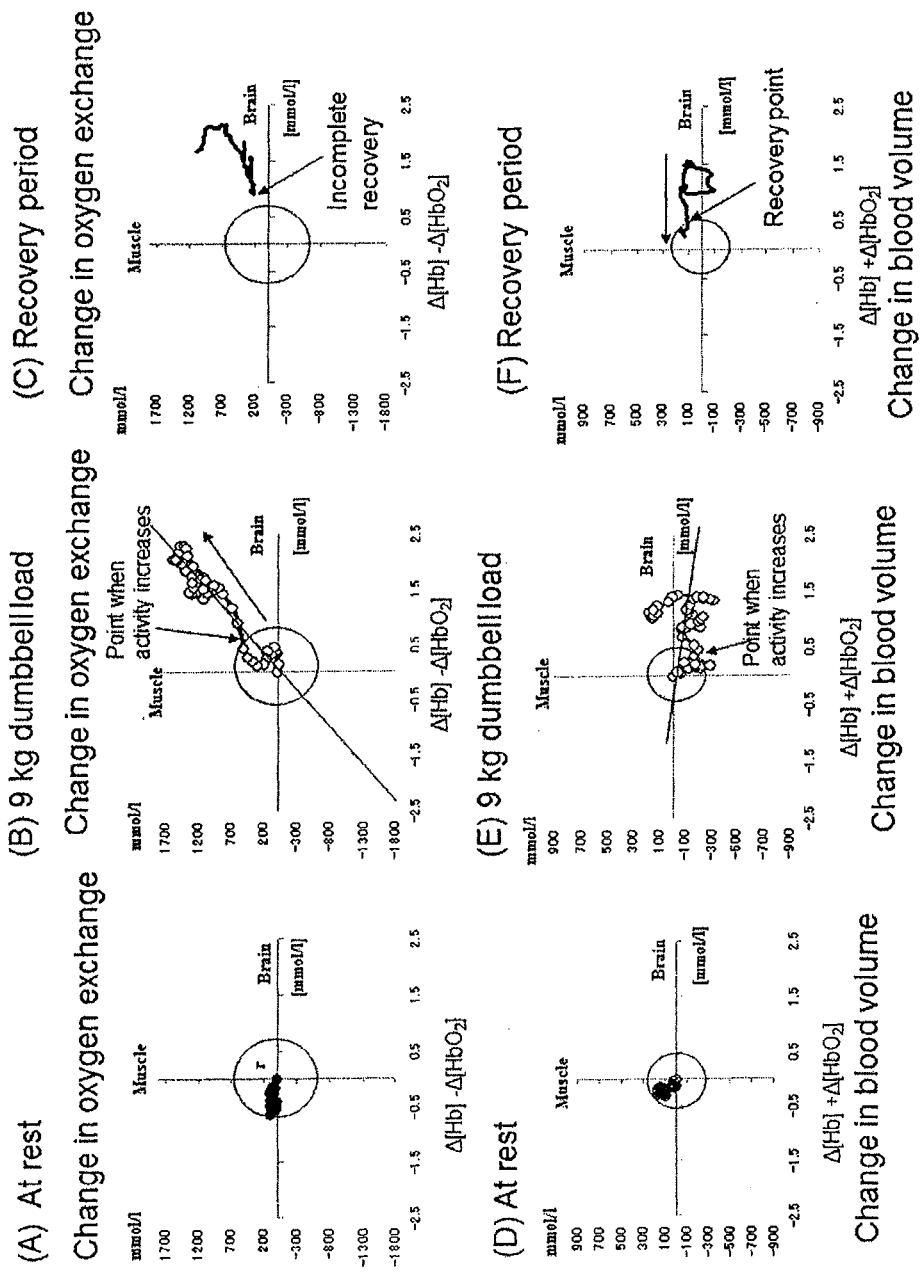
FIG. 15(A)-(F) are two-dimensional diagrams showing time series changes in blood volume (D+O) and oxygen exchange (D-O) in the brain and the muscle.

FIG. 15(A)-(C) are two-dimensional diagrams obtained by plotting simultaneous measurements over time, in which the horizontal axis is change in cerebral oxygen exchange (COE; $\Delta[Hb]-\Delta[HbO_2]$; left brain primary motor area M1), and the vertical axis is change in muscle oxygen exchange (MOE; $\Delta[Hb]-\Delta[HbO_2]$; right arm biceps). In the figures, D-O represents $\Delta[Hb]-\Delta[HbO_2]$.

FIG. 15(A) shows a two-dimensional diagram of a rest period; (B), during a load-bearing task of lifting a 9 kg dumbbell; and (C), a recovery period.

FIG. 15(D)-(F) are two-dimensional diagrams obtained by plotting simultaneous measurements over time, in which the horizontal axis is change in cerebral blood volume (CBV; $\Delta[Hb]+\Delta[HbO_2]$; primary motor area M1 of the brain), and the vertical axis is change in muscle blood volume (MBV; $\Delta[Hb]+\Delta[HbO_2]$; biceps of the arm). In the figures, D+O represents $\Delta[Hb]+\Delta[HbO_2]$.

FIG. 15(D) is a two-dimensional diagram of a rest period; (E), during a load-bearing task of lifting a 9 kg dumbbell; and (F), a recovery period; these correspond respectively to the time series in FIGS. 15(A)-(C).

In FIGS. 15(A) and (D), the resting states of the brain and muscle are plotted as the measurement starting point (origin; 0).

Variation in the trajectory during the rest period is drawn as a circle, with its maximum distance from the origin as the radius r. It possible to tell from whether a trajectory is inside or outside this circle whether it is from during the rest period or during activity or recovery. Time outside the circle is time of increased activity, and recovery can be judged to be incomplete if the trajectory has not come back into the circle even after the dumbbell exercise.

In actuality, comparing FIGS. 15(C) and (F), it can be seen that while changes in blood volume (D+O) have recovered completely, recovery is incomplete for oxygen exchange (D-O).

This shows that the situation of the brain and muscle as regards blood pressure and blood flow have recovered to that at rest; but of the two (brain and muscle), recovery is still incomplete on the brain axis, and even though the dumbbell exercise has stopped, the brain cells are still in a state of excitation.

In addition, FIG. 15(B) shows, from the fact that the trajectories move linearly upwards and to the right, that oxygen exchange is increasing for the brain and muscle during the dumbbell exercise.

FIGS. 15(E) and (F) show the blood flow increasing in the brain but remaining low without change in the muscle, and the blood flow in the muscle quickly recovers after the task as the recovery period.

In this way, by measuring changes in blood volume (D+O) and oxygen exchange (D-O) from the brain and the muscle simultaneously over time during a dumbbell exercise, it is possible, comparing the 2 indices, to evaluate whether the brain is still in the recovery process even after the exercise is stopped. It is possible to see which is likely to recover first, the brain or the muscle; to judge, by watching the trajectories when assigning the next exercise load, whether to start while the recovery is incomplete or after seeing a sufficient recovery, and which recovery time, of the 2 indices, blood volume (D+O) or oxygen exchange (D-O), should be used in starting the next exercise; and thus put together an exercise program.

If a repetition is started when oxygen exchange (D-O) recovery is incomplete, then even with a dumbbell of the same weight, recovery may be delayed and the result may be training with an even stronger load applied to the brain or the muscle. On the other hand, starting after ascertaining recovery from fatigue of the brain and the muscle from the trajectories for blood volume (D+O) and oxygen exchange (D-O) makes it possible to evaluate the length of the recovery period for each exercise. The decision to continue to exercise or not can be made while watching the increasing recovery times as the brain and the muscle gradually become tired.

For example, effectiveness of exercise training can be evaluated by totaling the recovery times for 5 repetitions, or by calculating and displaying each recovery period, and comparing it with that of the next repetition.

Figure 16:
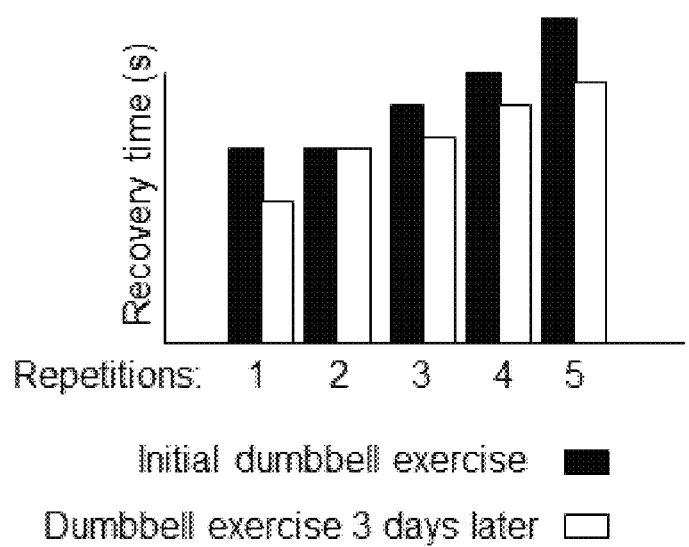
FIG. 16 is a graph showing simultaneous recovery measurements from the brain and the muscle for dumbbell exercises.

FIG. 16 is a graph showing simultaneous recovery measurements from the brain and the muscle for dumbbell exercises.

When trajectories for the brain and the muscle are plotted at rest and "normal" is set by determining their maximum radius, then the effectiveness of exercise training can be evaluated, for example, by totaling the recovery times for 5 repetitions, or calculating and displaying each recovery period, and comparing it with that of the next repetition as shown in FIG. 16. From the above-mentioned recovery times, training can be seen to be having an effect on the recovery periods on day 3, when compared to the first exercise session.

Figure 17:
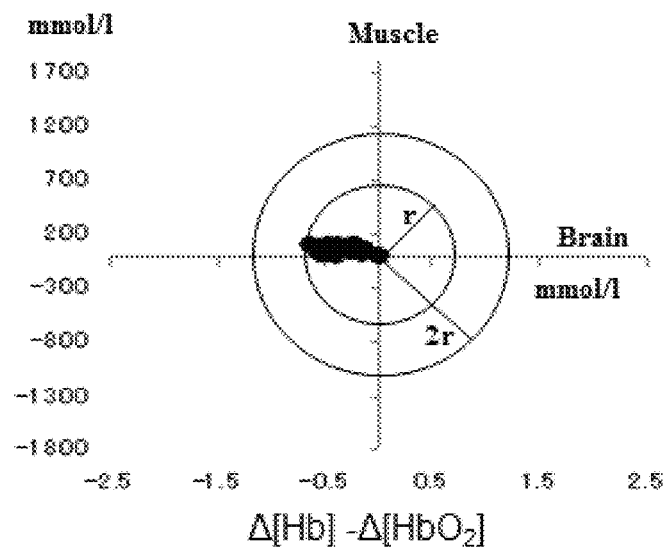
FIG. 17(A) is a two-dimensional diagram showing changes in oxygen exchange (D-O) at rest, and (B) is a two-dimensional diagram showing changes in blood volume (D+O) at rest.
Figure 17:
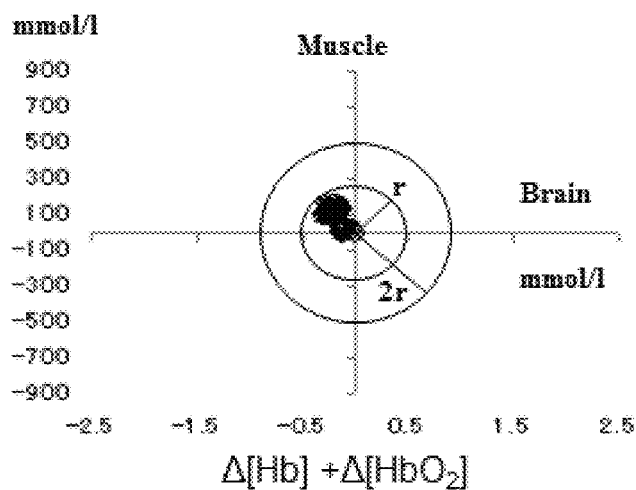

FIG. 17(A) is a two-dimensional diagram showing changes in oxygen exchange (D−O) at rest, and (B) is a two-dimensional diagram showing changes in blood volume (D+O) at rest.

Because recovery after a task may be incomplete, recovery time can also be defined by setting point of recovery as ½ the maximum value of ΔL=r (ΔL/2=r/2), as shown in FIGS. 17(A) and (B).

FIG. 18(A)-(D) are two-dimensional diagrams showing changes in oxygen exchange (D−O) from a plurality of brain sites (B) and from a muscle (M), the upper arm biceps.

Figure 18:
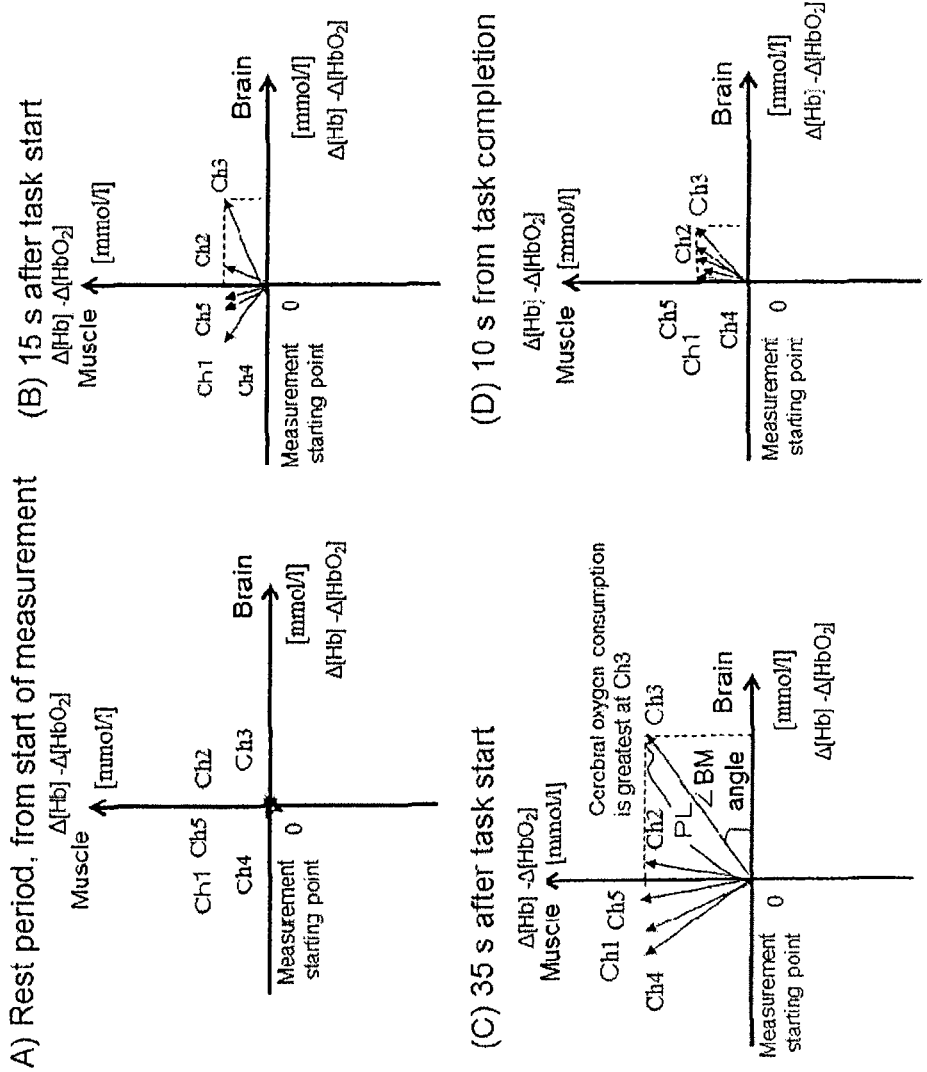
FIG. 18(A)-(D) are two-dimensional diagrams showing changes in oxygen exchange (D-O) from a plurality of brain sites (B) and from a muscle (M), the upper arm biceps.

In the two-dimensional diagrams of FIG. 18, the tracks from channels at a plurality of brain sites (Channels 1-5) are displayed as vectors over time from the measurement starting point.

From FIG. 18, it is possible to evaluate when and at which brain site the most oxygen is used for a given muscle exercise, whether a site has recovered to its state at rest, whether the oxygen consumption load is stronger in the brain or the muscle, and so on, by means of the muscle-to-brain ratios M/B(1) (vector direction) and the scalars from the measurement starting point (power; $PL_1$) on the two-dimensional diagrams.

Namely, if the ratio M/B(1) is constant, then the higher the power value $PL_1$, the greater the effect of the oxygen load applied to the brain and muscle. It depends on the quadrant, but the closer the ratio M/B(1) or the angle M/B is to zero, the greater the load on the brain.

FIG. 19(A)-(D) are two-dimensional diagrams showing changes in blood volume (D+O) at a plurality of brain sites (B) and in a muscle (M), the upper arm biceps.

Figure 19:
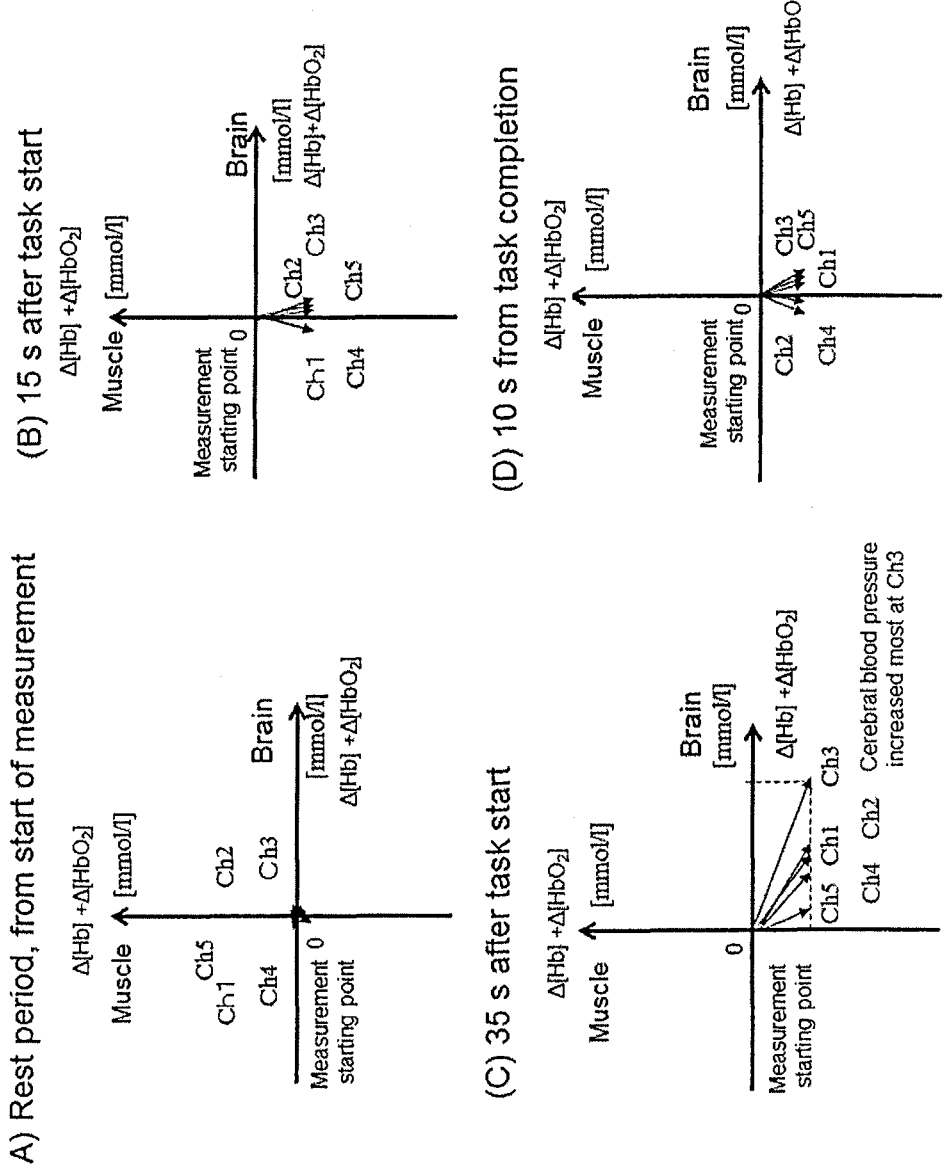
FIG. 19(A)-(D) are two-dimensional diagrams showing changes in blood volume (D+O) at a plurality of brain sites (B) and in a muscle (M), the upper arm biceps.
Figure 20:
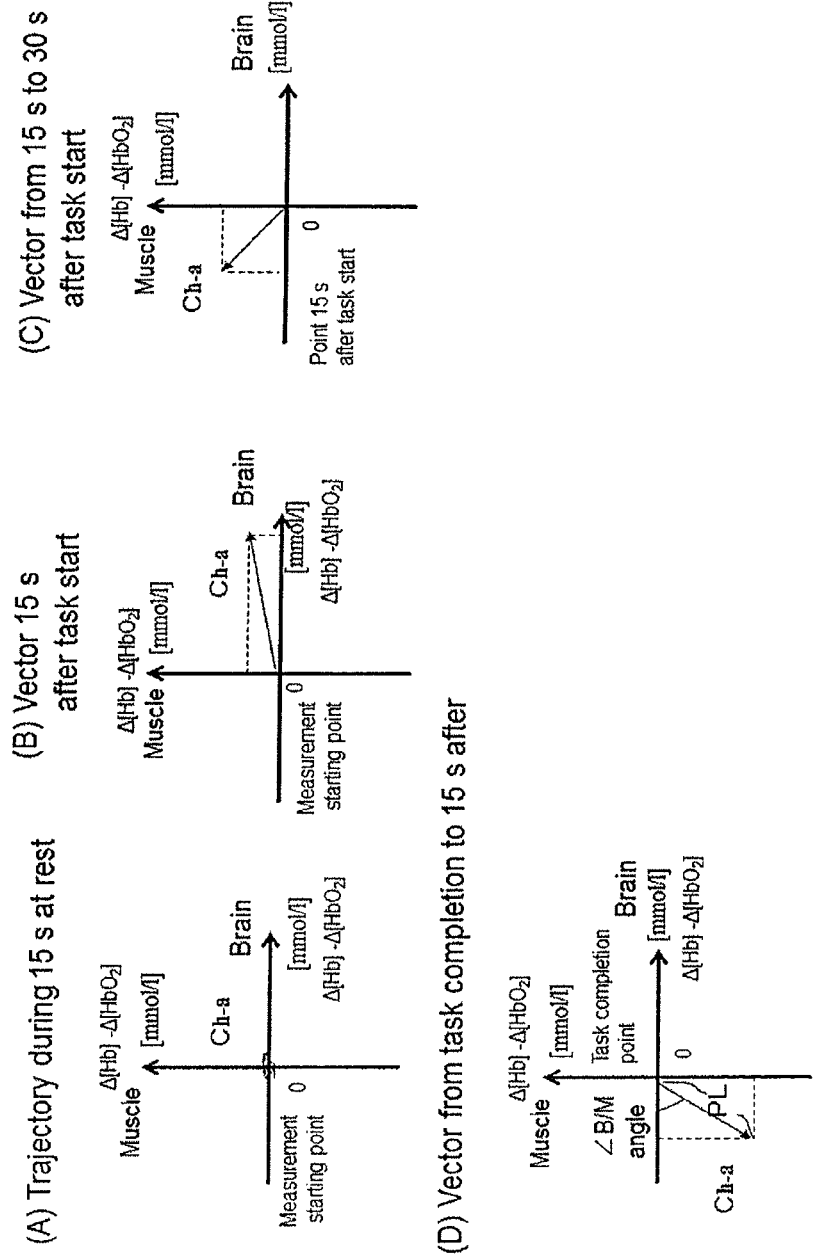
FIG. 20(A)-(D) are two-dimensional diagrams showing changes in oxygen exchange (D-O) from Channel a (Ch-a) of a brain site (B), and from a muscle (M), the upper arm biceps.
Figure 21:
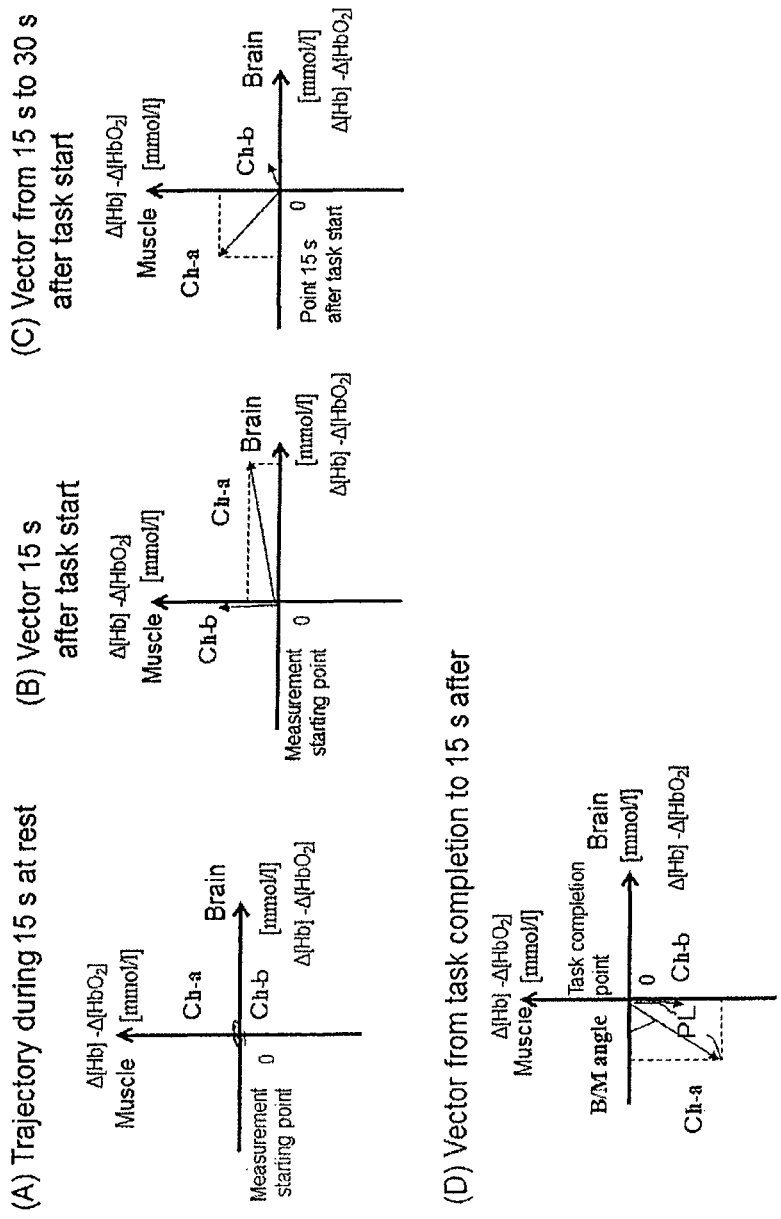
FIG. 21(A)-(D) are two-dimensional diagrams showing changes in oxygen exchange (D-O) from Channel a (Ch-a) and Channel b (Ch-b) of a brain site (B), and from a muscle (M), the upper arm biceps.

In the two-dimensional diagrams of FIG. 19, the tracks from channels at a plurality of brain sites (Channels 1-5) are displayed as vectors over time from the measurement starting point.

From FIG. 19, it is possible to evaluate when and at which brain site the local blood pressure changes the most due to blood volume changes from a given muscle exercise, whether a site has recovered to its state at rest, whether the blood volume change load is stronger in the brain or in the muscle, and so on, by means of the ratios M/B(2) (vector direction) and the scalars from the measurement starting point (power; $PL_2$) on the diagrams.

Here, the muscle-to-brain blood volume load ratio (M/B (2)) is defined as:

Muscle-to-brain blood volume load ratio (*M/B*(2))= [Change in muscle blood volume MBV]/ [Change in cerebral blood volume CBV]    (Equation 21)

Namely, if the ratio M/B(2) is constant, then the greater the power value PL, the greater the blood volume change—namely, the effect of blood pressure—applied to the brain and muscle.

It depends on the quadrant, but the closer the ratio M/B(2) or the angle M/B is to zero, the greater the load is on the brain.

FIG. 20(A)-(D) are two-dimensional diagrams showing changes in oxygen exchange (D−O) from Channel a (Ch-a) of a brain site (B), and from a muscle (M), the upper arm biceps. They are displayed as vectors at intervals of 15 seconds on the two-dimensional diagrams of FIG. 20.

The range of the trajectory at rest (maximum values in each quadrant) can be seen in FIG. 20(A).

In FIG. 20(B), the index D−O due to the task load is displayed as a vector in Quadrant 1; oxygen consumption can be seen to be occurring in the brain and the muscle.

In FIG. 20(C), the vector representation shifts into Quadrant 4 during the task; oxygen consumption in the brain can be seen to be decreasing as oxygen consumption in the muscle increases. In this 15 second period, the load on the brain can be seen to be lightened.

In FIG. 20(D), the vector representation shifts abruptly into Quadrant 3 due to completion of the task; this can be evaluated to mean that oxygen consumption is reduced in both the brain and muscle.

FIG. 21(A)-(D) are two-dimensional diagrams showing changes in oxygen exchange (D−O) from Channel a (Ch-a) and Channel b (Ch-b) of a brain site (B), and from a muscle (M), the upper arm biceps. They are displayed as vectors at intervals of 15 seconds on the two-dimensional diagrams of FIG. 21.

The range of the trajectory at rest (maximum values in each quadrant) can be seen in FIG. 21(A).

In FIG. 21(B), the index D−O from Channel a due to the task load is displayed as a vector in Quadrant 1; oxygen consumption can be seen to be occurring in the brain and the muscle. For Channel b, it is displayed in Quadrant 4; the load on the brain can be seen to be stronger at Channel a, and the load is stronger on the muscle than on the brain at Channel b.

During the task, as shown in FIG. 21(C), at Channel a, the vector representation shifts into Quadrant 4, and oxygen consumption in the brain can be seen to be decreasing as oxygen consumption in the muscle increases. In this 15-second period, the load on the brain is lightened.

On the other hand, at Channel b, the vector representation shifts into Quadrant 1, and oxygen consumption in the muscle can be seen to level out while oxygen consumption in the brain increases.

In FIG. 21(D), the vector representation shifts abruptly into Quadrant 3 due to completion of the task; this can be evaluated to mean that oxygen consumption at Channel a and Channel b is reduced in both the brain and muscle.

Figure 22:
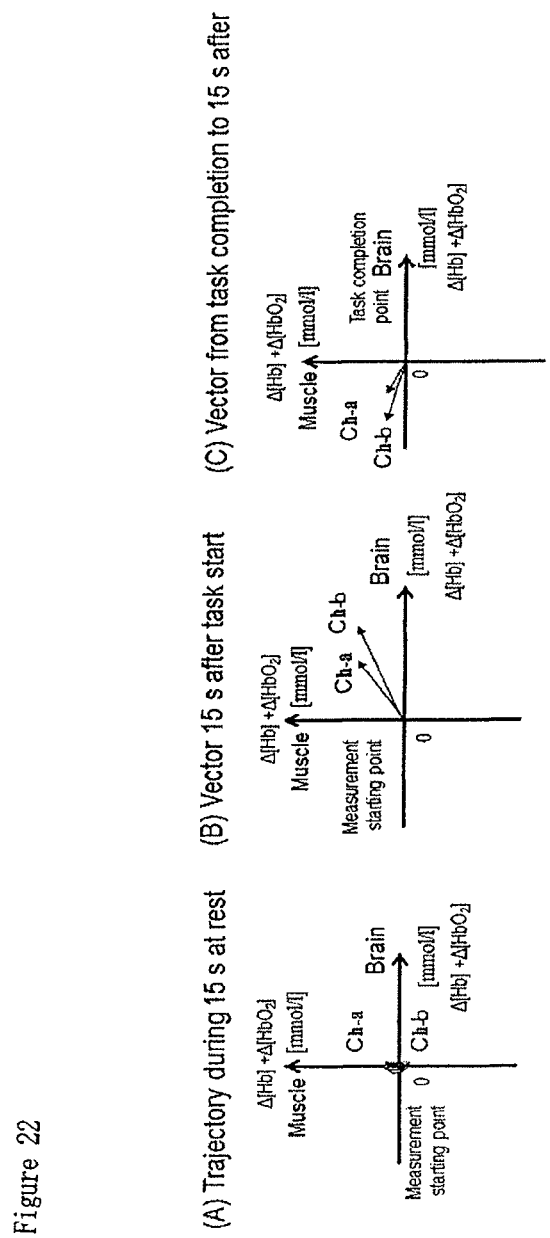
FIG. 22(A)-(C) are two-dimensional diagrams showing changes in blood volume (D+O) from Channel a (Ch-a) and Channel b (Ch-b) of a brain site (B), and from a muscle (M), the upper arm biceps.

FIG. 22(A)-(C) are two-dimensional diagrams showing changes in blood volume (D+O) from Channel a (Ch-a) and Channel b (Ch-b) of a brain site (B), and from a muscle (M), the upper arm biceps. They are displayed as vectors at intervals of 15 seconds on the two-dimensional diagrams of FIG. 22.

The range of the trajectory at rest (maximum values in each quadrant) can be seen in FIG. 22(A).

In FIG. 22(B), the index D+O from Channel a due to the task load is displayed as a vector in Quadrant 1; increases in blood volume can be seen to be occurring in the brain and the muscle. The increase in blood volume to the brain can be seen to be stronger at Channel b than at Channel a.

In FIG. 22(C), the vector representation shifts abruptly into Quadrant 3 at the completion of the task. This can be evaluated to mean that blood volume in the brain decreases, lowering the cerebral blood pressure, but the muscle is swelled up and pumping even more than at the start of the exercise task.

Next, techniques for lessening the problem of non-uniform ROIs when taking NIRS measurements from a plurality of sites are described.

Technique 1 for lessening the problem of non-uniform ROIs (regions of interest) when taking NIRS measurements from a plurality of sites In Technique 1, NIRS signals from the brain, the muscle, and the like can be compared by means of the same quantitative index despite differences in the amounts of change by using a two-dimensional diagram on which $\Delta D$ (changes in deoxyhemoglobin) and $\Delta O$ (changes in oxyhemoglobin) are plotted; trajectories are drawn on the OD plane, and $\Delta Y$ is estimated in the capillaries from $E=(D-O)/(D+O)$, the maximum change in blood volume, and the change in the hematocrit ($\Delta Ht=\Delta BV/BV_0$).

The ratio E (ratio of oxygen exchange to blood volume) is defined as the ratio of oxygen exchange (D–O) to total hemoglobin (D+O).

Measuring changes in oxygen saturation in the capillaries ($\Delta Y$), which are unlikely to be affected by the S/N (signal-to-noise ratio) of the ROI, makes it possible to heighten the accuracy of comparisons between sites.

Figure 23:
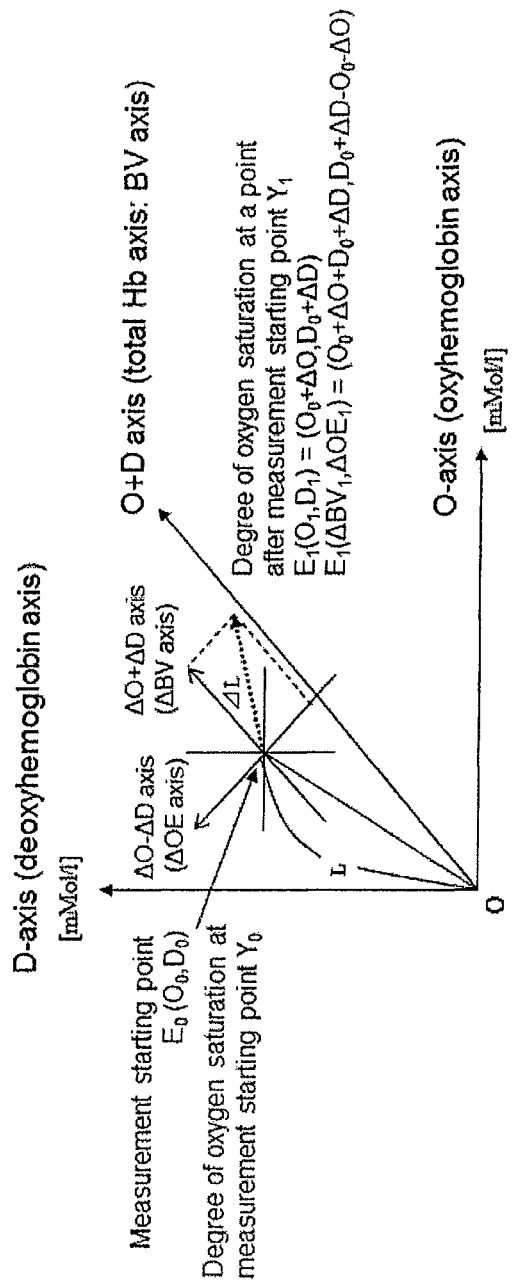
FIG. 23 is a graph illustrating simultaneous measurements of the brain and the muscle utilizing time series data for the ratio E and $\Delta Y$.

FIG. 23 is a graph illustrating simultaneous measurements of the brain and the muscle utilizing time series data for the ratio E and $\Delta Y$.

In FIG. 23, changes in the degree of oxygen saturation ($\Delta Y$) from the start of measurement to a given point in time accompany changes in oxyhemoglobin and changes in deoxyhemoglobin at a ROI. Starting from $E_0$ ($O_0$, $D_0$), changes consequently occur in total hemoglobin (blood volume, $\Delta D+\Delta O$) and oxygen exchange ($\Delta D-\Delta O$).

The inventor accordingly investigated this by defining the ratio E for investigating the relationship between changes in total hemoglobin ($\Delta D+\Delta O$) and changes in oxygen exchange ($\Delta D-\Delta O$). The ratio E (ratio of change in oxygen exchange to change in blood volume) is defined as the ratio of change in oxygen exchange ($\Delta D-\Delta O$) to change in total hemoglobin ($\Delta D+\Delta O$).

$$\text{Ratio } E=(\Delta D\Delta O)/(\Delta D+\Delta O)=(k-1)/(k+1) \qquad \text{(Equation 22)}$$

where $k=\Delta D/\Delta O$

Previously, even with equidistantly spaced emitter and receptor probes, because the distances to the cerebral parenchyma measured from the scalp are not constant, the amounts of hemoglobin (light intensity) from different ROIs (regions of interest) were different The amounts of oxyhemoglobin (O) and deoxyhemoglobin (D) are [measured] values obtained from a ROI.

$$K=D/O \qquad \text{(Equation 23)}$$

Figure 33:
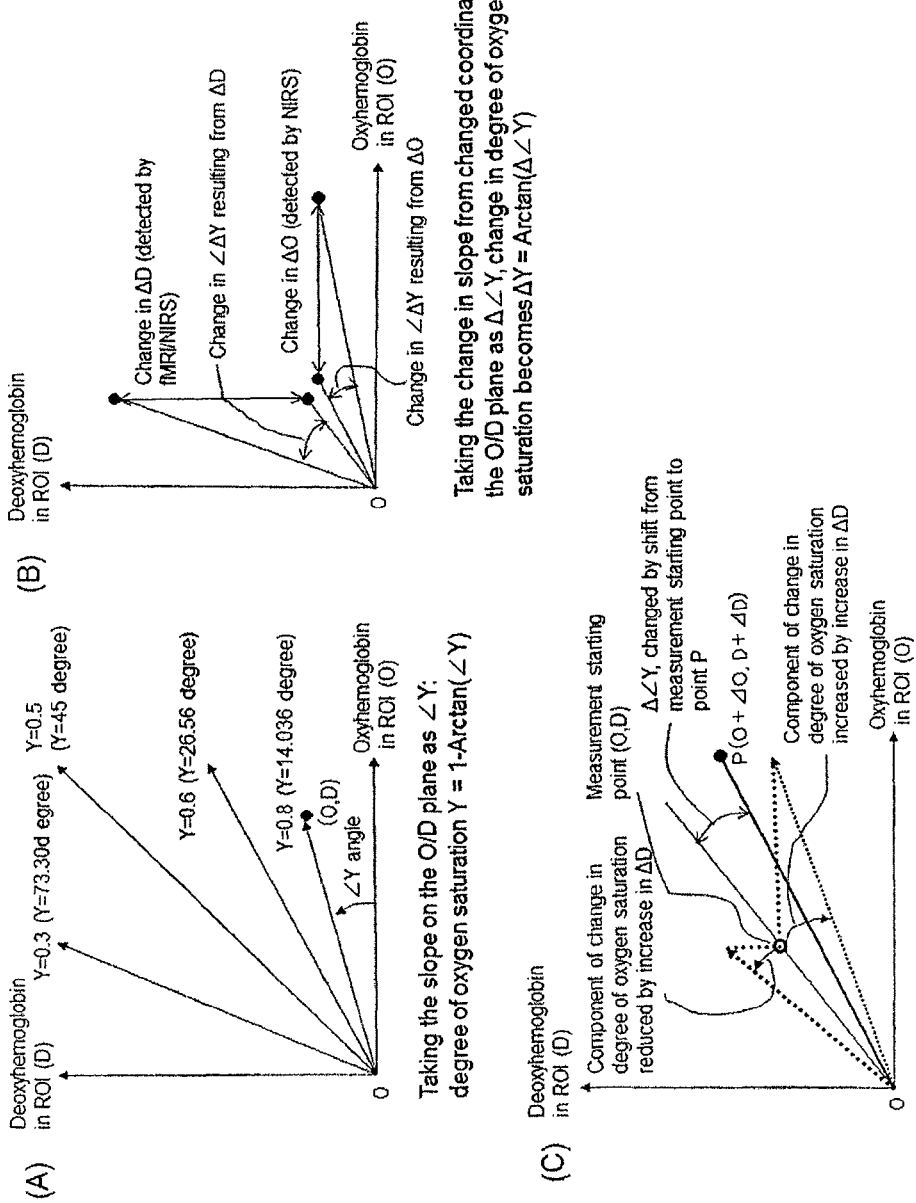
FIG. 33(A) is a graph with amounts of oxyhemoglobin (O) in a ROI as the horizontal axis and amounts of deoxyhemoglobin (D) in the ROI as the vertical axis, showing their relationship with degree of oxygen saturation Y; and (B) is a graph showing the relationships between change in oxyhemoglobin in the ROI (ΔO), change in deoxyhemoglobin in the ROI (ΔD), and change in the angle Y (ΔY). (C) is a graph showing that because changes in the degree of oxygen saturation occur depending on both changes in oxyhemoglobin (ΔO) and changes in deoxyhemoglobin (ΔD) in the ROI, [viewing them] separately may result in an erroneous evaluation, with opposite results.

K is the slope on the OD plane shown in FIG. 33.

As for the units of the ratio K, it is a ratio of concentrations at a ROI, and even if there are a plurality of ROIs and their sizes are different, it is a parameter that can be compared between them, calculated simultaneously and so on. Of the various NIRS measurement methods, TRS (time-resolved spectroscopy) is used to measure amounts of oxyhemoglobin (O) and deoxyhemoglobin (D) in a ROI.

The blood volume (BV) of a ROI measured by one pair of emitter and receptor probes approximates the amount of total hemoglobin, if the blood serum component is excluded.

It can consequently be expressed as the sum of the amounts of oxyhemoglobin (O) and deoxyhemoglobin (D):

$$BV=D+O \qquad \text{(Equation 24)}$$

As for the difference between the amounts of oxyhemoglobin and deoxyhemoglobin concentrations of a ROI, it can be stated that:

$$OE=D-O \qquad \text{(Equation 25)}$$

Accordingly, the ratio E between the difference and the sum of the concentrations of oxyhemoglobin and deoxyhemoglobin at the ROI is newly defined as:

$$E = (D - O)/(D + O) \qquad \text{(Equation 26)}$$
$$= OE/BV$$

As for the units for the ratio E, because, like the ratio K, it is a ratio of concentrations at a ROI, even if there are a plurality of ROIs and their sizes are different, it is a parameter that can be compared between them, calculated simultaneously and so on.

It can be seen from Equations 26 and 23 that E can be expressed as a function of K:

$$E=(K-1)/(K+1) \qquad \text{(Equation 27)}$$

If the degree of oxygen saturation of the ROI is taken to be Y (where $0 \leq Y \leq 1$), then because $$Y=O/(O+D) \qquad \text{(Equation 28)}$$

and $$1-Y=D/(O+D), \qquad \text{(Equation 29)}$$

it follows that from Equations 23, 28, and 29, Y can be expressed as a function of K:

$$Y=1/(1+K) \qquad \text{(Equation 30)}$$

$$1-Y=K/(1+K), \qquad \text{(Equation 31)}$$

and from Equations 26, 28, and 29, E can be expressed as a function of Y:

$$E=1-2Y \qquad \text{(Equation 32)}$$

namely, $$Y=(1-E)/2 \qquad \text{(Equation 33)}$$

By this means, the degree of oxygen saturation Y is obtained by means of the ratio E between amounts of oxyhemoglobin (O) and deoxyhemoglobin (D), which are obtained by NIRS measurement.

This Y can be regarded as oxygen concentration in the capillaries of a ROI.

This means that a plurality of sets of measurements can be used to obtain a plurality of Y time series, independently of the size of a ROI.

The change in degree of oxygen saturation ($\Delta Y$) is determined from the degree of oxygen saturation at the measurement starting point ($Y_0$) to the degree of oxygen saturation at a point after the measurement starting point ($Y_1$):

Because E is a linear function of Y, [$\Delta Y$] can be determined as follows:

$$\Delta Y = [(1 - E_1)/2] - [(1 - E_0)/2] \qquad \text{(Equation 34)}$$
$$= (E_0 - E_1)/2$$
$$= \Delta E/2$$

$$= (-1/2)[\Delta OE/(BV_0 + \Delta BV)] + \quad \text{(Equation 10)}$$

$$(E_0/2)[\Delta BV/(BV_0 + \Delta BV)]$$

If the change in degree of oxygen saturation at a ROI is taken to be $\Delta Y$ (where $-1 \leq \Delta Y \leq 1$), then there are 4 possibilities for Equation 34: A, B, C or D as described below. Here, (A) If $\Delta BV=0$, [$\Delta Y$] changes parallel to the D–O axis on the O/D two-dimensional plane:

$$\Delta Y = (-1/2)(\Delta OE/BV_0) \quad \text{(Equation 10a)}$$

$\Delta Y$ has the shape of the line $\Delta OE$.

It is calculated from changes in oxyhemoglobin and deoxyhemoglobin obtained from NIRS measurements.

In addition, it can be understood from this equation that $\Delta OE$ fluctuates more than $\Delta BV$ at rest.

If the ROI at rest=$BV_0$, then $\Delta Y$ will appear to be changing, depending on how the probes are placed.

Figure 24:
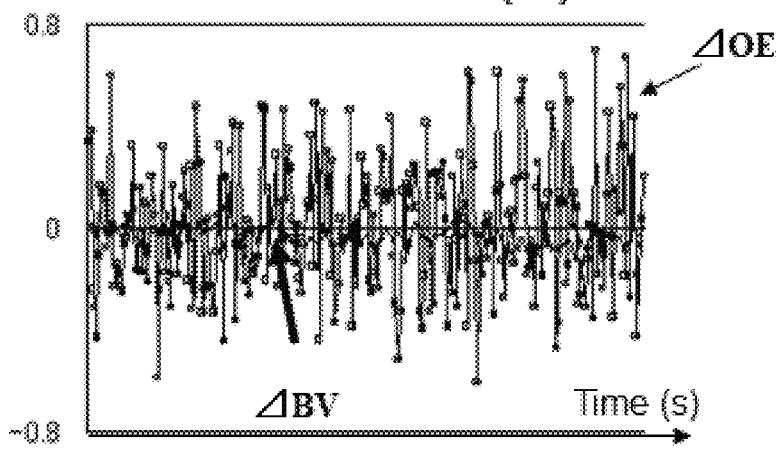
FIGS. 24(A) and (B) are graphs showing changes in the time series of $\Delta OE$ and $\Delta BV$ at rest.
Figure 24:
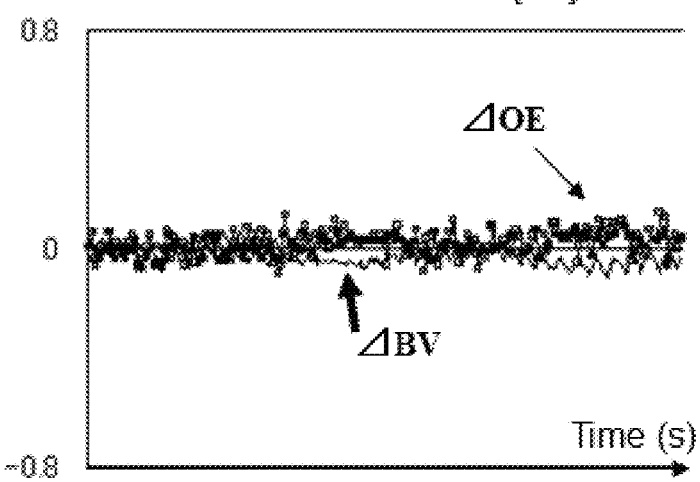

FIGS. 24(A) and (B) are graphs showing changes in the time series of $\Delta OE$ and $\Delta BV$ at rest.

In the data shown in FIG. 24(A), the ratio between the standard deviations of $\Delta BV$ and $\Delta OE$ at rest is 8.1, and in (B), the ratio between the standard deviations of $\Delta BV$ and $\Delta OE$ at rest is 1.2.

When the ratio between standard deviations is 2.0 or more, this means that because there is little Hb at the ROI and not enough light is captured, the site can be judged to have a bad S/N ratio. Namely, uniform ROIs for a plurality of measurement sites can be maintained by setting up the probes in such a way that maintains standard deviation ratios for $\Delta OE$ and $\Delta BV$ of 2 or less.

In this case, if the change in the degree of oxygen saturation at a ROI is taken to be $\Delta Y$ (where $-1 \leq \Delta Y \leq 1$), then:

$$\Delta Y = (-1/2)[\Delta OE/(BV_0+\Delta BV)]+(E_0/2)[\Delta BV/(BV_0+\Delta BV)]$$

(B) If $\Delta OE=0$ ($\Delta D=\Delta O$), [$\Delta Y$] changes parallel to the D+O axis on the O/D two-dimensional plane:

$$\Delta Y = (E_0/2)[\Delta BV/(BV_0 + \Delta BV)] \quad \text{(Equation 35)}$$

$$= E_0 \Delta O/(2\Delta O + BV_0) \quad \text{(Equation 36)}$$

$$= E_0 \Delta D/(2\Delta D + BV_0) \quad \text{(Equation 37)}$$

Namely, $\Delta Y$ changes by changing parallel to the O+D axis. $\Delta Y$ is an inverse function of $\Delta D$ or $\Delta O$.

Because $BV_0$ can be thought of as the measurement target ROI, time series changes in $\Delta Y$ from the measurement starting point will change depending on $\Delta O$ or $\Delta D$, as shown in FIG. 33(B).

Namely, the time series changes can be understood by substituting an arbitrary number for $BV_0$.

(C) If neither $\Delta BV$ nor $\Delta OE$ is 0 (zero), $\Delta Y$ is determined by assigning hypothetical values to O and D during measurement. Namely, time series changes can be understood by substituting an arbitrary number for $BV_0$.

$$\Delta Y = (-1/2)[\Delta OE/(BV_0+\Delta BV)]+(E_0/2)[\Delta BV/(BV_0+\Delta BV)]$$

(D) If $\Delta Y=0$, then $$E_0 = E_1 = \Delta OE/\Delta BV$$

Here, the relationship between $BV_0$ and $\Delta BV$ in $\Delta Y$ from Equation 34 is represented by Equation 38:

$$\Delta Ht(\Delta O+\Delta D)/(O+D)=\Delta BV/BV_0 \quad \text{(Equation 38)}$$

Ht is the blood volume in the ROI, namely, the hematocrit; and $\Delta Ht$ represents change in hematocrit. The hematocrit in the arteries and veins is normally from 0.4 to 0.45. In the capillaries, as the ROI becomes smaller, its range changes to from 0.2 to 0.8.

Namely, maximum $\Delta Hb$ may have a value of from 0.25 to 4.

A method is proposed here whereby, even without knowing the optical path length (PL) by means of the CW (continuous wave) method, time series data for $\Delta Y$ can be provisionally calculated by the use of a method in which the change in hematocrit $\Delta Ht$ is provisionally assigned from the maximum value of $\Delta BV$ ($\Delta BV_{max}$) according to Equation 38.

The fact that a response of the brain or muscle, etc., is present when a ROI's hematocrit decreases and $\Delta BV$ decreases can be explained from Equation 38.

The following equation is used for estimation:

Maximum $\Delta Ht$ ($\Delta Ht_{max}$)=(signal intensity of maximum change in $\Delta BV$)/(BV signal intensity in the ROI) (Equation 39)

In this case, the "BV signal intensity in the ROI" can be calculated by substituting an arbitrary number selected from within the range between $-1$ and 1 for maximum $\Delta Ht$ in the equation.

Figure 25:
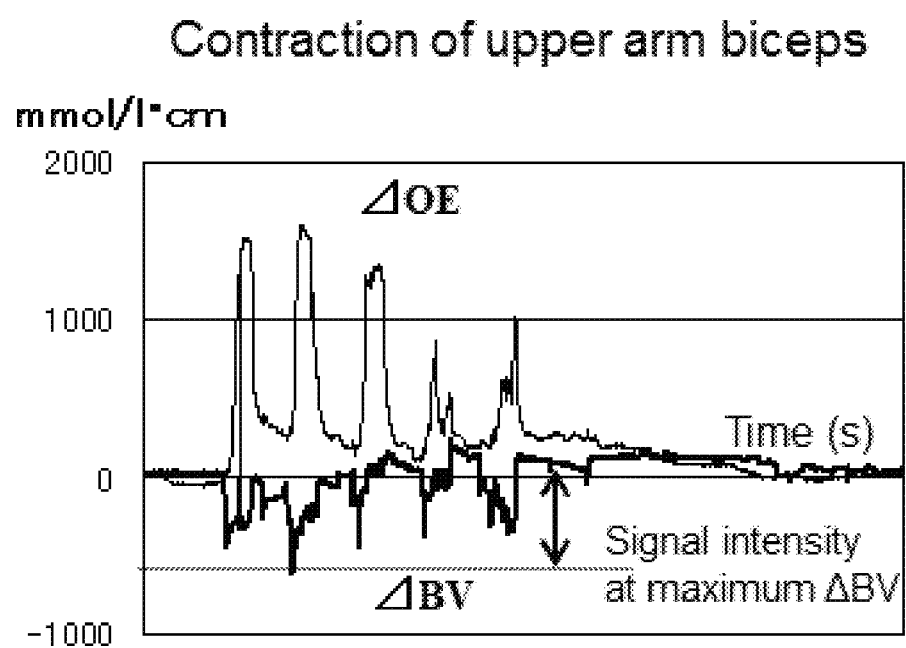
FIG. 25 is a graph showing time series changes in $\Delta OE$ and $\Delta BV$ when the upper arm biceps is contracted.

FIG. 25 is a graph showing time series changes in $\Delta OE$ and $\Delta BV$ when the upper arm biceps is contracted.

As assumption 1, $Y_0=0.7$, and $E_0=-0.4$

As assumption 2, if change in hematocrit is taken to be $=-0.25$, then the following is obtained from Equation 39:

(BV signal intensity in the ROI)=(signal intensity of maximum change in $\Delta BV$)/($-0.25$)

From the above, Equation 35 becomes:

$$\Delta Y=-3e/14+0.6/7$$

$$e=\Delta OE/\Delta BV$$

$Y_0$ is taken to be:

$Y_0=0.5$ (when degree of oxygen saturation is 50%)

(Degree of oxygen saturation in the capillaries is provisionally estimated to be around 50-60%)

$D=0$, $E_0=0$

From Equations 34 and 38, the equation $$\Delta Y=(-1/2)[\Delta OE/(BV_0+\Delta BV)]+(E_0/2)[\Delta BV/(BV_0+\Delta BV)]$$

becomes:

(Equation 40)
$$\Delta Y = (E_0 - E_1)/2 = -\Delta E_1/2 = -(\Delta OE/\Delta BV)[1/(\Delta Ht + 1)]$$
$$= -e[1/(\Delta Ht + 1)]$$

A method is proposed here whereby, even without knowing the optical path length (PL), time series data for $\Delta Y$ can be calculated by the use of a model in which the change in hematocrit $\Delta Ht$ is estimated from the maximum value of $\Delta BV$:

ΔHt=(measured absolute value of maximum ΔBV)/
BV

BV=(measured absolute value of maximum ΔBV)/Ht  (Equation 41)

In the capillaries, as the ROI becomes smaller, it changes from 0.2 to 0.8; namely, ΔHt may have a value of from around −4 to 4.

Consequently, taking the measurement starting point in Equation 26 as $Y_0$=0.5, ΔY can be seen to change as a function of e and ΔHt.

Figure 26:
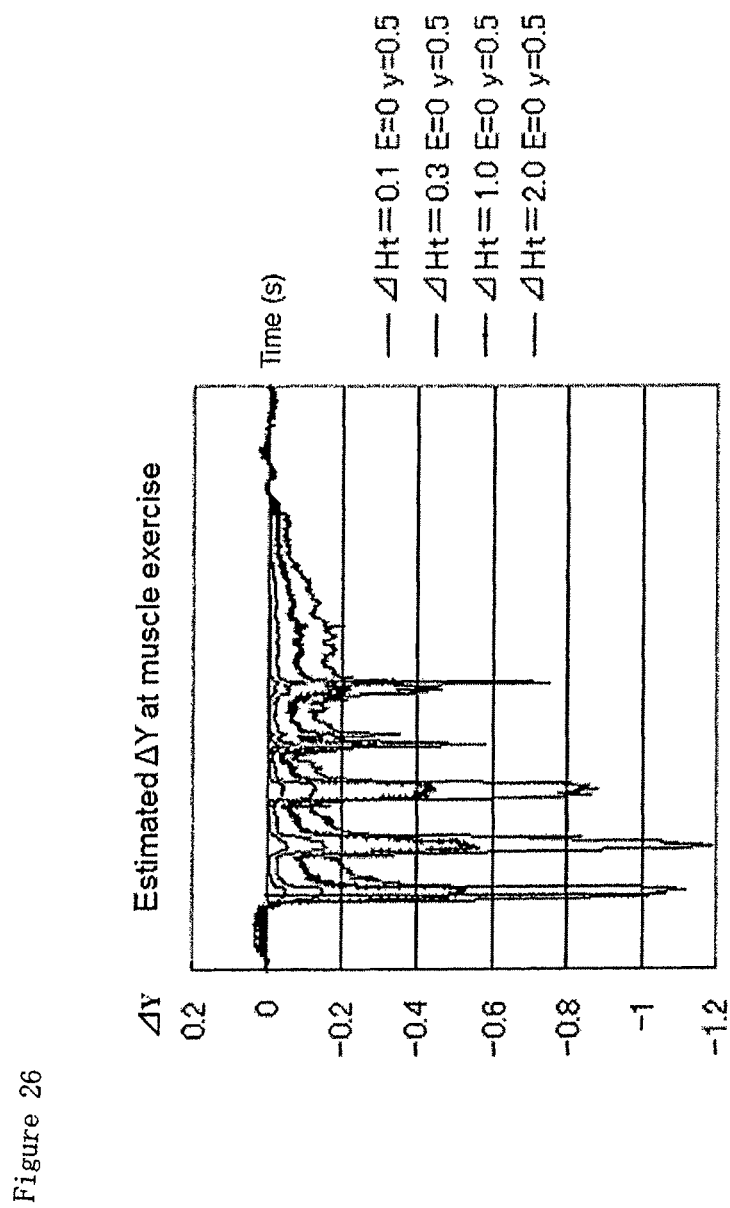
FIG. 26 is a graph showing time series changes in estimated $\Delta Y$ in a muscle exercise, calculated with constant values for E and Y; the horizontal axis is time (s) and the vertical axis is $\Delta Y$.

FIG. 26 is a graph showing time series changes in estimated ΔY in a muscle exercise, calculated with constant values for E and Y; the horizontal axis is time (s) and the vertical axis is ΔY.

It can be seen from FIG. 26 that the hematocrit ratio has a big effect on ΔY. This result suggests that the capillaries are responding to sudden changes in oxygen concentration by changing the number of blood cells.

On the other hand, a hypothetical ΔHt=2 gives ΔY=−1.2, an impossible value.

Namely, this estimation model can also be used to estimate an upper limit to the range of variation of ΔHt.

Figure 27:
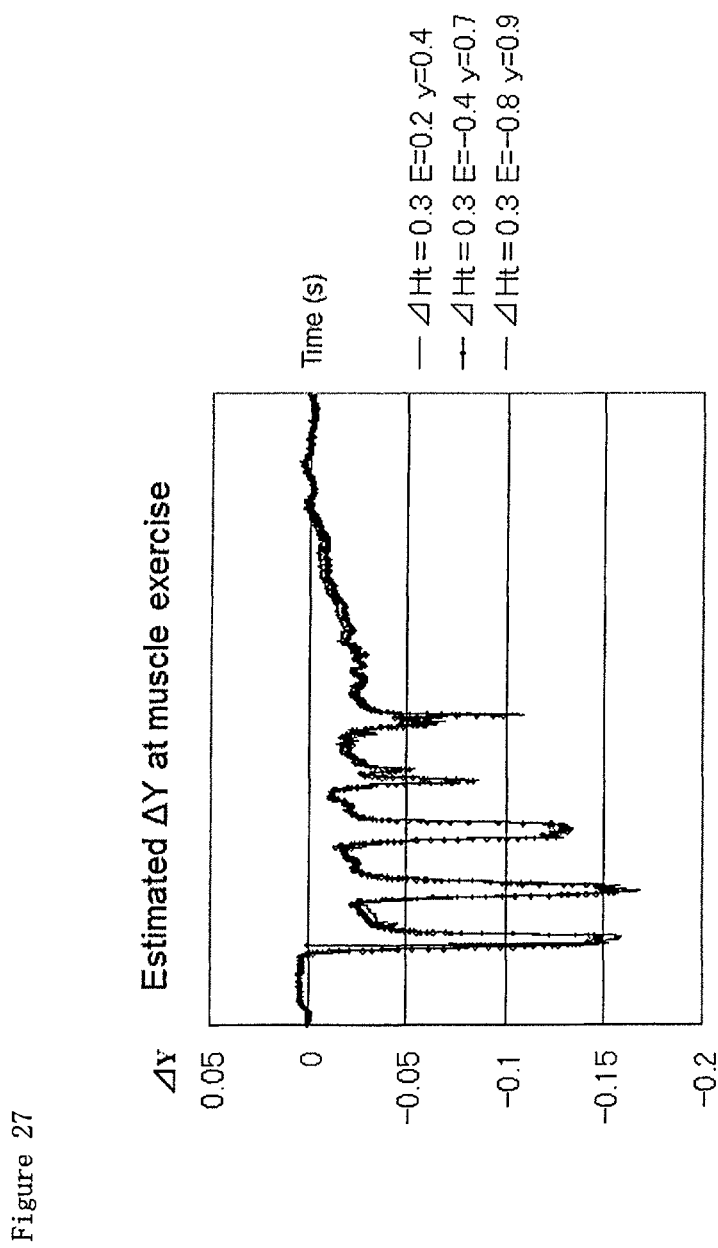
FIG. 27 is a graph showing time series changes in estimated $\Delta Y$ in a muscle exercise calculated with a constant hematocrit; the horizontal axis is time (s) and the vertical axis is $\Delta Y$.

FIG. 27 is a graph showing time series changes in estimated ΔY in a muscle exercise calculated with a constant hematocrit; the horizontal axis is time (s) and the vertical axis is ΔY.

It can be seen from FIG. 27 that when the hematocrit ratio is constant, the value of Y at the start of measurement does not have much effect on ΔY.

This result suggests that the capillaries are responding to sudden changes in oxygen concentration by changing the number of blood cells.

This shows that a simplified calculation is possible, taking E=0 and Y=0.5.

Namely, Equation 10 becomes the following approximate equation:

$$\Delta Y = (-1/2)[\Delta OE/(BV_0 + \Delta BV)] + \quad \text{(Equation 11)}$$
$$[E_0/2)(\Delta BV/(BV_0 + \Delta BV)]$$
$$\approx (-1/2)[\Delta OE/(BV_0 + \Delta BV)]$$

Figure 28:
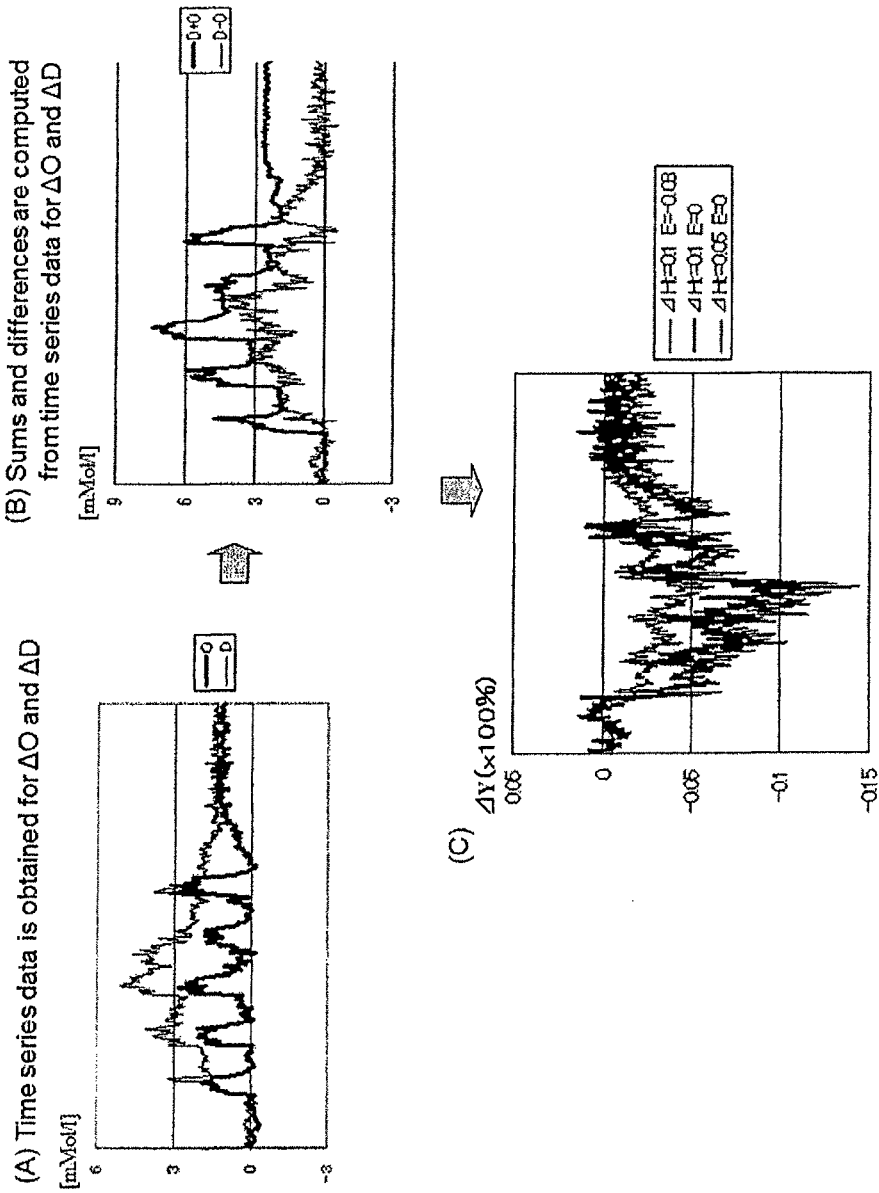
FIG. 28(A)-(C) are graphs illustrating steps for calculating $\Delta Y$ from $\Delta O$ and $\Delta D$ obtained by measuring the brain.

FIG. 28(A)-(C) are graphs illustrating steps for calculating ΔY from ΔO and ΔD obtained by measuring the brain.

First, ΔO and ΔD time series data are obtained from measurements from the brain (see FIG. 28(A)).

Next, sums and differences are calculated from the ΔO and ΔD time series data (see FIG. 28(B)).

These are then inserted in the equation for ΔY, and ΔY is calculated (see FIG. 28(C)).

E is calculated from Y at the start of measurement, with an estimated value for ΔHt.

It is influenced by ΔHt, but because the influence of ΔHt on E at the start is small, it can almost always be ignored except for detecting minute changes.

It is clear that ΔY clearly shows different time series data from that of ΔO and ΔD (above), thus providing new information.

Figure 29:
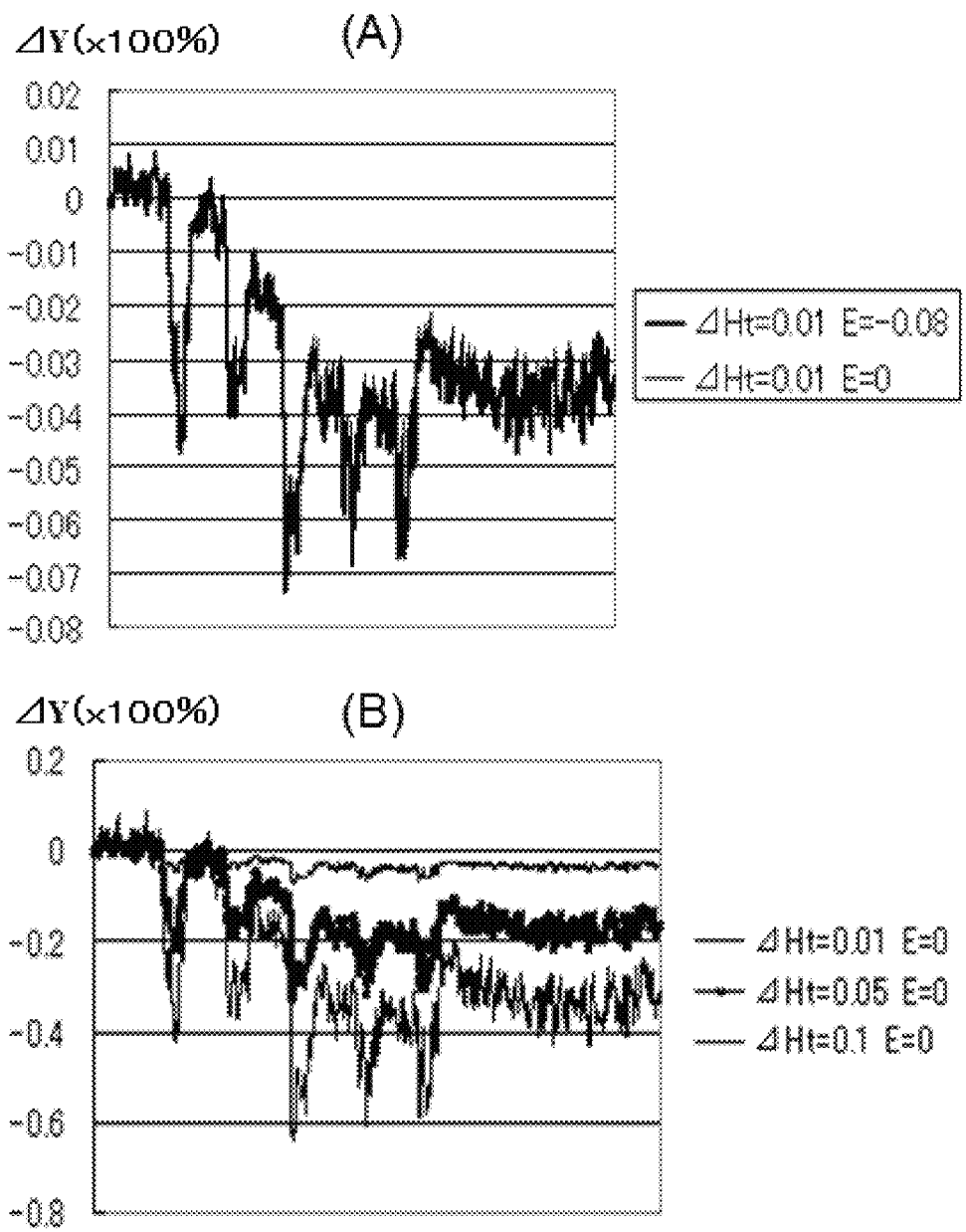
FIG. 29(A) is a graph of estimated $\Delta Y$ under 2 sets of conditions, showing the effect of E; (B) is a graph of estimated $\Delta Y$ under 3 sets of conditions, showing the effect of $\Delta Ht$.

FIG. 29(A) is a graph of estimated ΔY under 2 sets of conditions, showing the effect of E; (B) is a graph of estimated ΔY under 3 sets of conditions, showing the effect of ΔHt.

Figure 30:
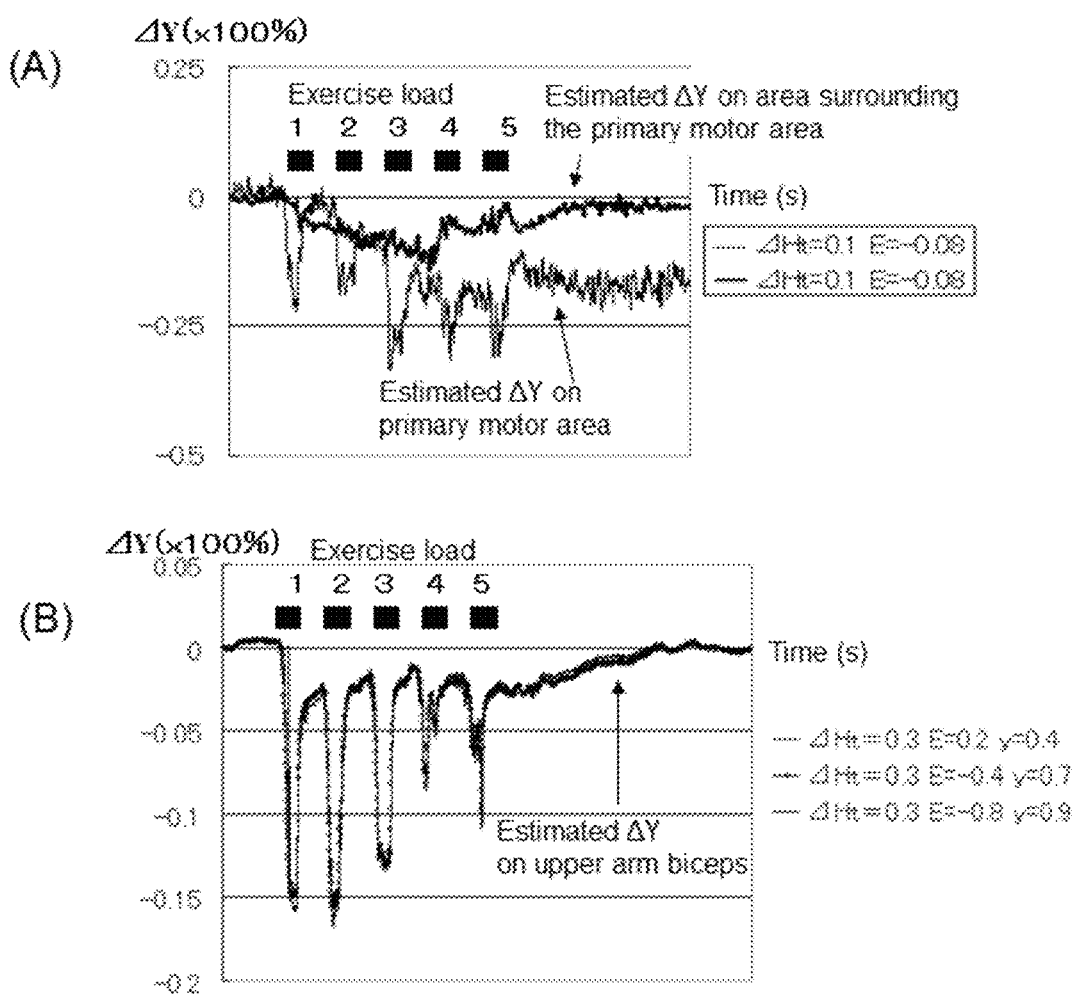
FIG. 30 is graphs showing time series changes in $\Delta Y$ from simultaneous measurements of the brain and the muscle for upper arm biceps exercise; (A) shows time series changes in estimated ΔY on the primary motor area and estimated ΔY on the area surrounding the primary motor area, and (B) shows time series changes in estimated ΔY on the upper arm biceps.

FIG. 30 is graphs showing time series changes in ΔY from simultaneous measurements of the brain and the muscle for upper arm biceps exercise; (A) shows time series changes in estimated ΔY on the primary motor area and estimated ΔY on the area surrounding the primary motor area, and (B) shows time series changes in estimated ΔY on the upper arm biceps.

As can be seen from FIGS. 30(A) and (B), the use of estimated ΔY makes it possible to compare 3 different sites regardless of the ROI sizes.

It is the primary motor area of the brain that becomes hypoxic while working together with the upper arm biceps, while its surrounding area becomes hyperoxic. Furthermore, during rest, both the primary motor area and its surrounding area are hypoxic, suggesting that the dumbbell exercise load is quite strong.

In the past, even though signal drift occurred during rest, we were unable to explain its physiological meaning. Furthermore, in repetitions 4 and 5, assistance was provided when the subjects became tired and the muscle exercise became difficult to continue, but the hypoxic load continued in the motor area of the brain.

In this way, calculating estimated ΔY makes it possible to measure and evaluate the degree of fatigue in the brain and muscle, the interactions between them, and so on.

Figure 31:
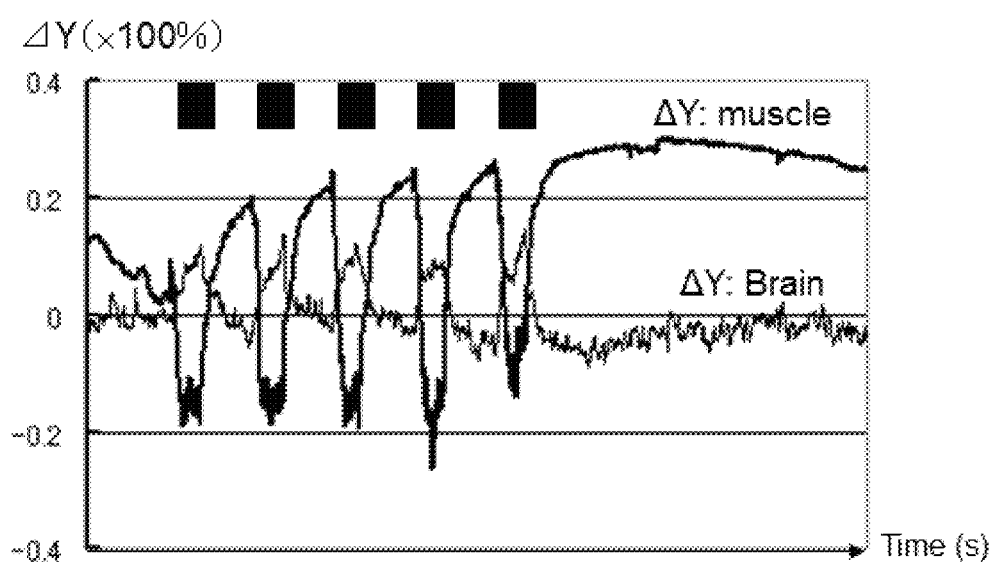
FIG. 31 is a graph of degree of oxygen saturation (ΔY), showing time series changes measured simultaneously for the brain and muscle.

FIG. 31 is a graph of degree of oxygen saturation (ΔY), showing time series changes measured simultaneously for the brain and muscle.

Figure 32:
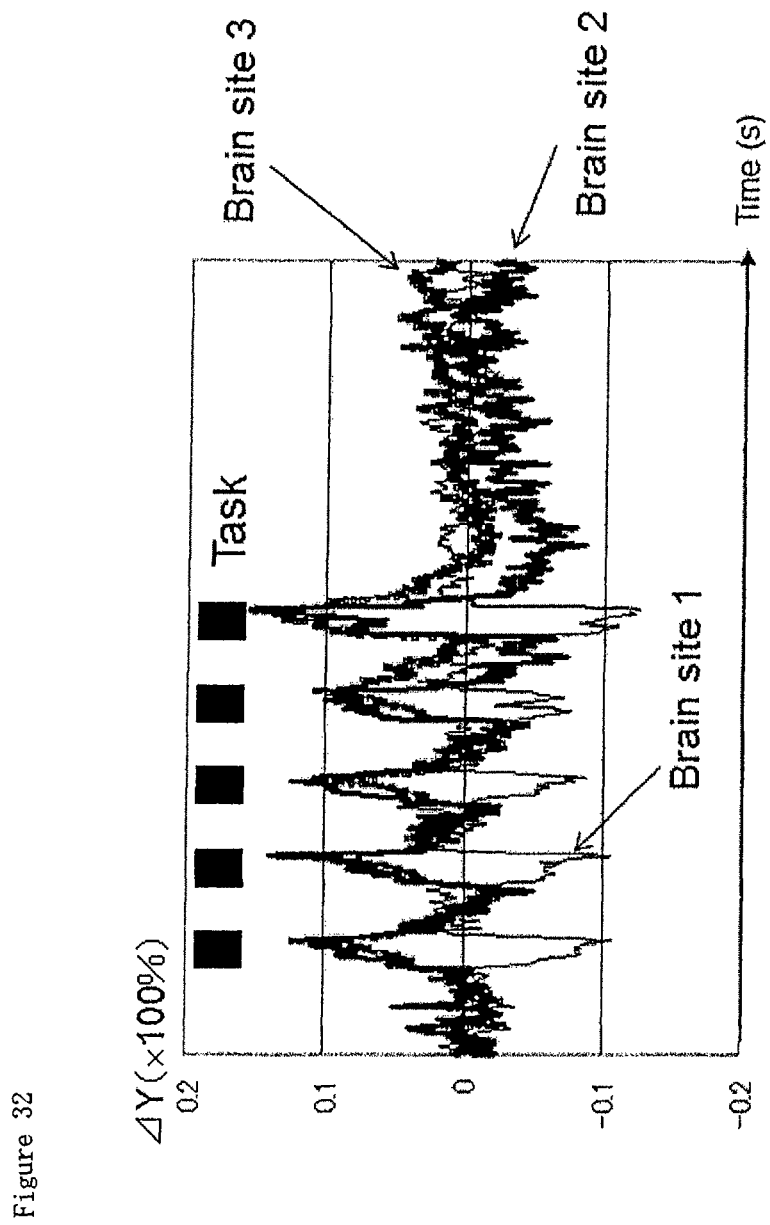
FIG. 32 is a graph showing time series changes in degree of oxygen saturation ΔY at a plurality of different sites of the brain accompanying task implementation.

FIG. 32 is a graph showing time series changes in degree of oxygen saturation ΔY at a plurality of different sites of the brain accompanying task implementation. In FIG. 32, the black blocks (■) indicate task times.

FIG. 33(A) is a graph with amounts of oxyhemoglobin (O) in a ROI as the horizontal axis and amounts of deoxyhemoglobin (D) in the ROI as the vertical axis, showing their relationship with degree of oxygen saturation Y; and (B) is a graph showing the relationships between change in oxyhemoglobin in the ROI (ΔO), change in deoxyhemoglobin in the ROI (ΔD), and change in the angle Y (ΔY).

In FIG. 33(A), if the angle of the upward slope is taken to be the angle Y, then Oxygen saturation Y=1-arc tan(Y)  (Equation 42)

In addition, in FIG. 33(B), because change in the degree of oxygen saturation Y is dependent on ∠ΔY, it can be obtained as:

Change in degree of oxygen saturation ΔY=arc tan (∠ΔY)  (Equation 43)

This shows that change in the degree of oxygen saturation can occur if there is a change in either change in oxyhemoglobin (ΔO) or change in deoxyhemoglobin (ΔD).

Now, in the past, with fMRI, changes were detected in ΔD, which is paramagnetic, while changes in ΔO, which is diamagnetic, were not detected, and thus changes in oxygen saturation in which ΔD was unchanged were not detected.

In addition, with previous NIRS techniques, not only were ΔD and ΔO handled separately, but change in ΔO was considered the main index, and thus measurements from fMRI and NIRS and the like of changes in degree of oxygen saturation were lacking in accuracy. As FIG. 33(C) shows, because changes in degree of oxygen saturation are determined by changes in the coordinates (ΔO, ΔD) on the O/D plane, the correct angle for ΔY cannot be obtained when the degree of oxygen saturation is calculated independently from ΔD and ΔO, and completely opposite results are obtained depending on whether the changes are increases or decreases from the measurement starting point, resulting in erroneous evaluations of the degree of oxygen saturation.

Technique 2 for lessening the problem of non-uniform ROIs (regions of interest) when taking NIRS measurements from a plurality of sites In Technique 2, a unit circle is drawn on a two-dimensional diagram by means of 2 real time normalizations, using L.

Here, where
D=deoxyhemoglobin,
O=oxyhemoglobin,
ΔD=change in deoxyhemoglobin,
ΔO=changes in oxyhemoglobin,
ΔL is defined by $$\Delta L^2 = (\text{change in deoxyhemoglobin})^2 + \quad \text{(Equation 44)}$$
$$(\text{change in oxyhemoglobin})^2$$
$$= 1/2\{(\Delta D - \Delta O)^2 + (\Delta D + \Delta O)^2\}$$

If D (deoxyhemoglobin) and O (oxyhemoglobin) can be quantified, then L can be used for normalization instead of ΔL, where L is obtained by:

$$L = (\text{deoxyhemoglobin})^2 + (\text{oxyhemoglobin})^2 \quad \text{(Equation 45)}$$
$$= 1/2\{(D - O)^2 + (D + O)^2\}$$

First, values for L from the measurement sites are calculated in real time and normalization is performed using the maximum value of L from among the plurality of sites, at intervals of a desired number of seconds.

Or, normalization is performed using the maximum value of L at each site, at intervals of a desired number of seconds.

Then, two-dimensional adjustments (normalizations) are made based on the maximum value of L, normalizing the data at, for example, 5-second intervals, making it possible to evaluate all the data on the same scale, so that it can be seen at a glance where (at which site) changes are occurring, and what percent the changes are of those at the channel showing the maximum value of L, in real time.

For example, the ratio between $\Delta L_{max}$ from the muscle and from the brain is calculated to find the slope on a two-dimensional diagram, with the one N times the other.

$$\text{Muscle } \Delta L_{max}/\text{Brain } \Delta L_{max} = N \quad \text{(Equation 46)}$$

In this case, even if the brain and/or the muscle are measured at multiple points, each of their maximum values of L is calculated.

FIG. 34(A)-(C) are graphs illustrating the steps for selecting the maximum value of L from muscle data (ΔO, ΔD) to perform unit circle normalization.

First, the maximum value of L is selected from a time series of the data (ΔD, ΔO) (see FIG. 34(A)).

Next, ΔD+ΔO and ΔD−ΔO are calculated and a time series graph is created (see FIG. 34(B)).

Next, a unit circle is created with the maximum value of L as the radius, with ΔD+ΔO as the horizontal axis and ΔD−ΔO as the vertical axis (see FIG. 34(C)).

Previously, even if there was a difference between changes from different sites because the ROI sizes (size of the measurement target) were different, it was impossible to tell if small changes were due to differences in size of the ROIs, or to the smallness of the response.

Accordingly, there will be cases of maximum L normalization when the maximum value of L is set for each ROI, and cases when the maximum value of L is selected from among a plurality of ROIs.

Maximum L normalization in which the maximum value of L is set for each ROI is effective in cases when the difference between sites is large, such as the muscle and the brain, or the mouth and the brain.

Selecting the maximum value of L from among a plurality of ROIs is effective when inter-probe spacing is uniform and the ROIs can be quantified, such as in the brain alone, or on the skin alone.

FIG. 35(A)-(C) are graphs illustrating the steps for selecting the maximum value of L from brain data (ΔO, ΔD), and normalizing the data on a unit circle.

First, the maximum value of L is selected from a time series of the data (ΔD, ΔO) (see FIG. 35(A)).

Next, ΔD+ΔO and ΔD−ΔO are calculated and a time series graph is created (see FIG. 35(B)).

Next, a unit circle is created with the maximum value of L as the radius, with ΔD+ΔO as the horizontal axis and ΔD−ΔO as the vertical axis (see FIG. 35(C)).

Differences in fluctuation directions, from among the 4 vector directions, and the magnitude of change can be seen from the unit circle normalization.

From the magnitude of that fluctuation, the point when activation occurs due to the task can be seen as a percentage of the whole by superimposing the maximum values for ΔL at rest and the values for ΔL at task completion.

Figure 34:
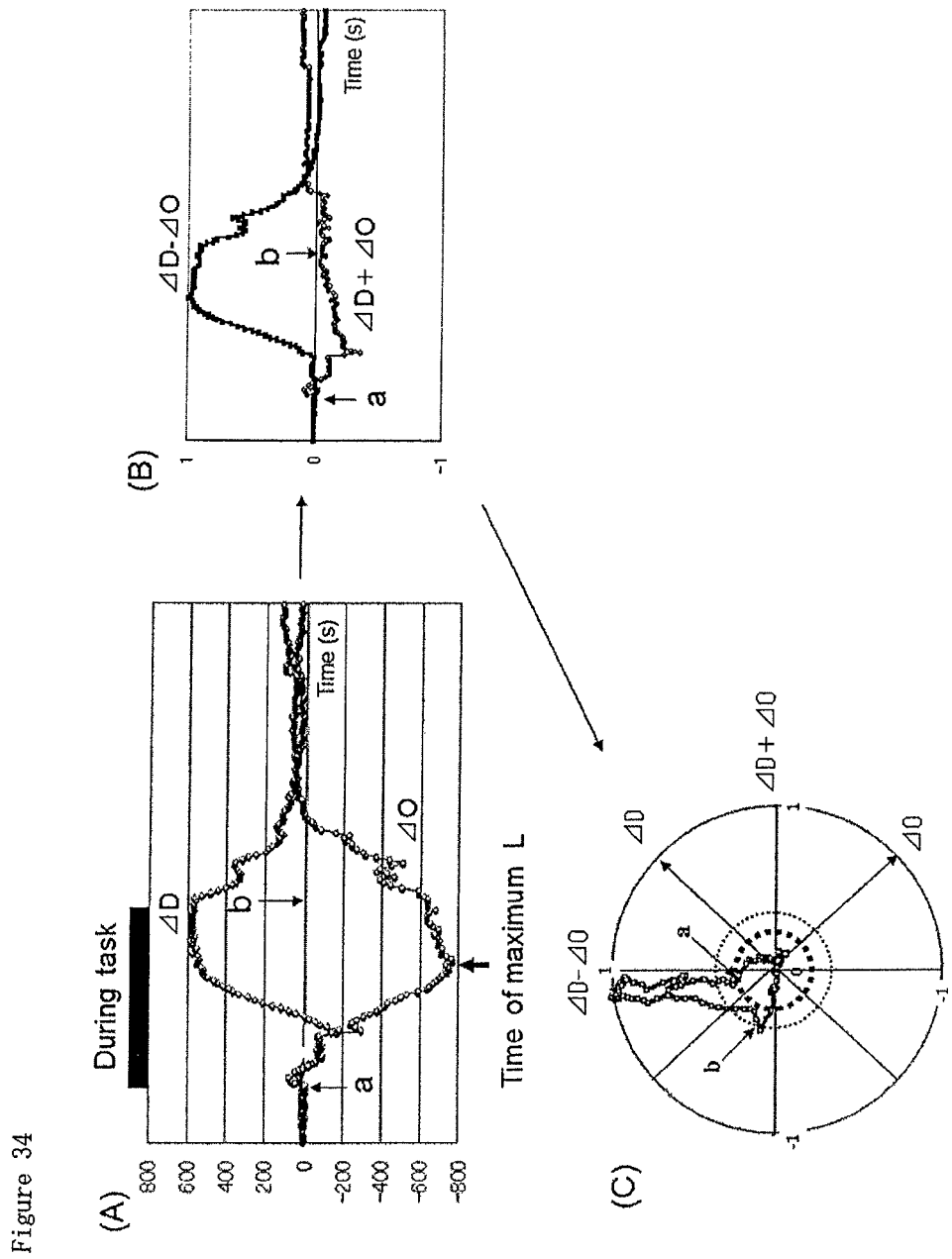
FIG. 34(A)-(C) are graphs describing the steps for selecting the maximum value of L from muscle data (ΔO, ΔD) to perform unit circle normalization.
Figure 35:
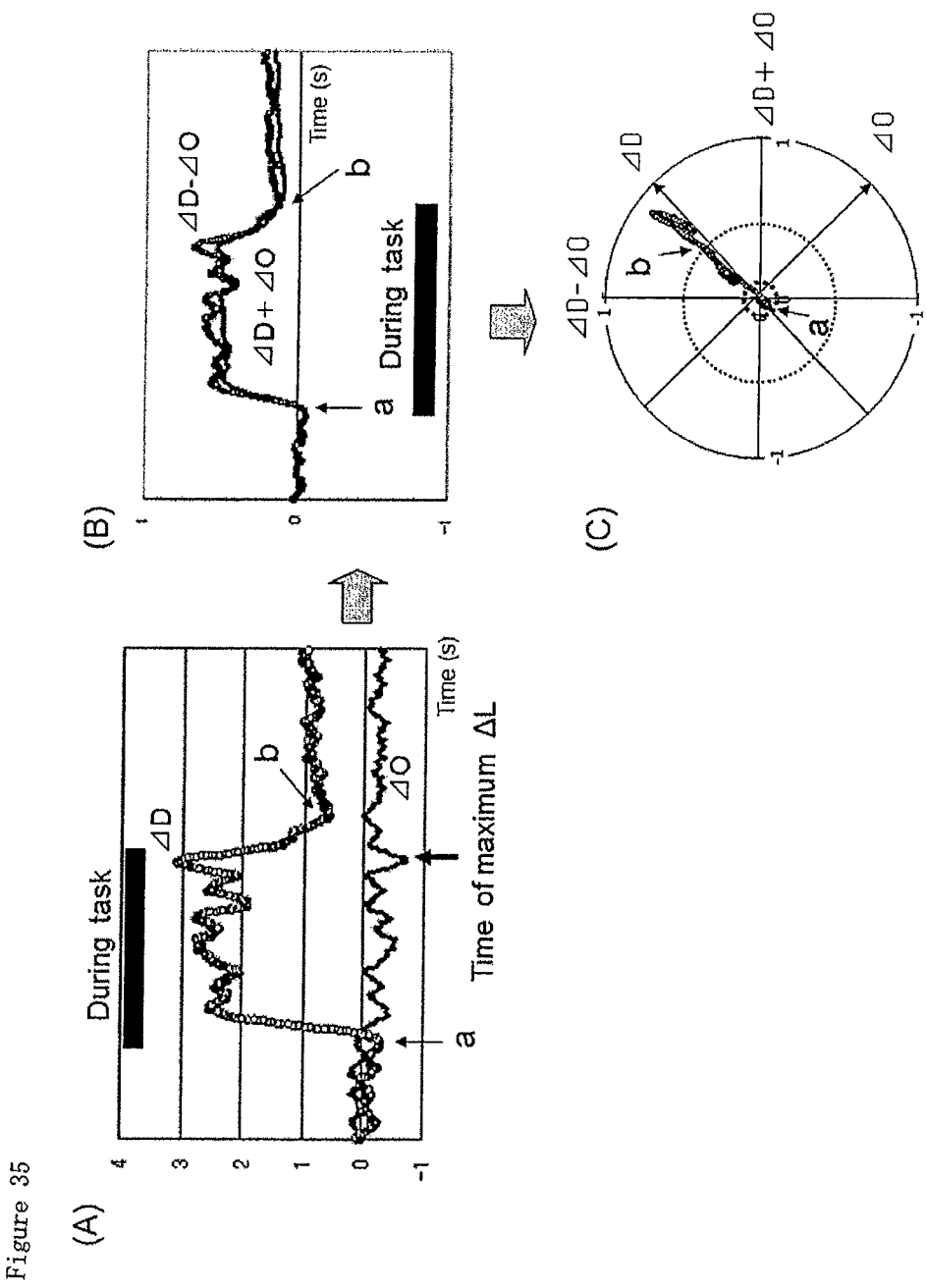
FIG. 35(A)-(C) are graphs illustrating the steps for selecting the maximum value of L from brain data (ΔO, ΔD), and normalizing [the data] on a unit circle.

The muscle-to-brain $\Delta L_{max}$ ratio is calculated from the data of FIGS. 34 and 35, and the brain values are multiplied by N to determine the slope on a two-dimensional diagram. Equation 46 is used for N.

Figure 36:
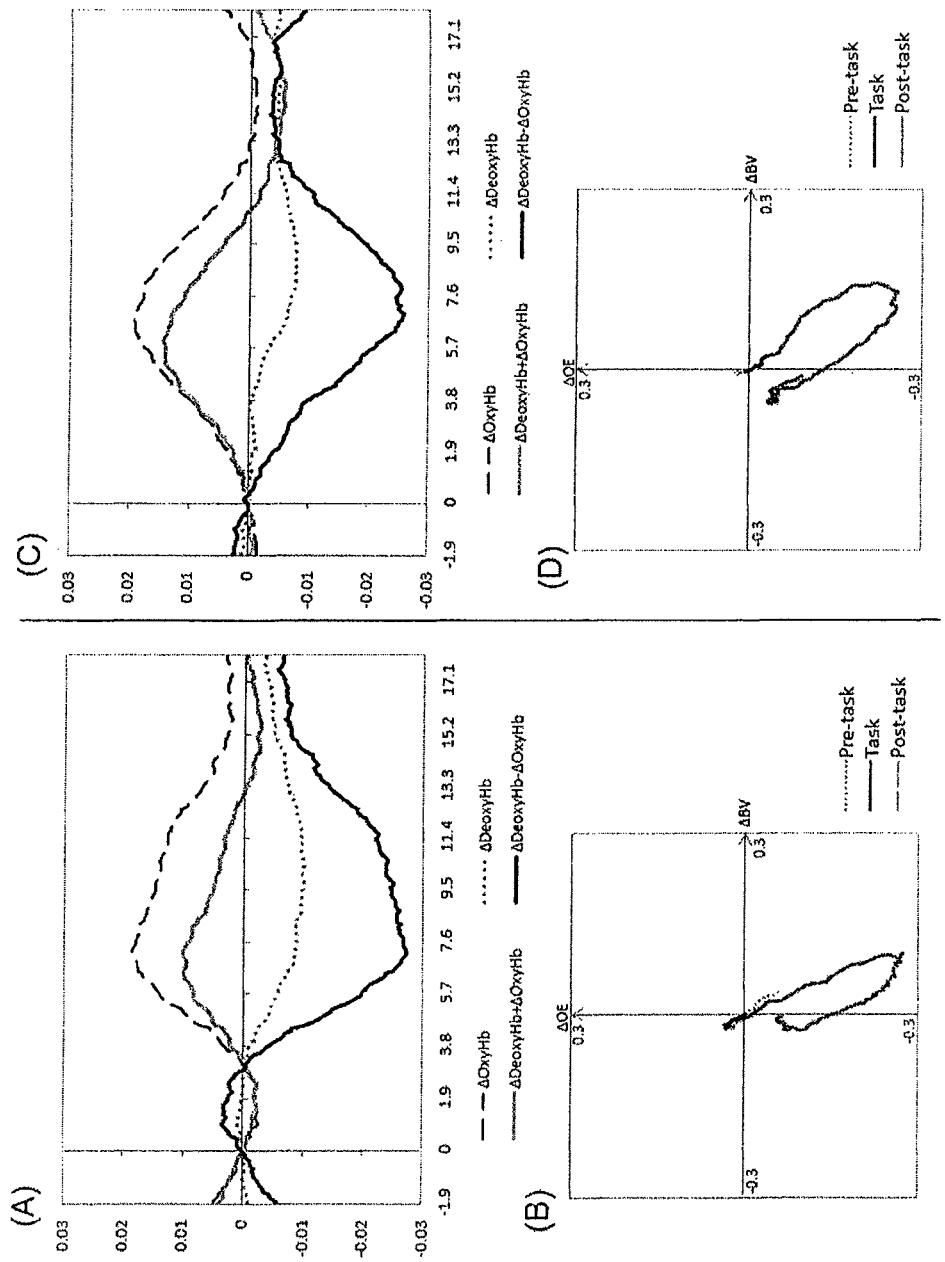
FIG. 36(A) is a time series graph of data set A (ΔD, ΔO, ΔD+ΔO, ΔD−ΔO) of a given site; (B) is a two-dimensional diagram showing data set A as time series changes (before, during and after a task), where the horizontal axis is ΔBV (ΔD+ΔO) and the vertical axis is ΔOE (ΔD−ΔO); (C) is a time series graph of data B set (ΔD, ΔO, ΔD+ΔO, ΔD−ΔO) of a given site; and (D) is a two-dimensional diagram showing data [set] B as time series changes (before, during and after the task), where the horizontal axis is ΔBV (ΔD+ΔO) and the vertical axis is ΔOE (ΔD−ΔO).

FIG. 36(A) is a time series graph of data set A (ΔD, ΔO, ΔD+ΔO, ΔD−ΔO) of a given site; (B) is a two-dimensional diagram showing data set A as time series changes (before, during and after a task), where the horizontal axis is ΔBV (ΔD+ΔO) and the vertical axis is ΔOE (ΔD−ΔO); (C) is a time series graph of data B set (ΔD, ΔO, ΔD+ΔO, ΔD−ΔO) of a given site; and (D) is a two-dimensional diagram showing data [set] B as time series changes (before, during and after the task), where the horizontal axis is ΔBV (ΔD+ΔO) and the vertical axis is ΔOE (ΔD−ΔO).

Maximum values of L ($L_{max}$) are calculated from data [sets] A and B, and, for normalization of the data so that $L_{max}=1$ (normalization of the amplitude), the inverse of L is calculated and this inverse is taken as the normalization value.

Next, each index (O, D, D−O and D+O) is multiplied by the normalization value, and the normalized data are plotted on a two-dimensional plane (unit circle graph).

Figure 37:
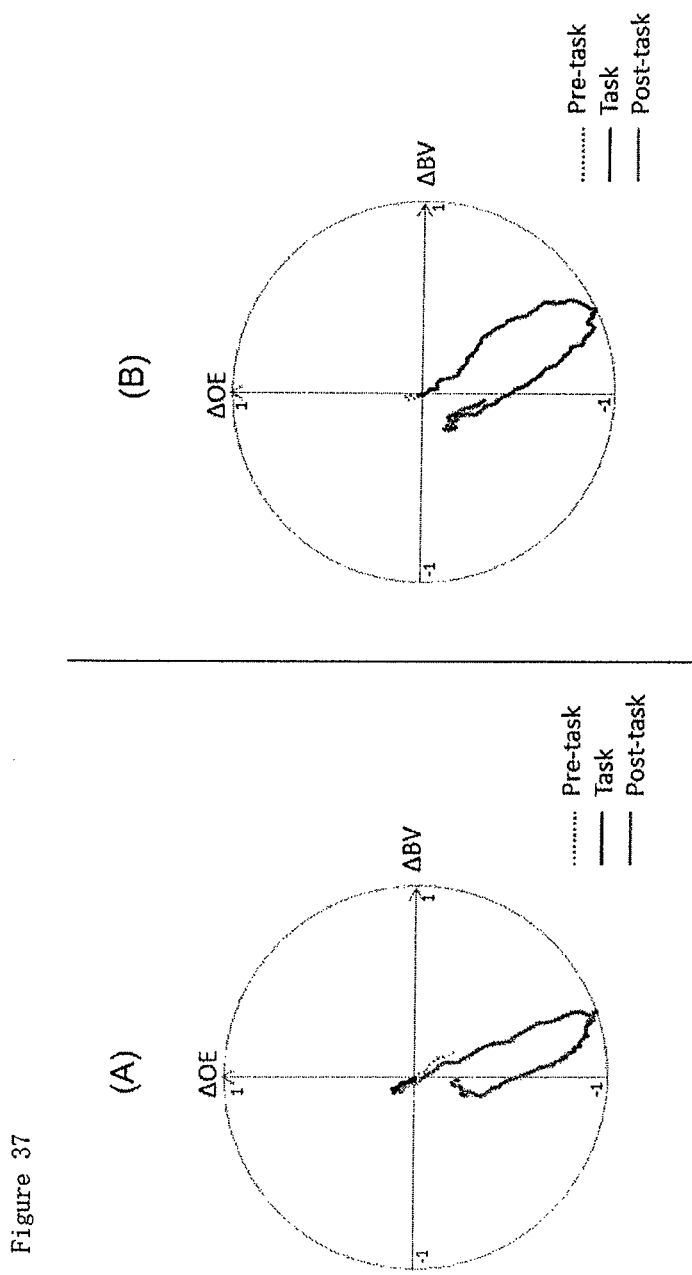
FIG. 37(A) is a two-dimensional graph of data [set] A after $\Delta L_{max}$ normalization, and (B) is a two-dimensional graph of data set B after $\Delta L_{max}$ normalization.

FIG. 37(A) is a two-dimensional graph of data [set] A after $L_{max}$ normalization, and (B) is a two-dimensional graph of data set B after $L_{max}$ normalization.

Steps like those described above are also performed when normalizing BV (D+O) and OE (D−O). In this case, however, they not become unit circle graphs.

Figure 38:
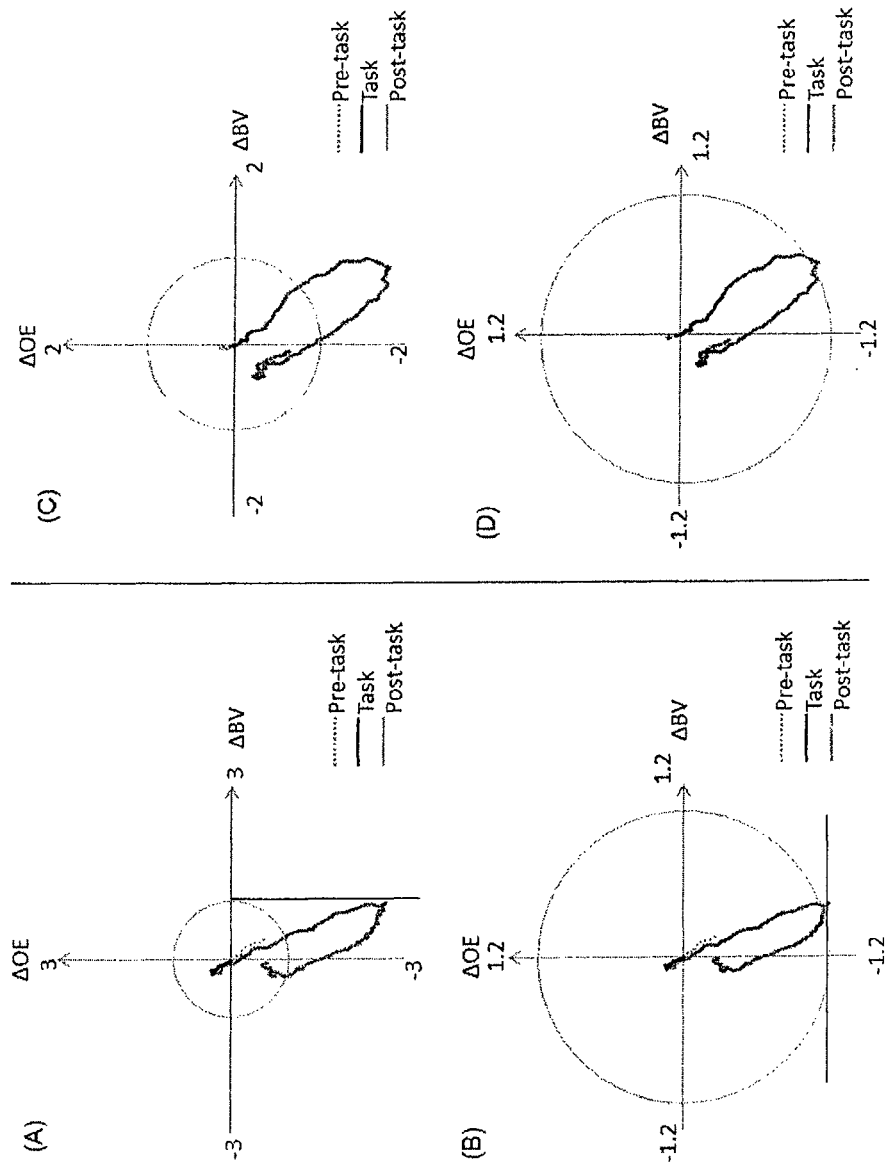
FIG. 38(A) is a two-dimensional graph of data set A after $\Delta BV_{max}$ normalization; (B) is a two-dimensional graph of data set A after $\Delta OE_{max}$ normalization; (C) is a two-dimensional graph of data set B after $\Delta BV_{max}$ normalization; and (D) is a two-dimensional graph of data [set] B after $\Delta OE_{max}$ normalization.

FIG. 38(A) is a two-dimensional graph of data [set] A after $\Delta BV_{max}$ normalization; (B) is a two-dimensional graph of data set A after $\Delta OE_{max}$ normalization; (C) is a two-dimensional graph of data set B after $\Delta BV_{max}$ normalization; and (D) is a two-dimensional graph of data set B after $\Delta OE_{max}$ normalization.

It is also possible to perform $L_{max}$ normalization in real time.

First, a calibration interval is set (for example, 3 s).

Next, after measurement is started, $L_{max}$ is calculated at 3-s intervals from the measurement start by the same steps described above, and a graph is plotted on a unit circle.

If $L_{max}$ is not replaced, the graph continues to display in real time with the same normalization value conversion.

If $L_{max}$ is replaced with a new value, the scale is updated for the data up to that point, and a graph [of the data] after the new normalization value conversion is displayed.

Figure 39:
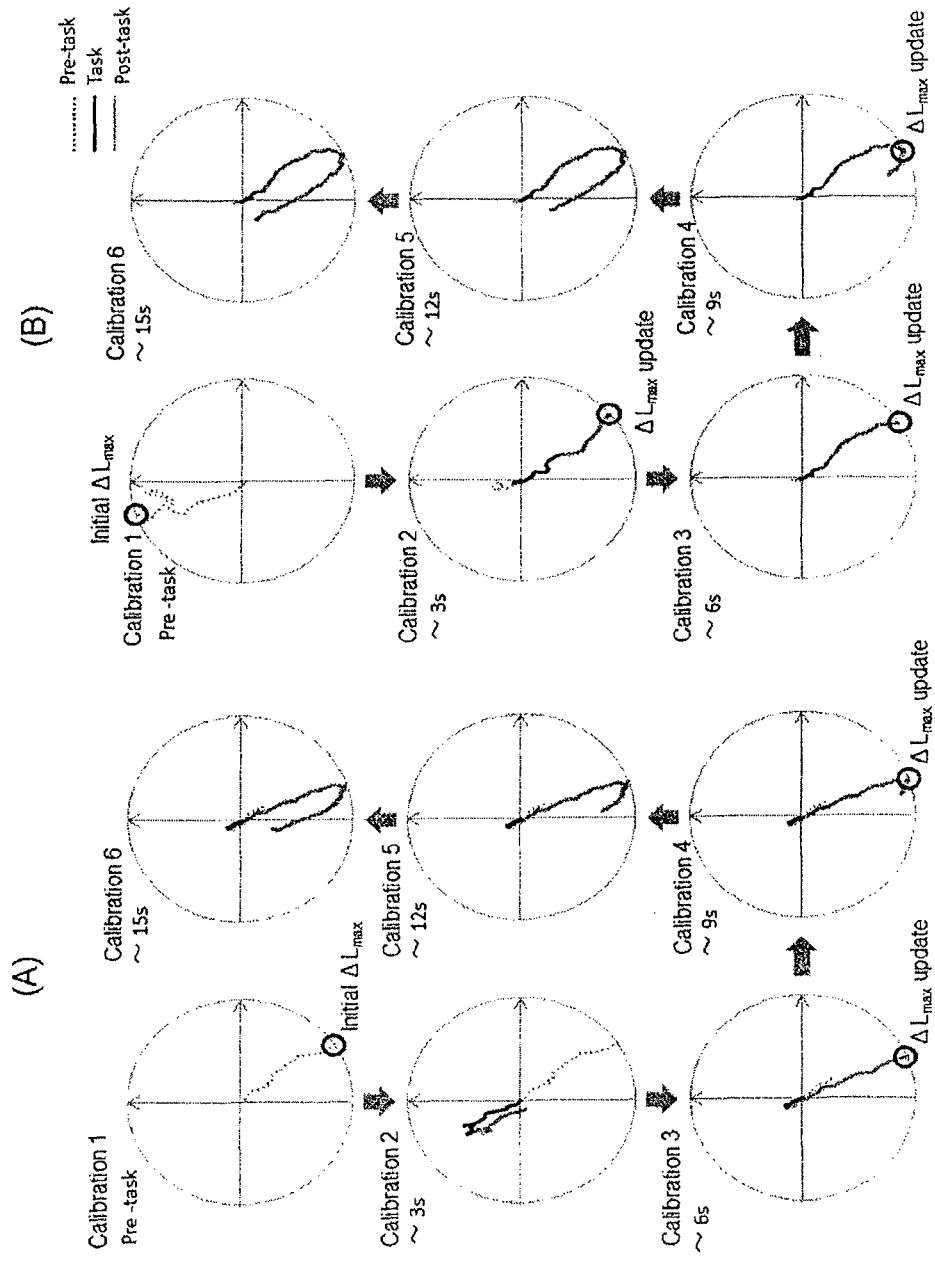
FIG. 39(A) is a graph of data set A showing the steps for $\Delta L_{max}$ normalization in real time and creating a unit circle; (B) is a graph of data set B showing the steps for $\Delta L_{max}$ normalization in real time and creating a unit circle.

FIG. 39(A) is a graph of data set A showing the steps for $L_{max}$ normalization in real time and creating a unit circle; (B) is a graph of data set B showing the steps for $L_{max}$ normalization in real time and creating a unit circle.

[Technique 3 for Lessening the Problem of Non-Uniform ROIs (Regions of Interest) when Taking NIRS Measurements from a Plurality of Sites]

Technique 3 is a method which takes the product of data from a plurality of sites.

When measured values from the brain and measured values from the arm are displayed on a two-dimensional diagram, it is necessary to adjust them because the amounts of change and measurement conditions are different.

One way to do this is a time series display of (changes in the brain)×(changes in the arm). This also makes it possible to select out brain sites showing different responses to arm exercise.

When the muscle tires, the brain works harder, but determining the maximum product [of brain and arm data] makes it possible to tell what kind of exercise, when and for how long, and the like, can induce the brain and the muscle to work together effectively. This is an effective way to evaluate training effectiveness.

FIG. 40(A) is a graph showing time series changes in the product of blood volumes (D+O) of the brain and the muscle, and (B) is a graph showing time series changes in the product of oxygen exchange (D−O) of the brain and the muscle.

Figure 40:
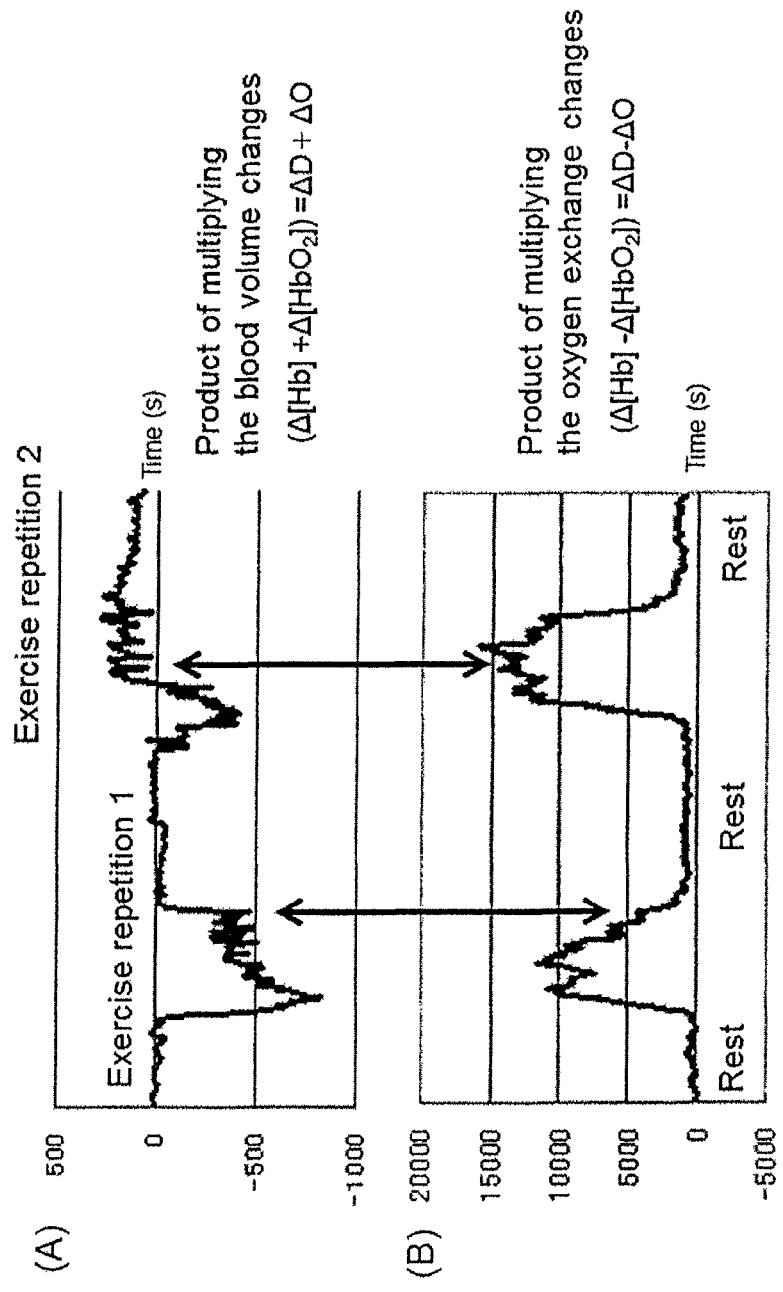
FIG. 40(A) is a graph showing time series changes in the product of multiplying the blood volumes (ΔD+ΔO) of the brain and the muscle, and (B) is a graph showing time series changes in the product of multiplying the oxygen exchange (ΔD−ΔO) of the brain and the muscle.
Figure 41:
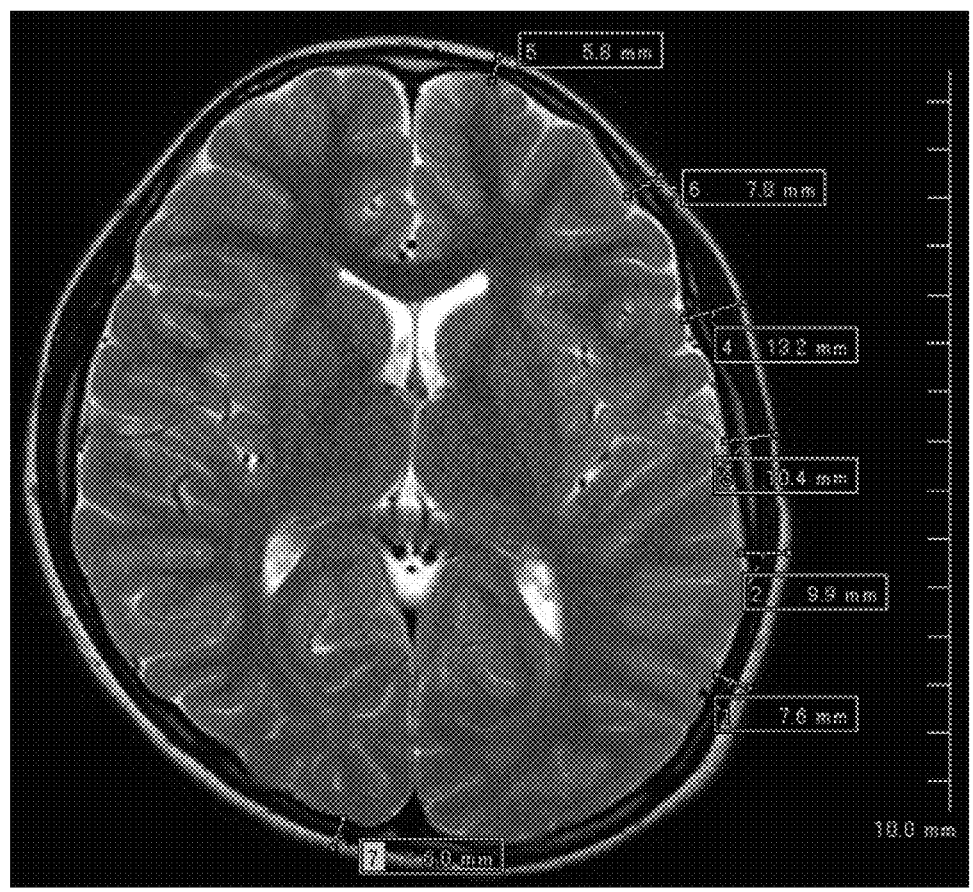
FIG. 41 is an image showing distances from the scalp to the cerebral parenchyma of the brain.

From FIG. 40, it can be seen in the second exercise repetition that the exercise of the brain and the body is getting more efficient, from the fact that oxygen exchange is increasing without changing the blood volume.

[Technique 1 for Composite Visualization and Imaging of Physiological Indices]

Here, the present inventor will refer to techniques for composite visualization and imaging of physiological indices (amounts of change and parameters) as "hybrid imaging". This hybrid imaging includes 2 techniques: Technique 1, in which a physiological index common to a plurality of sites, such as the brain and the muscle, is visualized and imaged in a composite way, and Technique 2, in which a plurality of physiological indices are visualized and imaged in a composite way.

Figure 42:
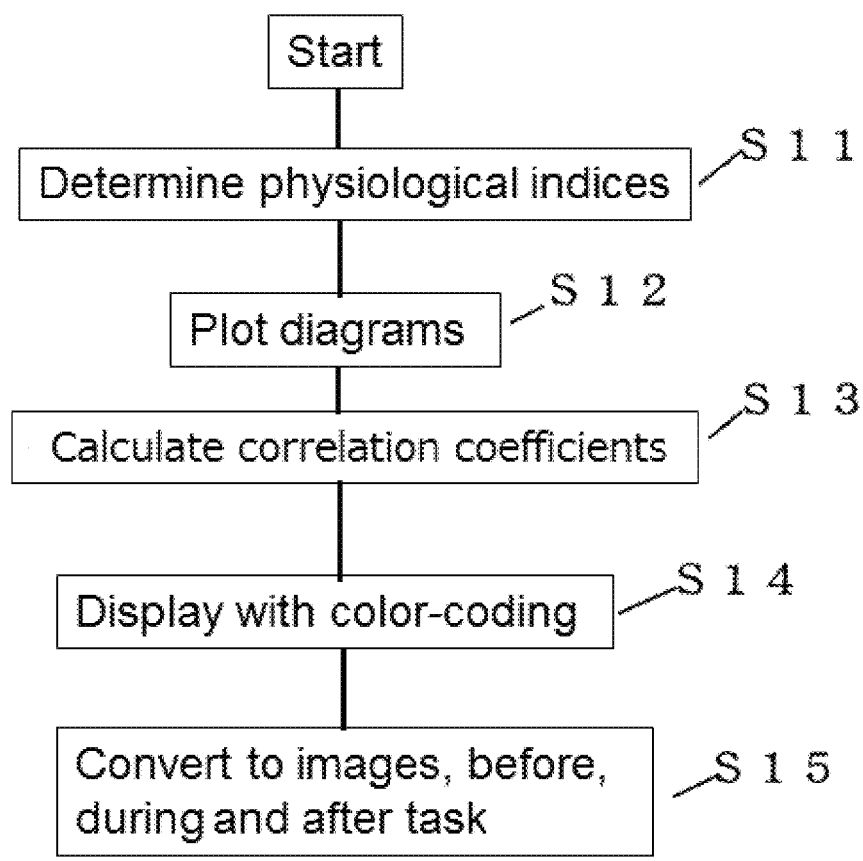
FIG. 42 is a flowchart illustrating the steps in Technique 1 for hybrid imaging.

FIG. 42 is a flowchart illustrating the steps in Technique 1 for hybrid imaging.

First, using the apparatus for evaluating physiological function of the embodiment of the present invention, values for physiological indices such as, for example, O (changes in oxyhemoglobin), D (changes in deoxyhemoglobin), OE (changes in oxygen exchange), BV (change in blood volume), the ratio E (ratio of oxygen exchange to blood volume) and the value L (distance within a phase) are determined respectively for the brain and the muscle (Step S11).

Next, a diagram is drawn in 2 dimensions for each physiological index (Step S12).

Next, the slope of the above-mentioned diagram, namely, the correlation coefficient, is calculated for each site by means of calculating part 10 (Step S13).

Next, the correlation coefficient values are displayed on display part 9, color-coded from −1.0 to 1.0 (Step S14).

Next, these are converted to images, divided into before, during and after the task (Step S15). By this means, the relationship between brain metabolism and muscle metabolism during the recovery period can also be seen.

This is hybrid imaging of muscle and brain activity, utilizing the correlation coefficients of physiological indices.

Figure 43:
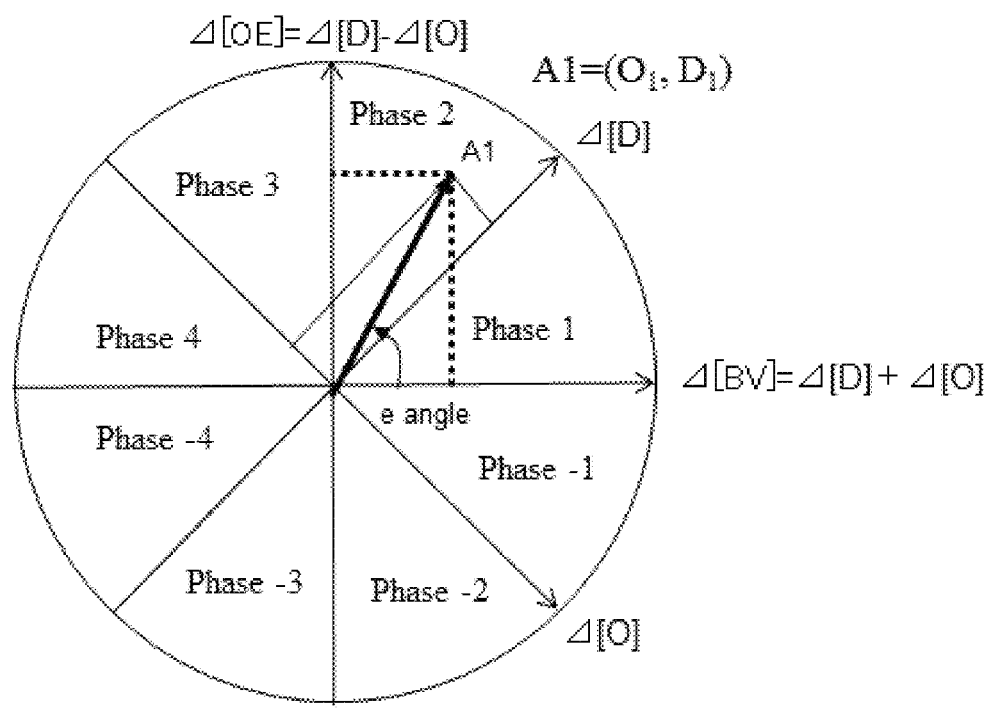
FIG. 43 is a two-dimensional diagram illustrating physiological indices.

FIG. 43 is a two-dimensional diagram illustrating physiological indices.

Thinking of a plurality of hemoglobin indices as trajectories on a vector space and taking into consideration their direction and the magnitude of their strength (scalar) makes it possible to measure the relative strength of muscle and brain activity in real time and convert it to images.

Capturing changes in oxyhemoglobin (ΔO) and changes in deoxyhemoglobin (ΔD) as wave motion and rotational motion dynamics from a measurement starting point on a vector space makes it possible to create a plurality of indices that represent the relationship between the changes in the two: changes in oxyhemoglobin and changes in deoxyhemoglobin.

In FIG. 43, ΔOE, ΔBV, ΔL, the ratio E and the angle E are physiological indices, and they are calculated respectively by the equations below:

$$\Delta[OE]=\Delta[D]-\Delta[O]$$

$$\Delta[BV]=\Delta[D]+\Delta[O]$$

$$\Delta[L]^2=\Delta[D]^2+\Delta[O]^2$$

$$\text{Ratio } E=\Delta[OE]/\Delta[BV]$$

$$\text{Angle } E=\text{arc tan (Ratio } E\text{)}$$

Using these indices ΔOE, ΔBV, ΔL, Ratio E and Angle E to determine the correlation coefficients between the brain and the muscle, or between sites in the brain, makes it possible to measure and image the relative strengths of muscle and brain activity in real time.

Figure 44:
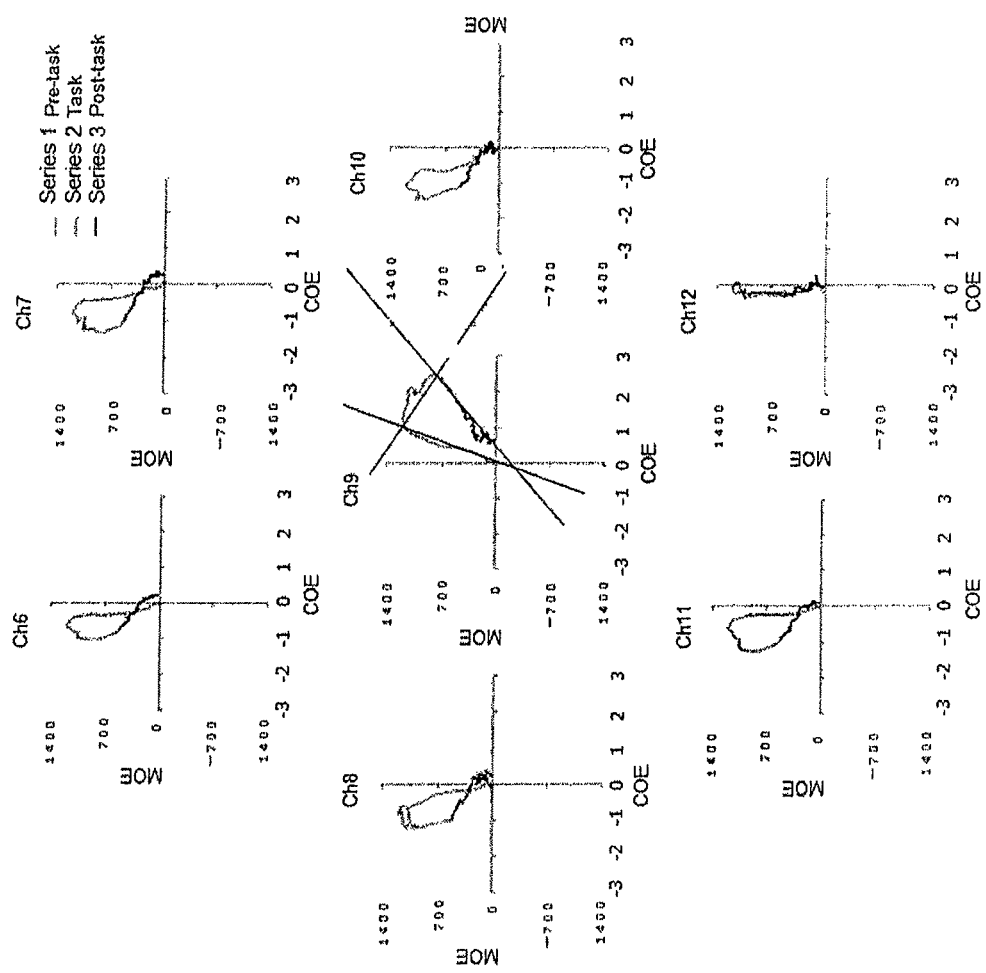
FIG. 44 is an example of two-dimensional diagrams in which the physiological index OE (oxygen exchange) is obtained from the muscle and the brain, and visualized in a composite way.

FIG. 44 is an example of two-dimensional diagrams in which the physiological index OE (oxygen exchange) is obtained from the muscle and the brain, and visualized in a composite way. The vertical axes are change in muscle oxygen exchange concentration (MOE; upper arm biceps), and the horizontal axes are change in cerebral oxygen exchange concentration (COE; primary motor area and area surrounding the primary motor area). Units on the axes are mmol/l. In addition, Series 1 shows the trajectory for 5 s before the task; Series 2, the trajectory for 36 s during the task; and Series 3, the trajectory for 55 s after the task. The task here is lifting a 14.5 kg dumbbell.

Here Channel 9 (Ch9) is the primary motor area (M1) of the left brain and Channel 21 (Ch21) is the primary motor area (M1) of the right brain. Channels 6, 7, 8, 10, 11 and 12 surround Channel 9; and Channels 18, 19, 20, 22, 23 and 24 surround Channel 21, in the motor areas surrounding the primary motor areas (M1). Oxygen consumption occurs in the primary motor areas (M1) because it is working, subjected to a load/weight even from muscle exercise, but in the surrounding areas, oxygen is not consumed even though blood is being supplied, and thus they respond differently.

Figure 45:
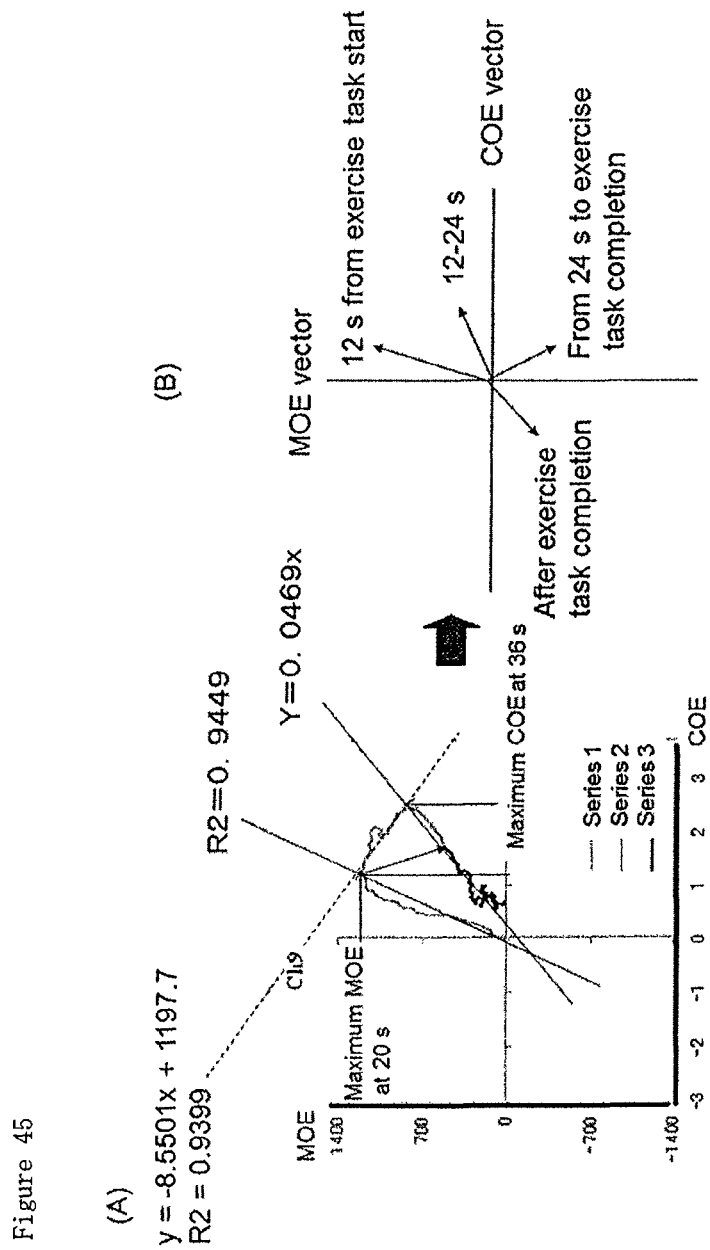
FIG. 45(A) is a detail view of FIG. 44 showing the diagram for Channel 9 (Ch9), and (B) is a vector representation of the movement (rotation) of OE over time. The vertical axis here is change in muscle oxygen exchange concentration (MOE; upper arm biceps), and the horizontal axis is change in cerebral oxygen exchange concentration (COE; primary motor area).

FIG. 45(A) is a detail view of FIG. 44 showing the diagram for Channel 9 (Ch9), and (B) is a view of a vector representation of the movement (rotation) of OE over time. The vertical axis here is change in muscle oxygen exchange concentration (MOE; upper arm biceps), and the horizontal axis is change in cerebral oxygen exchange concentration (COE; primary motor area). Units on the axes are mmol/l.

As can be seen from FIG. 45(A), for the index OE, MOE and COE peak at different times; MOE (maximum at 20 s) reaches its maximum value 16 s earlier than COE (maximum at 36 s). The difference between these two times shows that there are temporal differences in the muscle and brain activity.

In addition, the vector representation shown in FIG. 45(B) can be evaluated to mean that the relationship between oxygen metabolism in the brain and the muscle is changing even during the exercise task.

Figure 46:
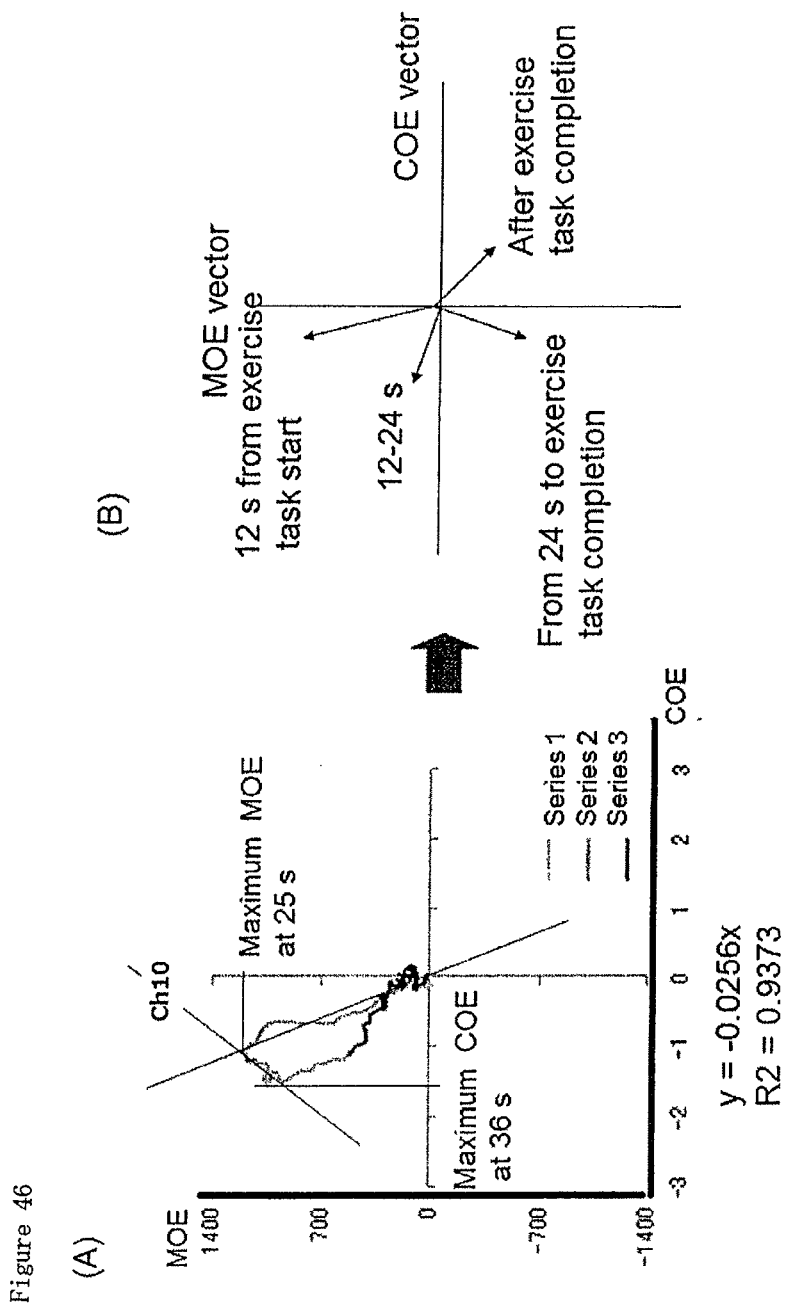
FIG. 46(A) FIG. 46(A) is a detail view of FIG. 44 showing the diagram for Channel 10 (Ch10), and (B) is a view of a vector representation of the movement (rotation) of OE over time. The vertical axis here is change in muscle oxygen exchange concentration (MOE; upper arm biceps), and the horizontal axis is change in cerebral oxygen exchange concentration (COE; area surrounding the primary motor area).

FIG. 46(A) is a detail view of FIG. 44 showing the diagram for Channel 10 (Ch10), and (B) is a view of a vector representation of the movement (rotational) of OE over time. The vertical axis here is change in muscle oxygen exchange concentration (MOE; upper arm biceps), and the horizontal axis is change in cerebral oxygen exchange concentration (COE; area surrounding the primary motor area). Units on the axes are mmol/l.

As can be seen from FIG. 46(A), for the index OE, MOE and COE peak at different times; MOE (maximum at 25 s) reaches its maximum value 11 s earlier than COE (maximum at 36 s). The difference between these two times shows that there is are temporal differences in the muscle and brain activity.

In addition, the vector representation shown in FIG. 46(B) can be evaluated to mean that the relationship between oxygen metabolism in the brain and the muscle is changing even during the exercise task.

Regarding the equations and R2 in FIGS. 45(A) and 46(A), [R2] is the square of the correlation coefficient (Pearson's product-moment correlation coefficient), and the regression line is determined by drawing an approximate straight line by means of the least squares method in the designated segment. The closer the correlation coefficient r is to 1 or −1, the stronger the correlation, and the closer it is to zero, the weaker the correlation becomes.

Figure 47:
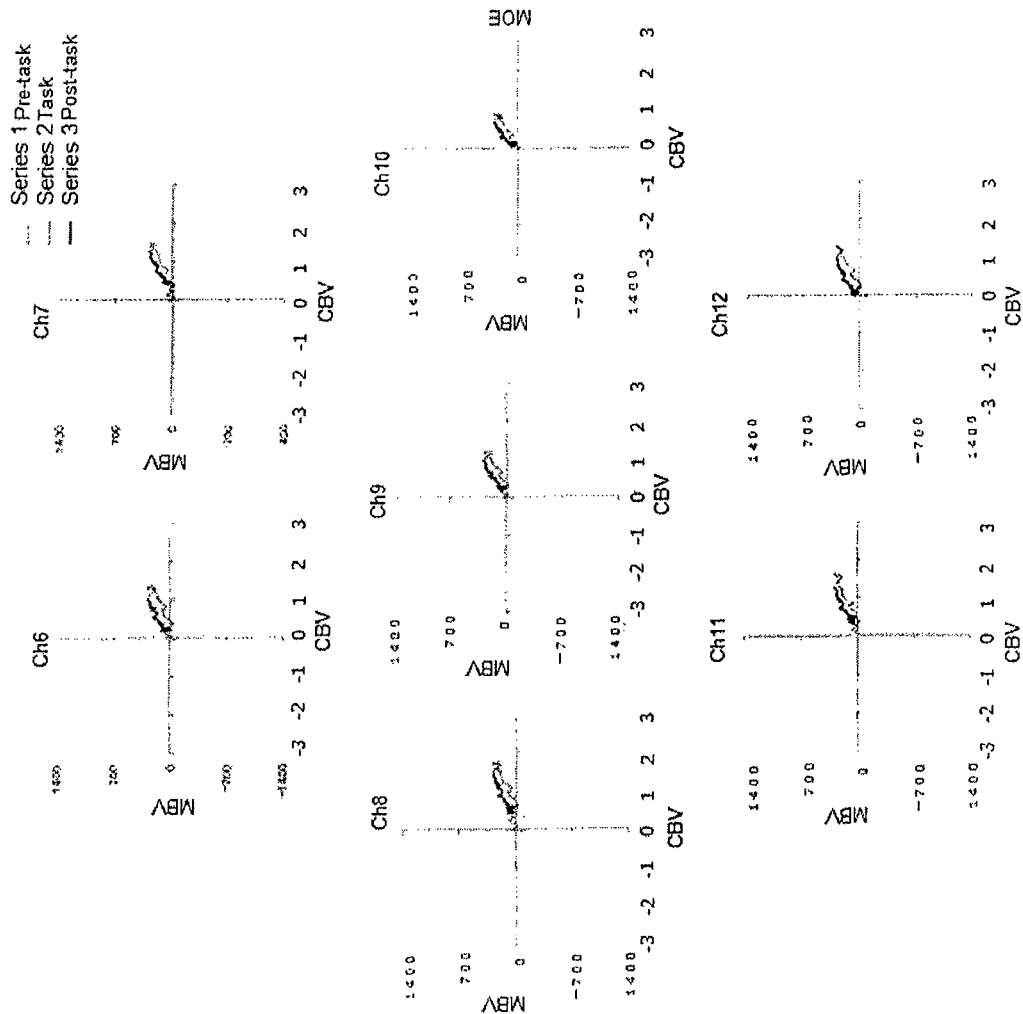
FIG. 47 is an example of two-dimensional diagrams in which the physiological index BV (blood volume) is extracted from the muscle and the brain and plotted two-dimensionally in a composite way.

FIG. 47 is an example of two-dimensional diagrams in which the physiological index BV (blood volume) is extracted from the muscle and the brain and plotted two-dimensionally in a composite way. Here, the vertical axes are change in muscle blood volume concentration (MBV; upper arm biceps), and the horizontal axes are change in cerebral blood volume concentration (CBV; primary motor area and area surrounding the primary motor area). Units on the axes are mmol/l. In addition, Series 1 shows the trajectory for 5 s before the task; Series 2, the trajectory for 36 s during the task; and Series 3, the trajectory for 55 s after the task. The task here is lifting a 14.5 kg dumbbell.

Figure 48:
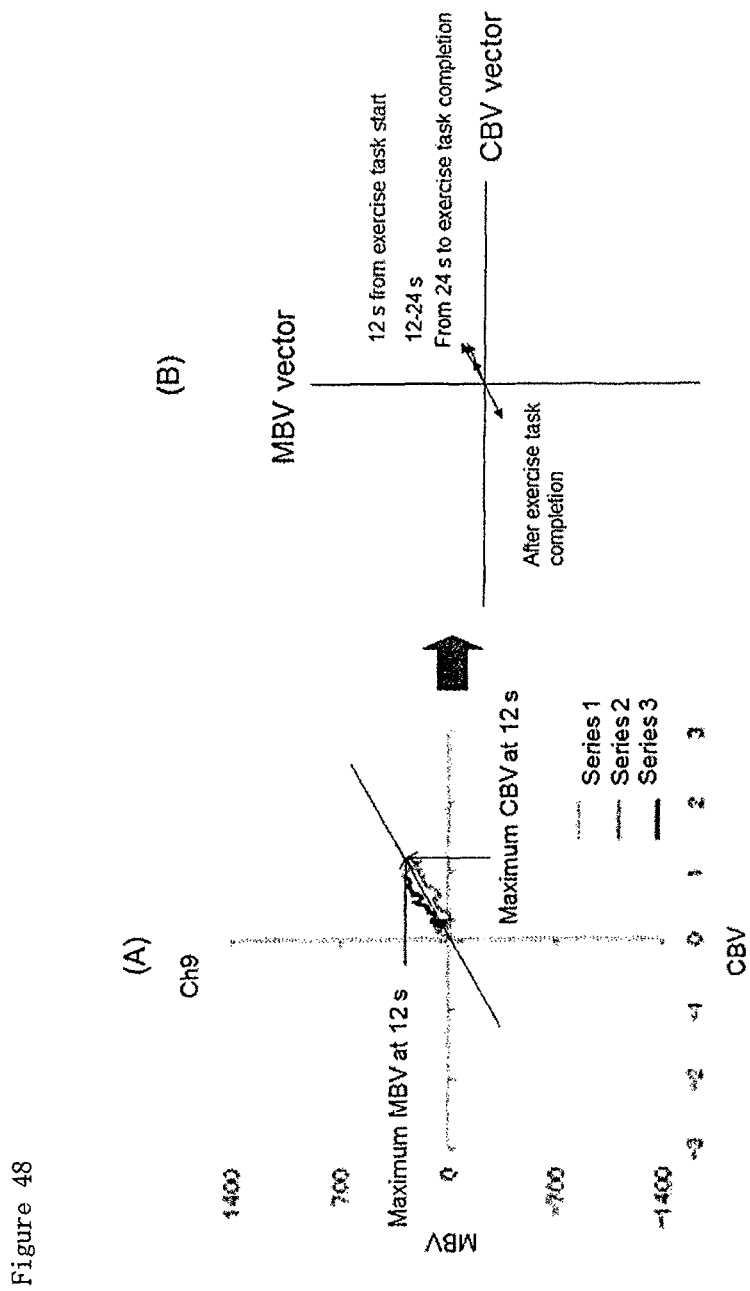
FIG. 48(A) is a detail view of FIG. 47 showing the diagram for Channel 9 (Ch9), and (B) is a view of a vector representation of the movement (linear) of BV over time. The vertical axis here is change in muscle blood volume (MBV; upper arm biceps), and the horizontal axis is change in cerebral blood volume concentration (CBV; primary motor area).

FIG. 48(A) is a detail view of FIG. 47 showing the diagram for Channel 9 (Ch9), and (B) is a view of a vector representation of the movement (linear) of BV over time. The vertical axis here is change in muscle blood volume (MBV; upper arm biceps), and the horizontal axis is change in cerebral blood volume concentration (CBV; primary motor area). Units on the axes are mmol/l.

As can be seen from FIG. 48(A), for the index BV, the peak times for MBV and CBV coincide.

In addition, according to the vector representation shown in FIG. 48(B), [the vectors] can be seen to show the same direction during the task, and directly opposite directions when the task is completed.

Figure 49:
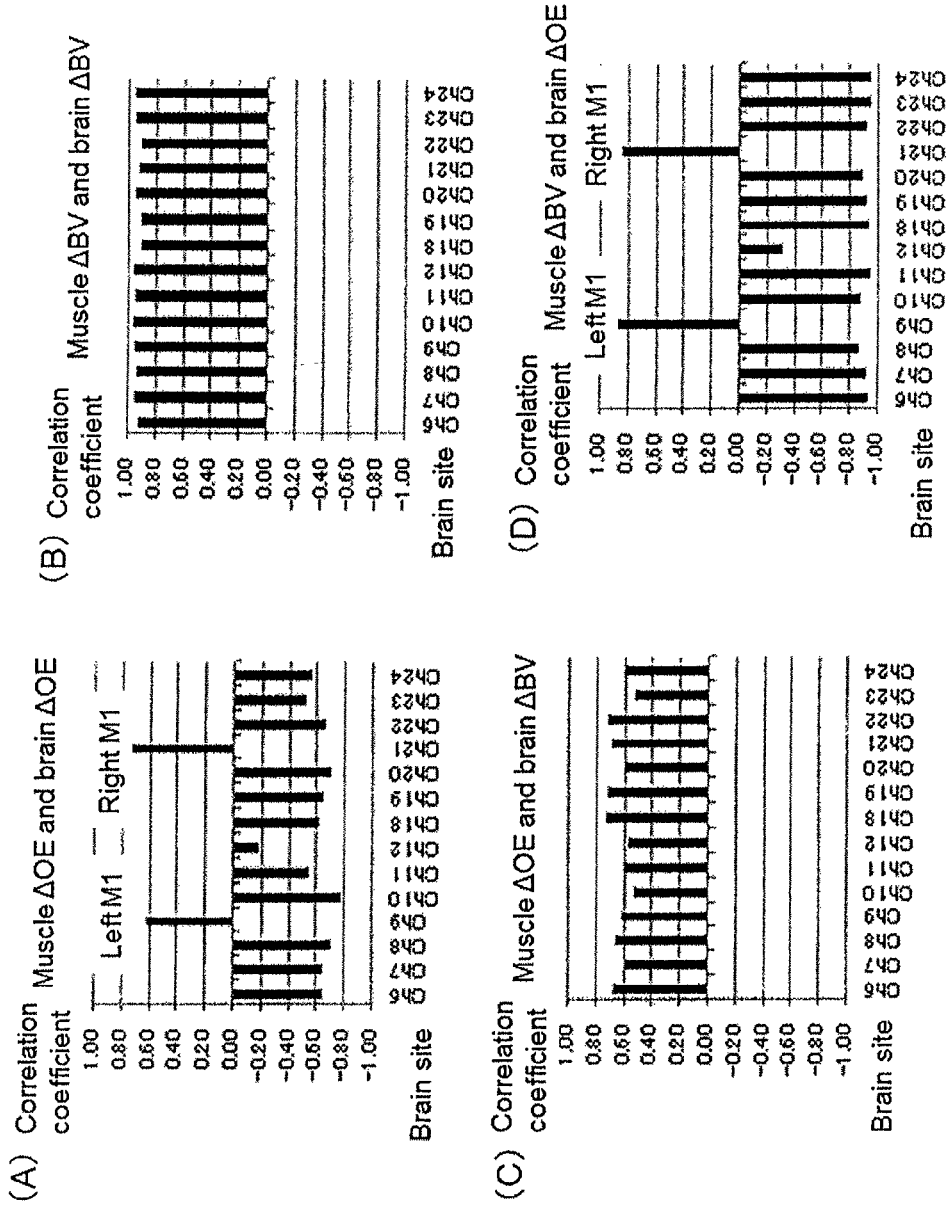
FIG. 49 shows graphs of correlation coefficients for the indices ΔOE and ΔBV, from one location on the right upper arm biceps and from sites at 14 points in the brain (Channels [Ch6-Ch12] in the left brain, Channels 18-24 [Ch18-Ch24] in the right brain), over 36 s during a task of lifting a 14.5 kg dumbbell with both hands: (A) shows correlation coefficients between muscle ΔOE and brain ΔOE; (B) shows correlation coefficients between muscle ΔBV and brain ΔBV; (C) shows correlation coefficients between muscle ΔOE and brain ΔBV; and (D) shows correlation coefficients between muscle ΔBV and brain ΔOE.

FIG. 49 shows graphs of correlation coefficients for the indices ΔOE and ΔBV, from one location on the right upper arm biceps and from sites at 14 points in the brain (Channels [Ch6-Ch12] in the left brain, Channels 18-24 [Ch18-Ch24] in the right brain), over 36 s during a task of lifting a 14.5 kg dumbbell with both hands: (A) shows correlation coefficients between muscle ΔOE and brain ΔOE; (B) shows correlation coefficients between muscle ΔBV and brain ΔBV; (C) shows correlation coefficients between muscle ΔOE and brain ΔBV; and (D) shows correlation coefficients between muscle ΔBV and brain ΔOE.

In FIG. 49(A), ΔOE shows positive correlations with correlation coefficients of 0.6 or higher at 2 points in the brain, but negative correlations at the other sites. This can be evaluated to mean that the only sites at which increased oxygen consumption in the brain coincides with increased oxygen consumption in the muscle are at Ch9 and Ch21 in the primary motor areas (M1).

In FIG. 49(B), ΔBV shows correlation coefficients of 0.8 or higher between the muscle and the 14 points in the brain. This shows that blood volume increases in the muscle and in the brain are rising together. This means that cerebral blood pressure and muscle blood pressure are rising simultaneously.

In FIG. 49(C), ΔOE in the muscle and ΔBV in the brain show correlation coefficient values of around 0.6.

In FIG. 49(D), ΔBV in the muscle and ΔOE in the brain show positive correlations at Channels 9 and 21, and negative correlations at the other brain sites. This shows that oxygen consumption is increasing in the primary motor area (M1) at Channels 9 and 21, associated with the perfusion and pumping up of the muscle. Furthermore, it shows that associated activity is occurring even at brain sites where oxygen consumption does not occur, reducing oxygen consumption.

Figure 50:
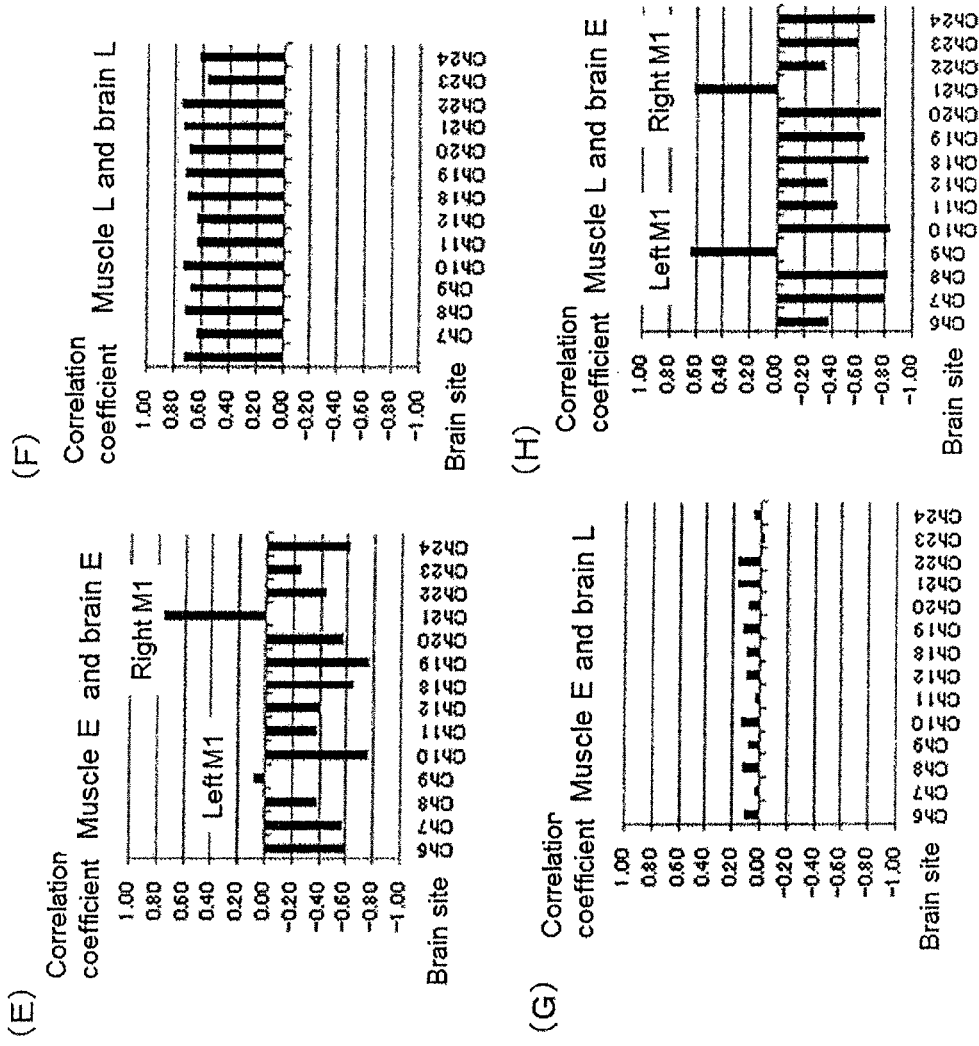
FIG. 50 shows graphs of correlation coefficients, with the ratio E and the value L as indices: (E) shows correlation coefficients between E for the muscle and E for the brain; (F) shows correlation coefficients between L for the muscle and L for the brain; (G) shows correlation coefficients between E for the muscle and L for the brain; and (H) shows correlation coefficients between L for the muscle and E for the brain.

FIG. 50 shows graphs of correlation coefficients, with the ratio E and the value L as indices: (E) shows correlation coefficients between E for the muscle and E for the brain; (F) shows correlation coefficients between L for the muscle and L for the brain; (G) shows correlation coefficients between E for the muscle and L for the brain; and (H) shows correlation coefficients between L for the muscle and E for the brain.

In FIG. 50(E), although Channel 21 in the right brain and Channel 9 in the left brain are both primary motor areas (M1), it is the Channel 21 primary motor area that can be evaluated as having a positive correlation for E of the muscle. This can be evaluated to mean that oxygen consumption efficiency of the muscle has a strong relationship with the oxygen consumption efficiency of the brain.

In FIG. 50(F), because the values for L for the brain and the muscle showed correlations of 0.6 or higher at all sites, they all responded in the same way with respect to this index, with no distinguishing characteristics.

In FIG. 50(G), there is no correlation whatsoever between E for the muscle and L for the brain, and they can be evaluated as independent phenomena. Namely, we can see that there was no relationship between how much the brain worked and the oxygen consumption efficiency of the muscle.

In FIG. 50(H), L for the muscle and E for the brain show positive correlations at Channels 9 and 21, and the other brain sites show negative correlations; this can be evaluated to mean that movement of the muscle is related to oxygen consumption efficiency of the brain.

Figure 51:
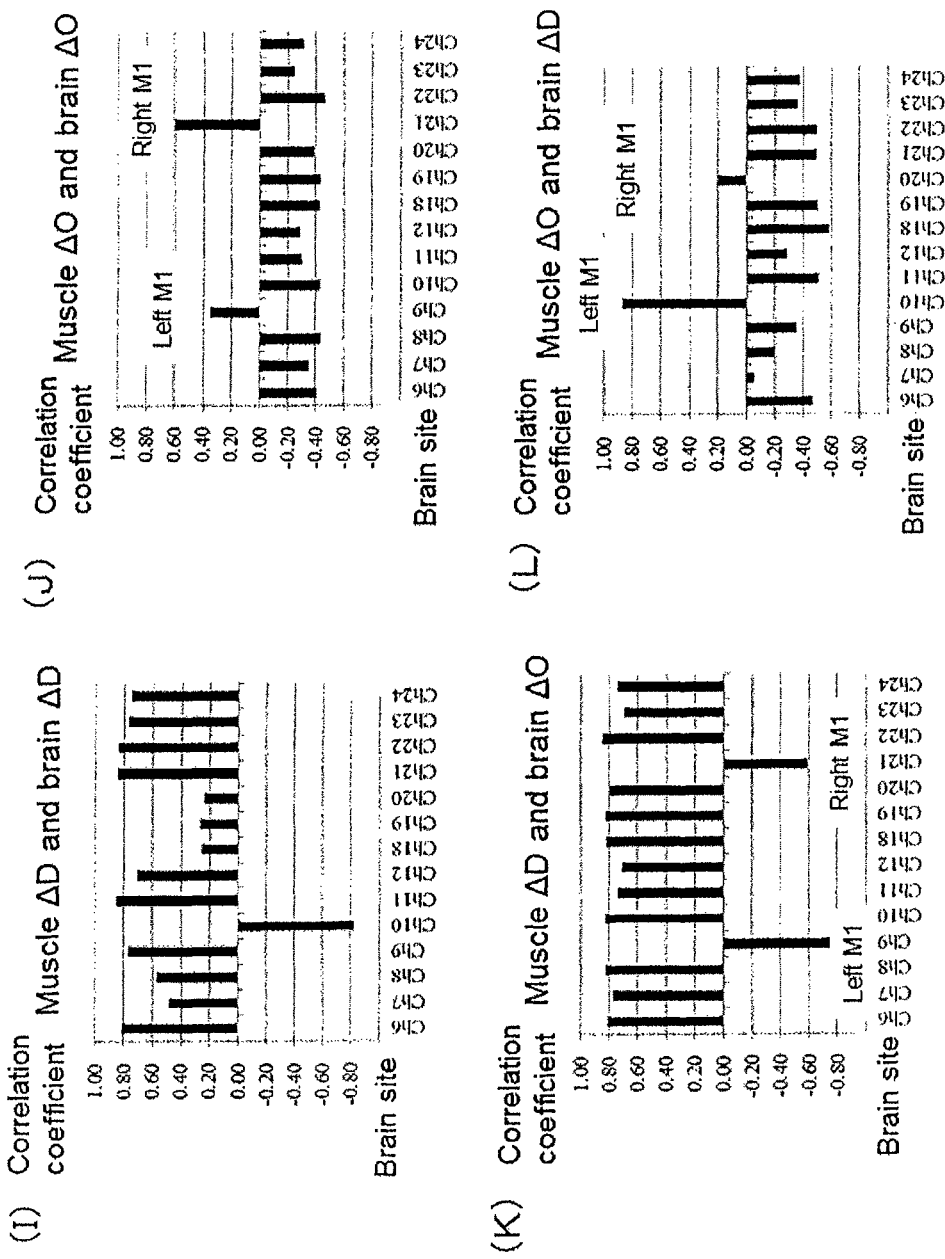
FIG. 51 shows graphs of correlation coefficients for the indices O (ΔO) and D (ΔD): (I) shows correlation coefficients between muscle ΔD and brain ΔD; (J) shows correlation coefficients between muscle ΔO and brain ΔO; (K) shows correlation coefficients between muscle ΔD and brain ΔO; and (L) shows correlation coefficients between muscle ΔO and brain ΔD.

FIG. 51 shows graphs of correlation coefficients for the indices O (ΔO) and D (ΔD): (I) shows correlation coefficients between muscle ΔD and brain ΔD; (J) shows correlation coefficients between muscle ΔO and brain ΔO; (K)

shows correlation coefficients between muscle ΔD and brain ΔO; and (L) shows correlation coefficients between muscle ΔO and brain ΔD.

In FIG. 51(I), it can be seen that changes in D in the muscle and the brain show correlations of −0.6 or higher except at Channel 10.

In FIG. 51(J), it can be seen that correlations of 0.6 are scarce for changes in O in the muscle and the brain.

In FIG. 51(K), changes in D in the muscle and O in the brain can be evaluated as being strongly correlated. In particular, the "signs" of the correlations (positive or negative) differ between the primary motor areas (M1) and their surrounding areas.

In FIG. 51(L), only Channel 10 showed a high correlation between O in the muscle and D in the brain. Although Channel 10 shows a different dynamic from the primary motor areas (M1) and their surrounding areas, it can be seen to have a relationship with muscle exercise.

Figure 52:
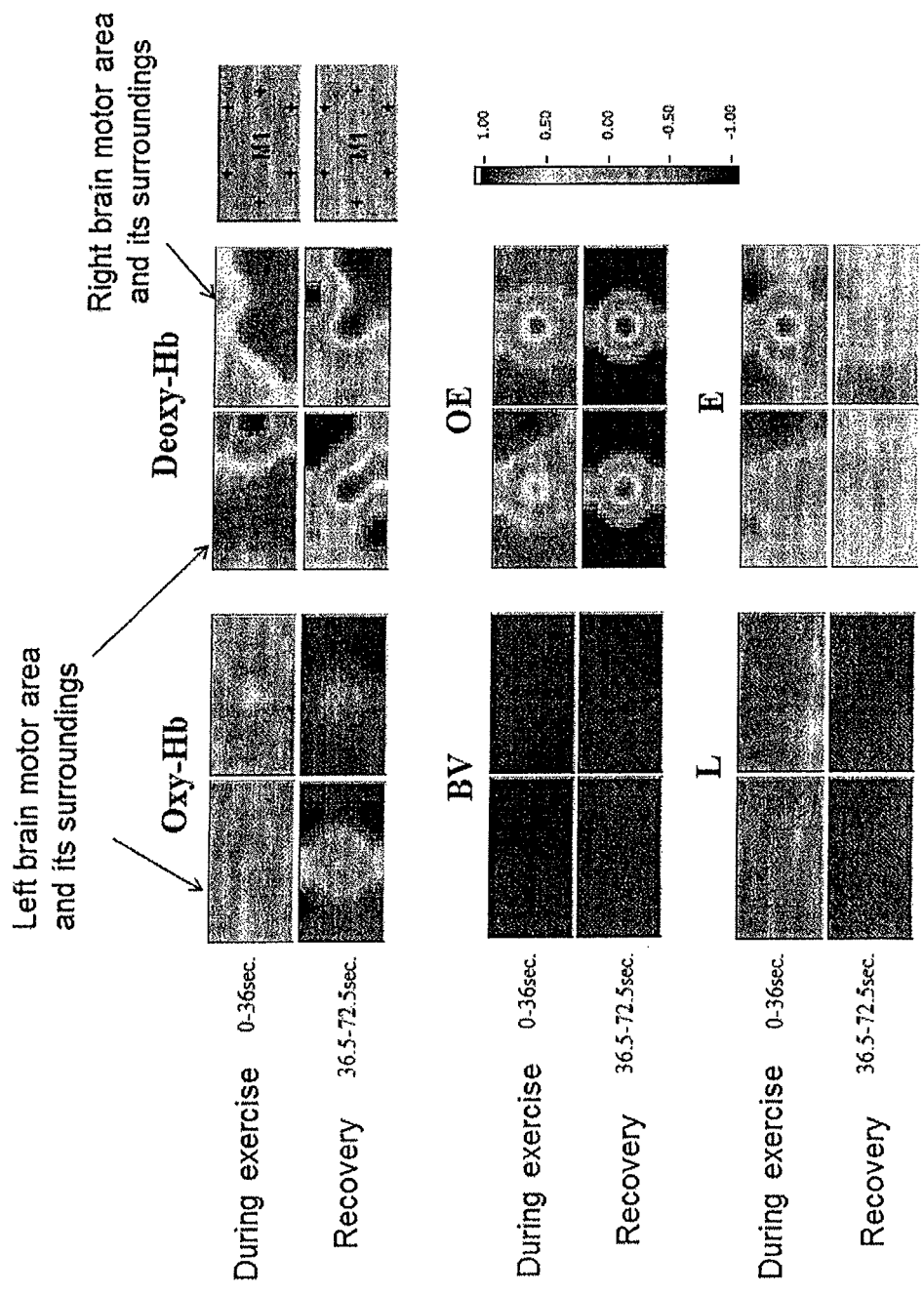
FIG. 52 is a figure representing time series changes in correlation coefficients for the physiological indices O, D, OE, BV, L and angle E of the muscle and the brain, displayed by color-coding from −1.0 to 1.0.

FIG. 52 is a figure representing time series changes in correlation coefficients for the physiological indices O, D, OE, BV, L and angle E of the muscle and the brain, displayed by color-coding from −1.0 to 1.0. Color-coding is done by changing the color according to the correlation coefficient, such as, for example: red (correlation coefficient 1.0), orange (correlation coefficient 0.75), yellow (correlation coefficient 0.5), green (correlation coefficient 0.0), light blue (correlation coefficient −0.75), blue (correlation coefficient −1.0).

In FIG. 52, an arrangement of 7 channels is visualized in each frame; the 2 frames on the left show the 7 channels of the left brain (Channels 6-12), and those on right show the 7 channels of the right brain (Channels 18-24).

The images in FIG. 52 are hybrid imaging, in which a function is simultaneously visualized from different sites of a living body, making it possible to evaluate not only commands from the brain to the muscle but also the feedback system between the muscle and the brain.

Namely, interactions between the indices of a plurality of brain sites and muscle exercise can be evaluated from the relationships between correlation coefficients between the muscle and the brain. This makes it possible to selectively cause oxygen consumption at sites in the brain by adjusting amounts of exercise and exercise times and routines while watching the muscle indices, enabling brain activity and brain training With previous techniques such as electromyography, the metabolic state of a muscle cannot be evaluated when it is not moving, but with the present invention, simultaneous measurements of the brain and the muscle make it possible to evaluate the state of the brain and the muscle in the recovery process.

In FIG. 52, the most striking changes appear in the images for oxygen exchange (OE). In the images for OE, values for OE are high in both the primary motor area of the brain and in the muscle. With reference to the graph of FIG. 49(A), this can be evaluated to mean that there are sites in the brain that use oxygen to send commands for the muscle to work, and those sites are the primary motor areas (M1). Namely, it can be seen that the orange sites are the brain sites where the most oxygen is being consumed, and they are furthermore closely related to muscle exercise.

Because the areas surrounding the primary motor areas show the opposite color, blue at this time, the images can be evaluated to mean that the brain sites outside of M1 show the exact opposite action—not using oxygen—in association with the action of the muscle.

In this way, it can be seen that there is not necessarily one single brain site that supports the movement of the muscle; sites not directly involved also act indirectly in such a way as to smooth the way for brain activity by not using oxygen. This tendency is also seen in the recovery period.

On the other hand, as regards blood volume, all the sites show high blood pressure in almost exactly the same way.

[Two-Dimensional Diagrams of the Brain and the Muscle Using the Angle E]

The angle formed between the angle E of the brain and the angle E of the muscle is defined as the hybrid angle E (EH, or double angle E).

$$\begin{aligned} \text{Hybrid angle } E\ (EH) &= \arctan(E_m/E_b) \\ &= \arctan\{(MOE/MBV)/(COE/CBV)\} \\ &= \arctan\{(MOE \times CBV)/(MBV \times COE)\} \end{aligned}$$

(Equation 47)

Figure 53:
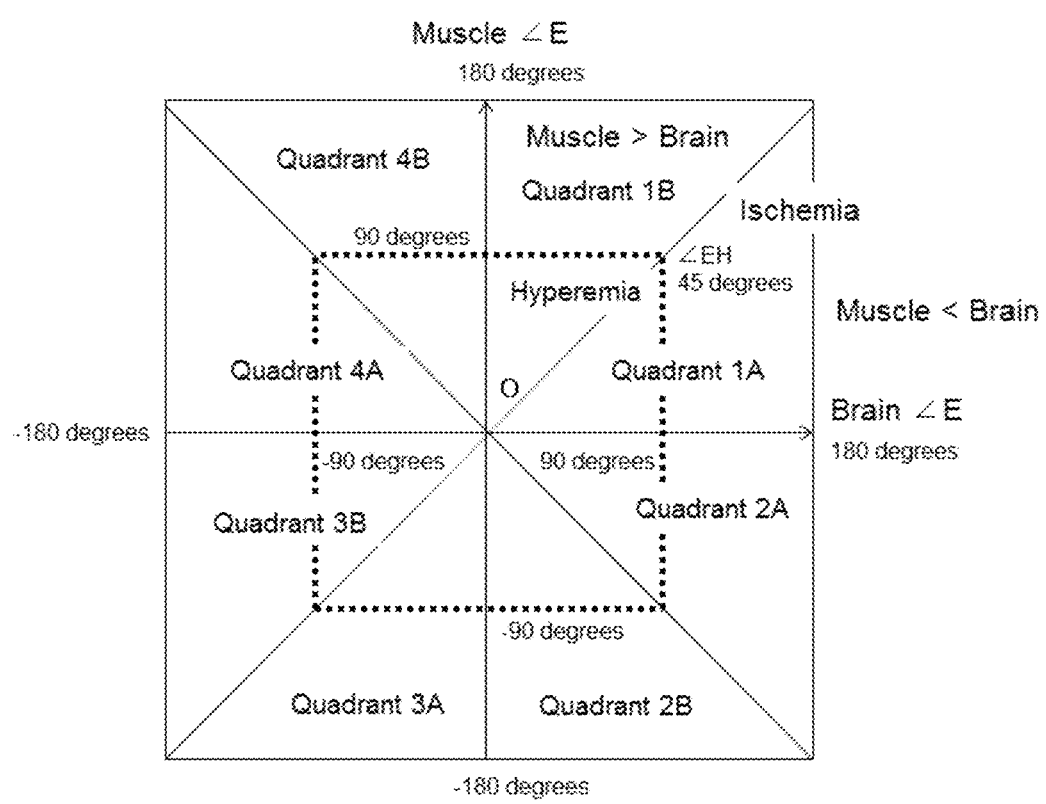
FIG. 53 is a two-dimensional diagram obtained by plotting simultaneous measurements over time, in which the horizontal axis is angle E (degrees) of the brain (primary motor area M1 of the brain) and the vertical axis is angle E (degrees) of the muscle (biceps of the arm).

FIG. 53 is a two-dimensional diagram obtained by plotting simultaneous measurements over time, in which the horizontal axis is angle E (degrees) of the brain (primary motor area M1 of the brain) and the vertical axis is angle E (degrees) of the muscle (biceps of the arm).

By means of EH, which is formed by the ratio between E of the muscle and E of the brain, obtained from the two-dimensional diagram shown in FIG. 53, interrelationships between the muscle and the brain can be classified into 8 sub-quadrants and evaluated and imaged, quantitatively and over time.

In FIG. 53, in Quadrant 1, oxygen exchange efficiency is high with respect to changes in hemoglobin, in both the brain and the muscle. In Quadrant 1B, the muscle is working more efficiently than the brain, and in Quadrant 1A, the brain is working more efficiently than the muscle.

In Quadrant 2, muscle activity is reduced and the brain is working efficiently.

In Quadrant 3, activity is reduced in both the brain and the muscle.

In Quadrant 4, brain activity is reduced and the muscle is working efficiently.

Figure 54:
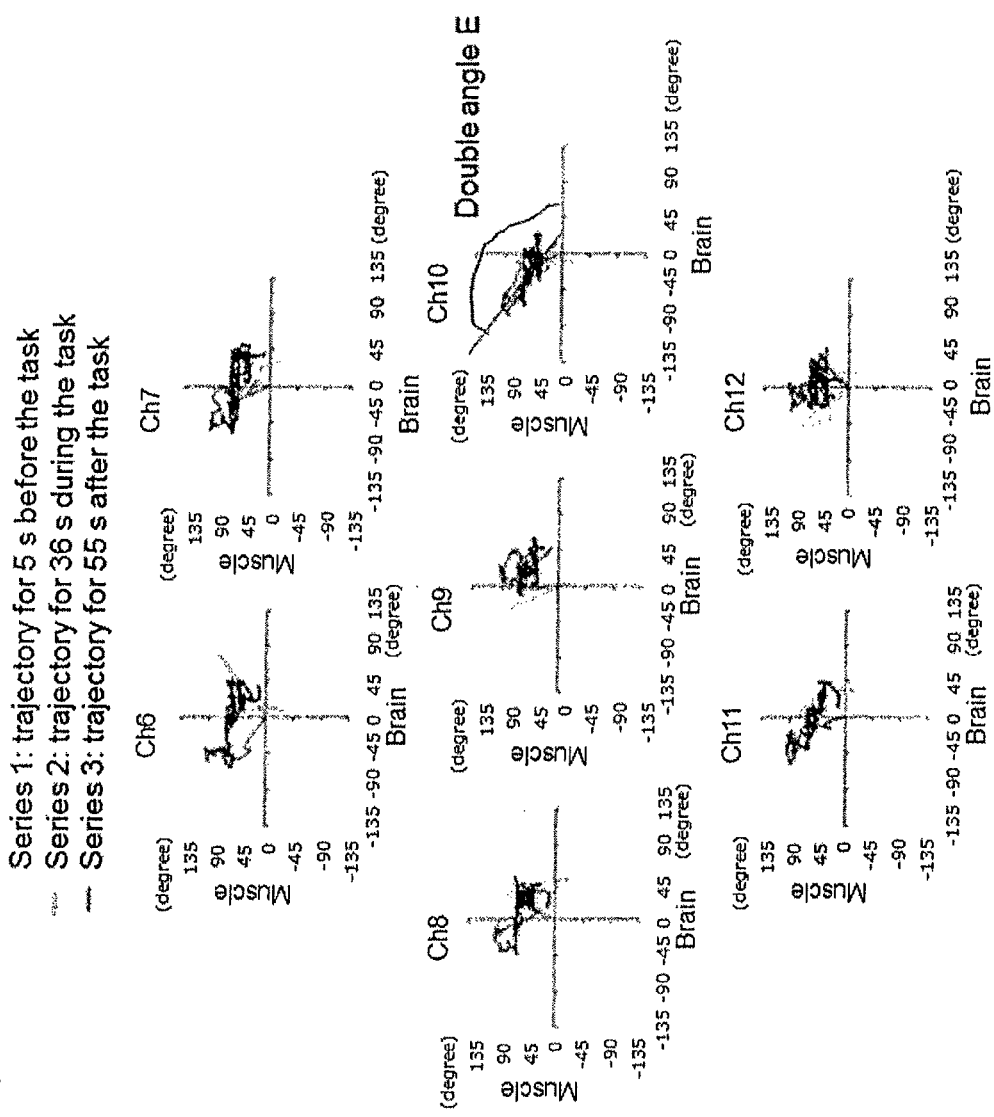
FIG. 54 is two-dimensional diagrams of Channels 6-12 (Ch6-Ch12), using the respective angles E of the muscle and the brain.

FIG. 54 is two-dimensional diagrams of Channels 6-12 (Ch6-Ch12), using the respective angles E of the muscle and the brain. Here, the vertical axis is E (degrees) of the muscle and the horizontal axis is ∠E (degrees) of the brain.

In addition, Series 1 shows the trajectory for 5 s before a task; Series 2, the trajectory for 36 s during a task (such as lifting a dumbbell); and Series 3, the trajectory for 55 s after the task.

The task here is lifting a 14.5 kg dumbbell.

Figure 55:
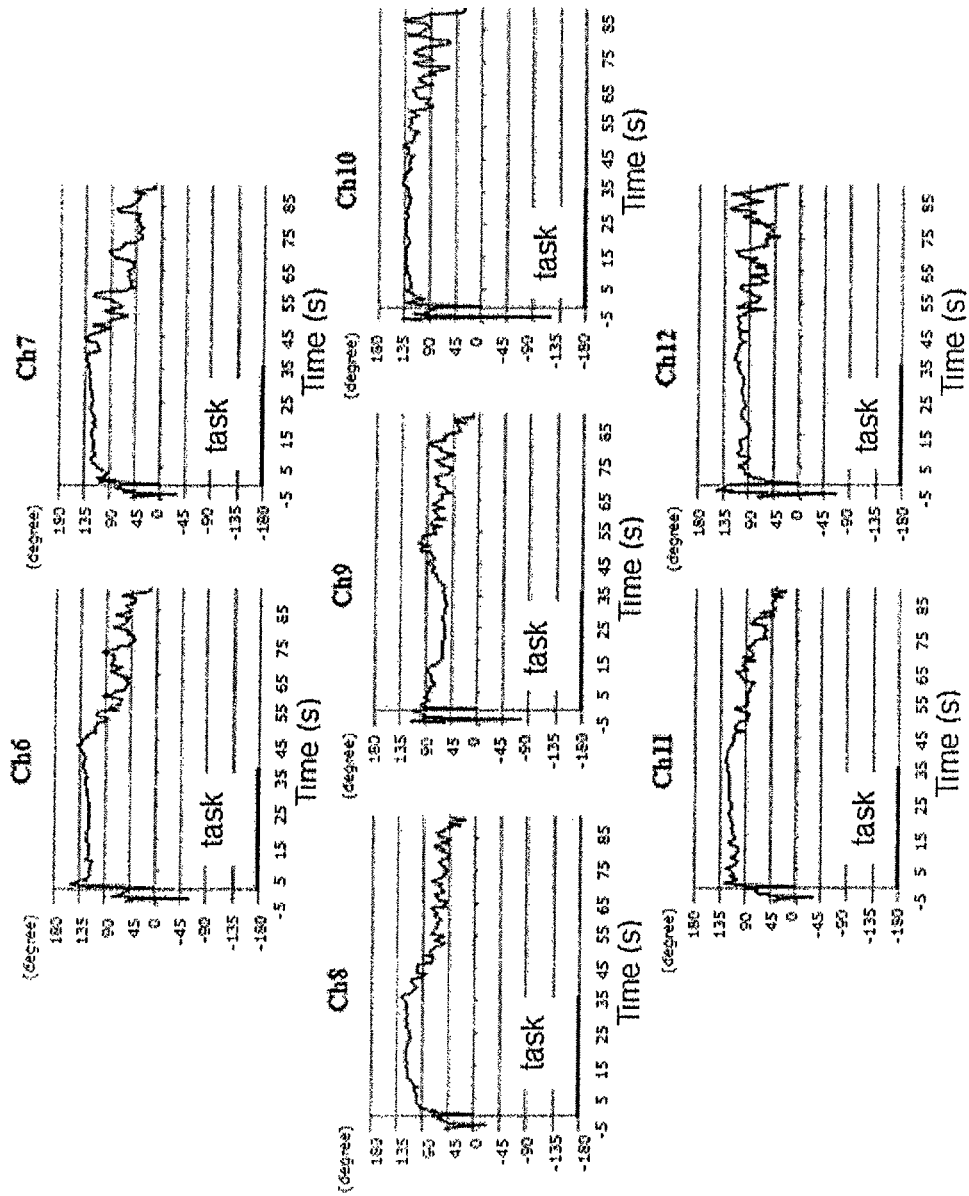
FIG. 55 is graphs showing time series changes in EH angle for Channels 6-12 (Ch6-Ch12).

FIG. 55 is graphs showing time series changes in ∠EH angle for Channels 6-12 (Ch6-Ch12). Here, the horizontal axis is time (s), and the vertical axis is ∠EH. In addition, the bold line along the horizontal axis shows the time of the task.

It can be seen from FIG. 55 that Channel 9 shows an ∠EH of 45-90 degrees during the task, in Quadrant 1B; and the other sites show angles EH of 90-135 degrees during the task, in Quadrant 4B.

Figure 56:
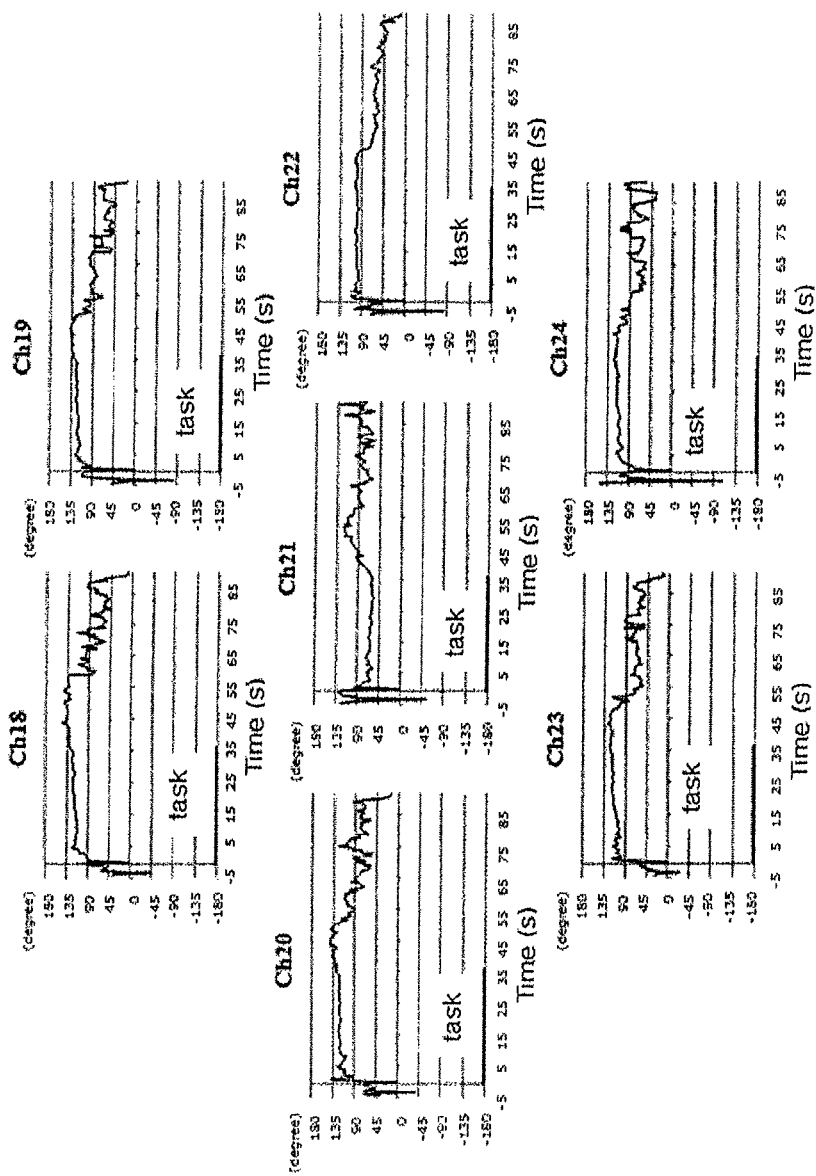
FIG. 56 is graphs showing time series changes in EH angle for Channels 18-24 (Ch18-Ch24).

FIG. 56 is graphs showing time series changes in ∠EH angle for Channels 18-24 (Ch18-Ch24). Here, the horizontal axis is time (s), and the vertical axis is ∠EH.

In addition, the bold line along the horizontal axis shows the time of the task.

It can be seen from FIG. 56 that Channel 21 shows an ∠EH of 45-90 degrees during the task, in quadrant 1B; and the other sites show angles EH of 90-135 degrees during the task, in quadrant 4B.

In this way, from the situations on a two-dimensional diagram showing the respective oxygen exchange efficiency of organs or sites, it is possible to read and evaluate the interrelationships between their respective angles EH. From this muscle-to-brain ∠E ratio on a two-dimensional vector diagram, using ∠E from the muscle and brain, interrelationships between the brain and muscle can be classified into 8 sub-quadrants, and evaluated and imaged, quantitatively and over time. In addition, relationships between the working of the muscle and brain become clear, quadrant by quadrant.

In addition, it is possible to make changes in an exercise by viewing the task load from the standpoint of oxygen efficiency and seeing whether it is having enough effect on the brain and the muscle.

Figure 57:
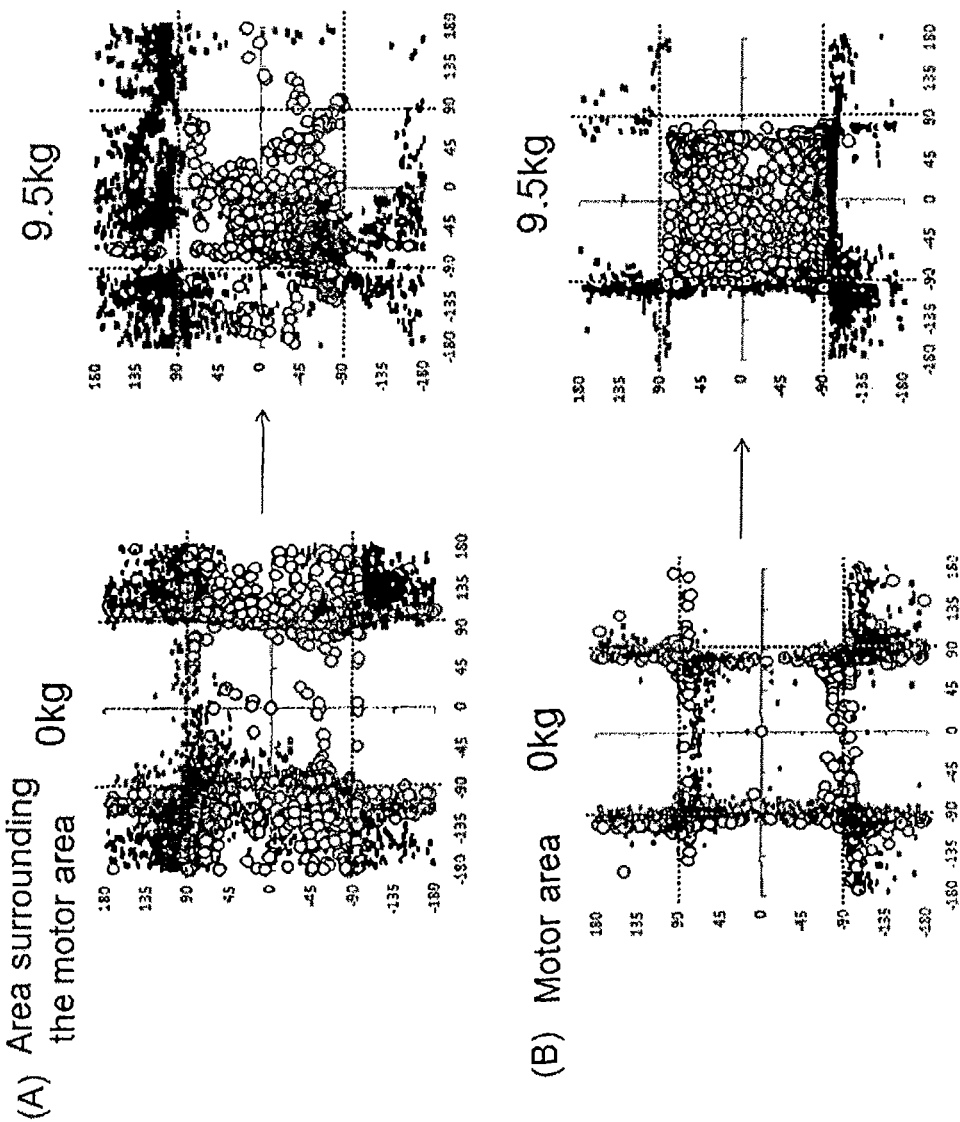
FIG. 57(A) is a two-dimensional diagram obtained by plotting simultaneous measurements over time, before and after lifting a 9.5 kg dumbbell, in which the horizontal axis is E (degrees) of the brain (area surrounding the primary motor area of the brain) and the vertical axis is E (degrees) of the muscle (biceps of the arm); (B) is a two-dimensional diagram obtained by plotting simultaneous measurements over time, before and after lifting a 9.5 kg dumbbell, in which the horizontal axis is E (degrees) of the brain (primary motor area of the brain) and the vertical axis is E (degrees) of the muscle (biceps of the arm).

FIG. 57(A) is a two-dimensional diagram obtained by plotting simultaneous measurements over time, before and after lifting a 9.5 kg dumbbell, in which the horizontal axis is ∠E (degrees) of the brain (area surrounding the primary motor area of the brain) and the vertical axis is ∠E (degrees) of the muscle (biceps of the arm); (B) is a two-dimensional diagram obtained by plotting simultaneous measurements over time, before and after lifting a 9.5 kg dumbbell, in which the horizontal axis is ∠E (degrees) of the brain (primary motor area of the brain) and the vertical axis is ∠E (degrees) of the muscle (biceps of the arm). In the Figure, open circles (○) are data from during the task, and filled circles (●) are data from before and after the task.

As can be seen from FIGS. 57(A) and (B), at the motor area and its surrounding sites, the plots are concentrated in a range bounded by from +90 degrees to −90 degrees as the dumbbell weight is lifted. In particular, for the 9.5 kg dumbbell exercise, we can see that they are concentrated in the region bounded by 0 and 90 degrees.

The fact that there is a high probability that [∠E] is within 90 degrees during the task shows that, because [the area] within 90 degrees indicates high blood volume, pressure in both the brain and the muscle is rising, and the exercise is being done in a state of increased blood volume.

Conversely, it can be said that outside this frame, the load was still such that a response was possible without a regulatory response increasing the blood volume, but with an exercise of lifting the 9 kg dumbbell, the task becomes harder to the point of a regulatory response increasing the blood volume, and the situation is one in which both the muscle and brain are being worked hard.

[Technique 2 for Composite Visualization and Imaging of Physiological Indices]

Figure 58:
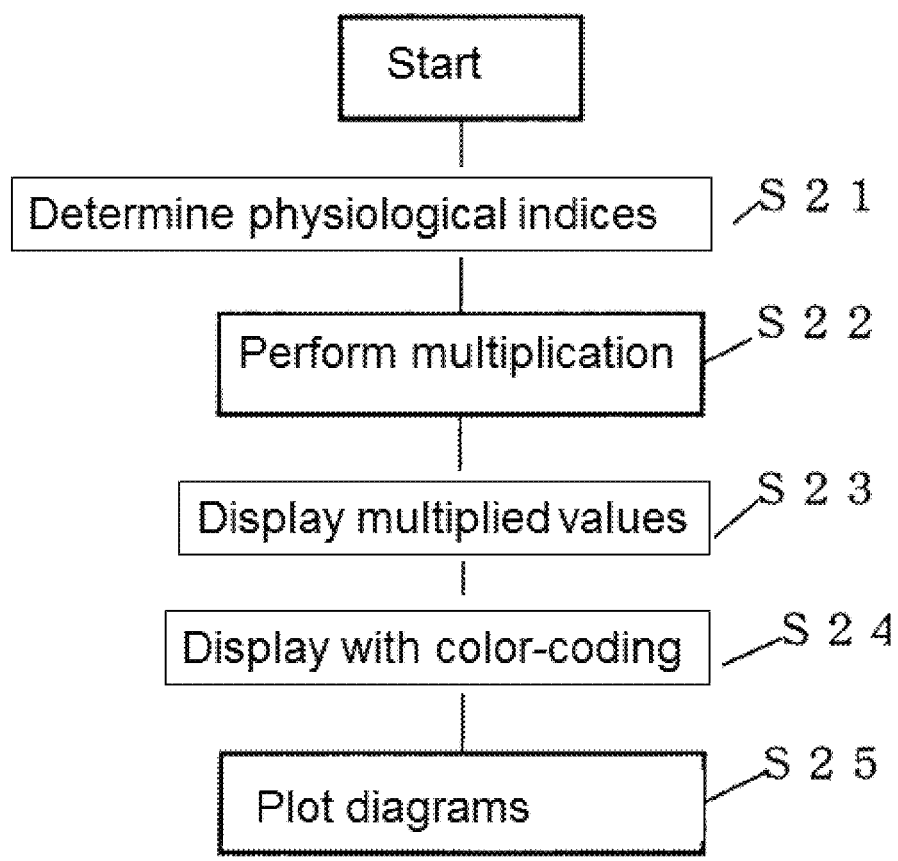
FIG. 58 is a flowchart illustrating the steps in Technique 2 for hybrid imaging.

FIG. 58 is a flowchart illustrating the steps in Technique 2 for hybrid imaging.

First, using the apparatus for evaluating physiological function of the embodiment of the present invention, values for physiological indices such as, for example, O (change in oxyhemoglobin), D (change in deoxyhemoglobin), OE (change in oxygen exchange), BV (change in blood volume), the ratio E (ratio of oxygen exchange to blood volume) and L (distance within a phase), are determined for the brain and the muscle (Step S21).

Next, multiplication by site is performed for each physiological index by means of calculating part 10 (Step S22).

Next, the multiplied values are displayed as time series on display part 9 (Step S23).

Next, the values multiplied by site are displayed on display part 9, color-coded by value (Step S24).

Next, the multiplied values for OE and the multiplied values for BV, for example, are plotted on an OE/BV two-dimensional diagram (Step S25).

This is hybrid imaging of brain and muscle activity, utilizing multiplied values for physiological indices.

Evaluating Two-Dimensional Diagrams Using Products of OE and BV of the Muscle and the Brain Simultaneous measurement of the muscle and brain makes it possible to show the maximum values for OE products and BV products. The motor region that contributes to moving the right upper arm biceps becomes clear from the OE products.

The angle formed by the OE and BV products is defined as a hybrid angle, by Equation 48, below:

$$\text{Hybrid angle }(\angle H)=\arctan\{(MOE \times COE)/(MBV \times CBV)\} \quad \text{(Equation 48)}$$

The hybrid angle (∠H angle) represents oxygen exchange efficiency of the brain and muscle working together simultaneously, and an angle of from 0 to 90 degrees shows that they are working efficiently.

Figure 59:
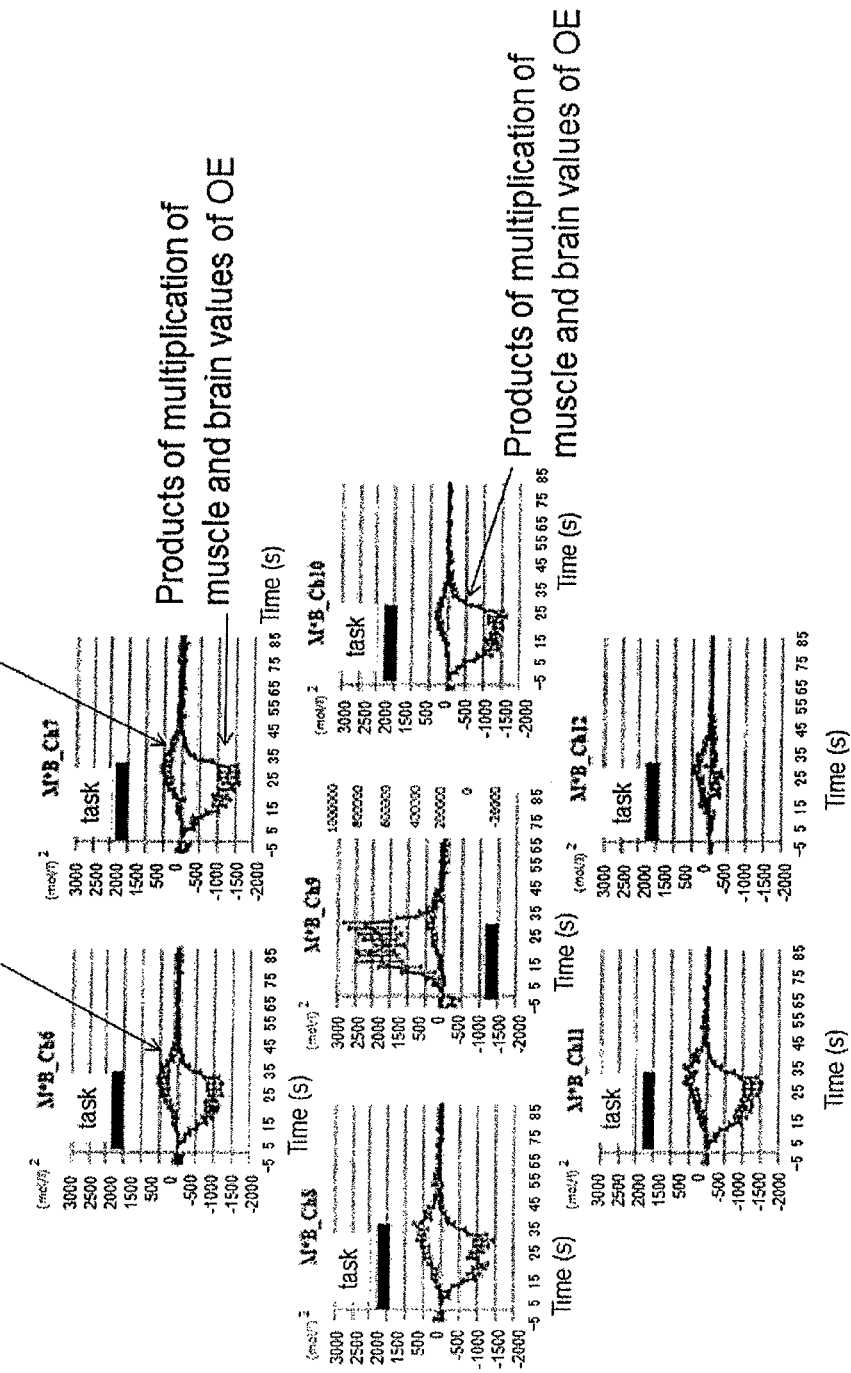
FIG. 59 is graphs showing time series changes in products of multiplying concentration changes in blood volume (MBV×CBV) and products of multiplying concentration changes in oxygen exchange (MOE×COE), which are obtained from the muscle (biceps of the arm) and from the left brain primary motor area and its surrounding area (Channels 6-12 [Ch6-Ch12]), upon performance of a task of lifting a 14.5 kg dumbbell.

FIG. 59 is graphs showing time series changes in products of multiplying concentration changes in blood volume (MBV×CBV) and products of multiplying concentration changes in oxygen exchange (MOE×COE), which are obtained from the muscle (biceps of the arm) and from the left brain primary motor area and its surrounding area (Channels 6-12 [Ch6-Ch12]), upon performance of a task of lifting a 14.5 kg dumbbell. The horizontal axis is time (s), and the vertical axis is BV products and OE products. The heavy black line parallel to the horizontal axis shows the time of the task.

Figure 60:
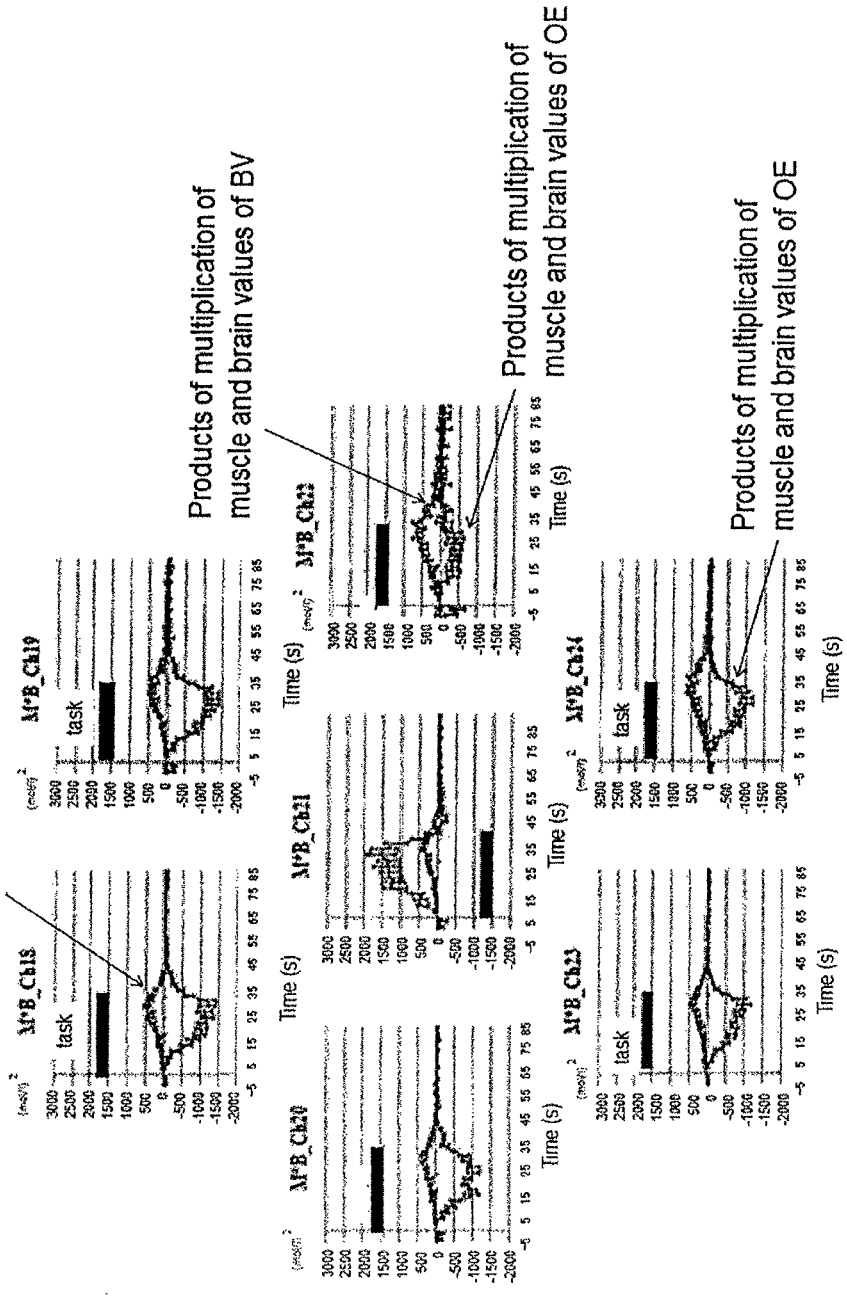
FIG. 60 is graphs showing time series changes in products of multiplying concentration changes in blood volume (MBV×CBV) and products of multiplying concentration changes in oxygen exchange (MOE×COE), which are obtained from the muscle (biceps of the arm) and from the right brain primary motor area and its surrounding area (Channels 18-24 [Ch18-Ch24]), upon performance of a task of lifting a 14.5 kg dumbbell.

FIG. 60 is graphs showing time series changes in products of multiplying concentration changes in blood volume (MBV×CBV) and products of multiplying concentration changes in oxygen exchange (MOE×COE), which are obtained from the muscle (biceps of the arm) and from the right brain primary motor area and its surrounding area (Channels 18-24 [Ch18-Ch24]), upon performance of a task of lifting a 14.5 kg dumbbell. The horizontal axis is time (s), and the vertical axis is BV products and OE products. The heavy black line [parallel to] the horizontal axis shows the time of the task.

Figure 61:
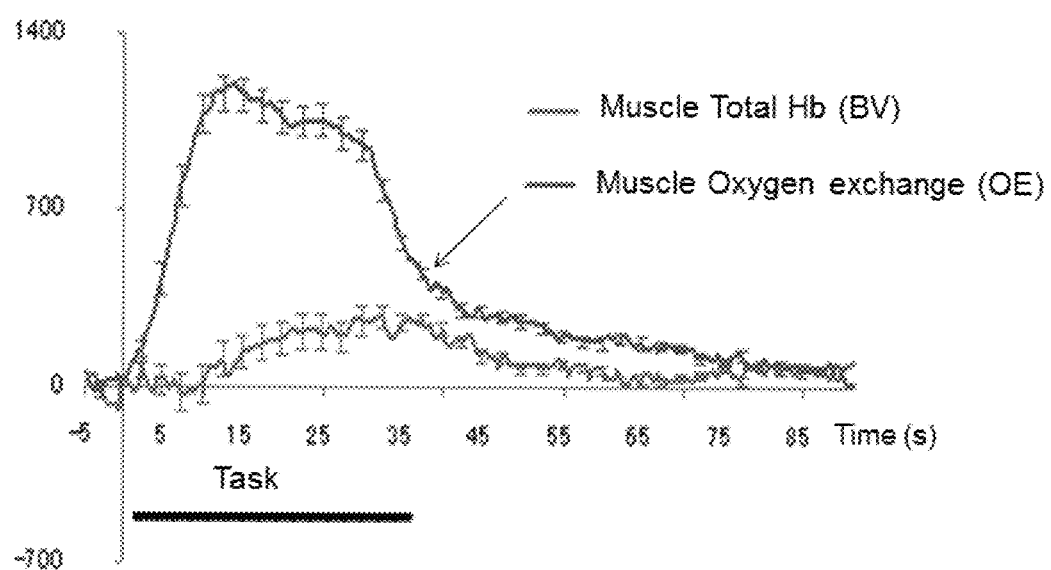
FIG. 61 is a graph showing time series changes in MBV and MOE of the muscle.

FIG. 61 is a graph showing time series changes in MBV and MOE of the muscle. The horizontal axis is time (s), and the vertical axis is MBV and MOE. The bold line parallel to the horizontal axis shows the time of the task.

Figure 62:
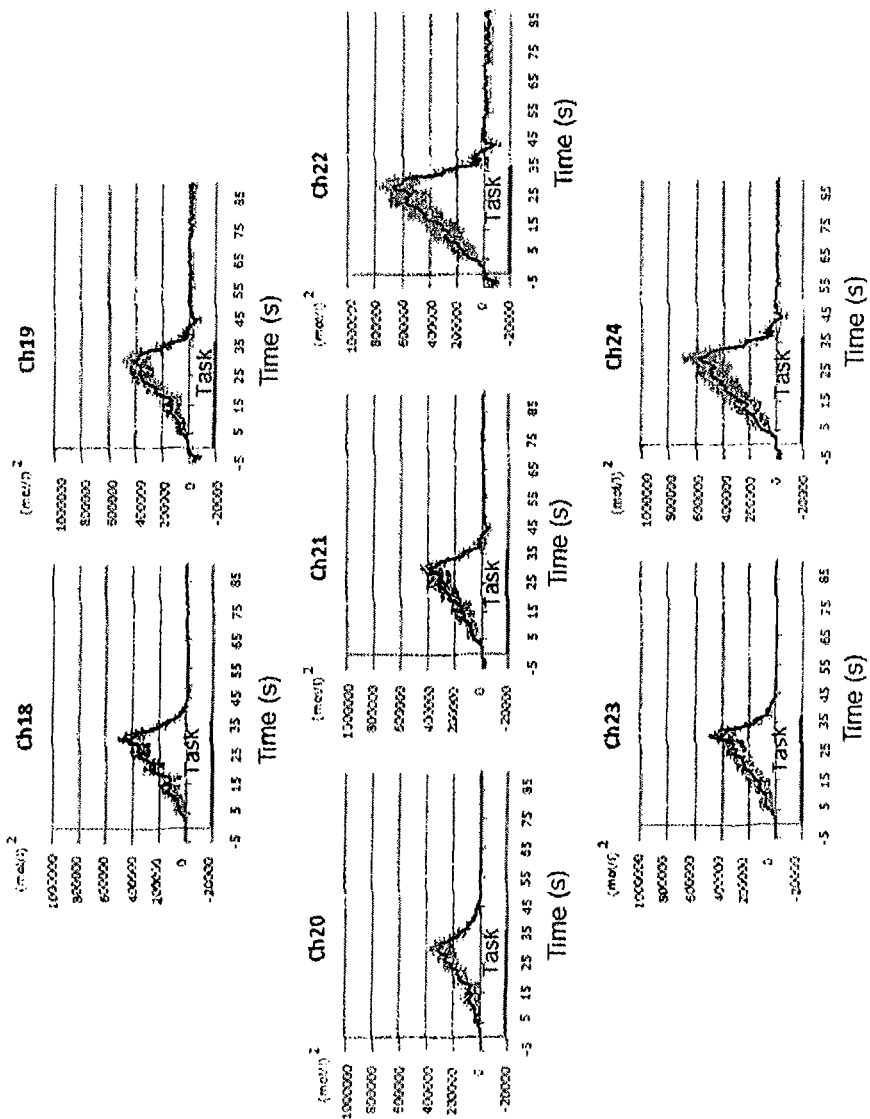
FIG. 62 is graphs showing time series changes in the products of multiplying oxygen exchange concentration changes in the muscle (biceps of the arm) and blood volume concentration changes in the right brain primary motor area and its surroundings (Channels 18-24 [Ch18-Ch24]) (MOE× CBV), upon performance of a task of lifting a 14.5 kg dumbbell.

FIG. 62 is graphs showing time series changes in the products of multiplying oxygen exchange concentration changes in the muscle (biceps of the arm) and blood volume concentration changes in the right brain primary motor area and its surroundings (Channels 18-24 [Ch18-Ch24]) (MOE×CBV), upon performance of a task of lifting a 14.5 kg dumbbell. The horizontal axis is time (s), and the vertical axis is the products MOE×CBV. The heavy black line parallel to the horizontal axis shows the time of the task.

In FIG. 62, muscle OE and cerebral BV are increasing linearly during exercise, showing a positive correlation, and it can be seen from all channels that muscle exercise is causing the blood volume of the entire brain to increase.

Figure 63:
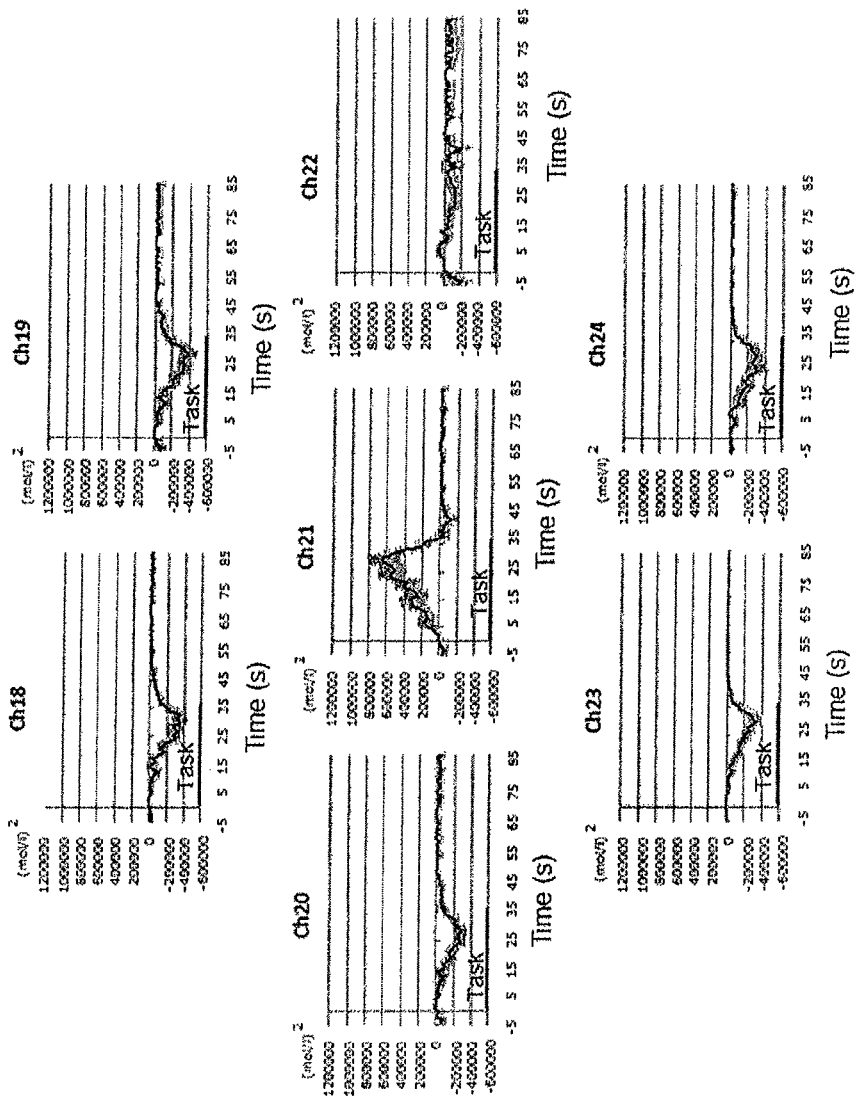
FIG. 63 is graphs showing time series changes in the products of multiplying blood volume concentration changes in the muscle (biceps of the arm) and oxygen exchange concentration changes in the right brain primary motor area and its surrounding area (Channels 18-24 [Ch18-Ch24]) (MBV×COE), upon performance of a task of lifting a 14.5 kg dumbbell.

FIG. 63 is graphs showing time series changes in the products of multiplying blood volume concentration changes in the muscle (biceps of the arm) and oxygen exchange concentration changes in the right brain primary motor area and its surrounding area (Channels 18-24 [Ch18-Ch24]) (MBV×COE), upon performance of a task of lifting a 14.5 kg dumbbell. The horizontal axis is time (s), and the vertical axis is MBV and COE. The bold line parallel to the horizontal axis shows the time of the task.

In FIG. 63, at Channel 21 of the primary motor area (M1), muscle blood volume MBV and cerebral oxygen exchange COE show linearity and a positive correlation during exercise, and the area surrounding the primary motor area (M1) shows negative correlations.

Figure 64:
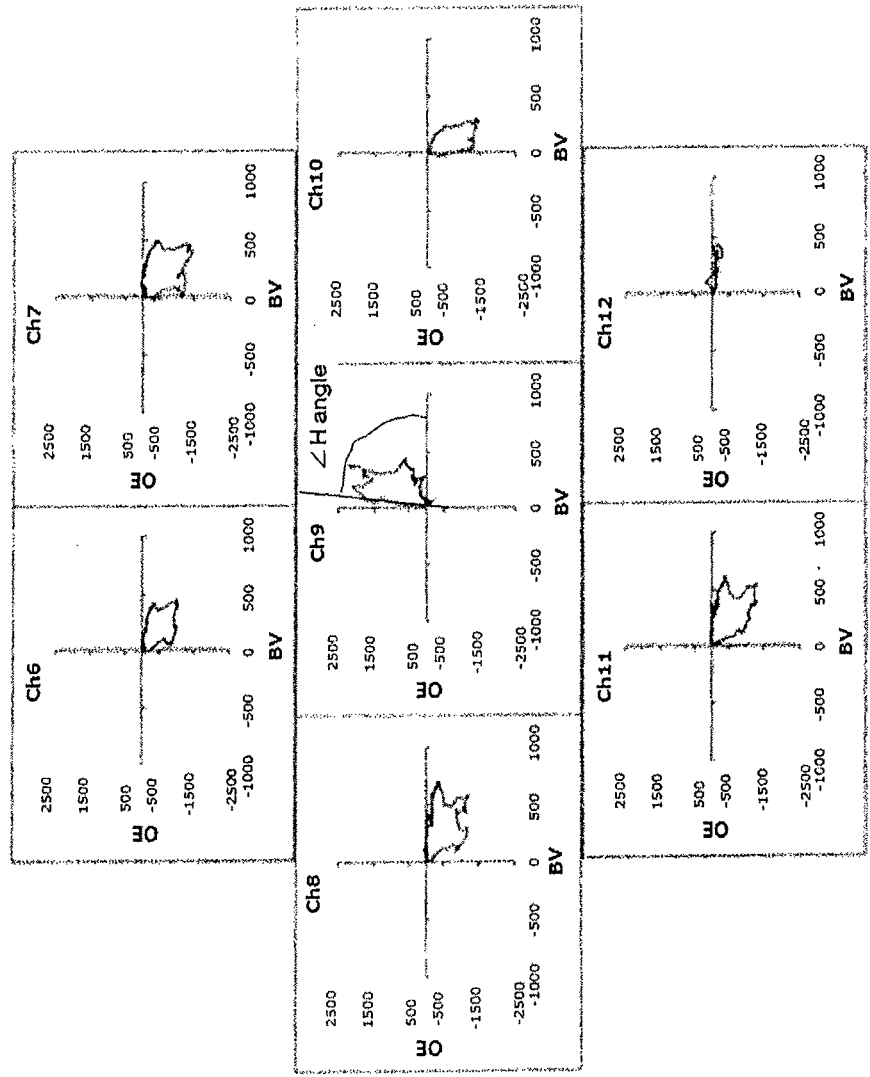
FIG. 64 is two-dimensional diagrams obtained by plotting simultaneous measurements over time, with products of multiplying blood volume concentration changes (MBV× CBV) as the horizontal axis and products of multiplying oxygen exchange concentration changes (MOE×COE) as the vertical axis, which are obtained from the muscle (biceps of the arm) and the left brain primary motor area and its surroundings (Channels 6-12 [Ch6-Ch12]), upon performance of a task of lifting a 14.5 kg dumbbell.

FIG. 64 is two-dimensional diagrams obtained by plotting simultaneous measurements over time, with products of multiplying blood volume concentration changes (MBV× CBV) as the horizontal axis and products of multiplying oxygen exchange concentration changes (MOE×COE) as the vertical axis, which are obtained from the muscle (biceps of the arm) and the left brain primary motor area and its surroundings (Channels 6-12 [Ch6-Ch12]), upon performance of a task of lifting a 14.5 kg dumbbell.

In the figure, "pre-task" shows the trajectory during 5 s before the task, "task" shows the trajectory over 36 s during the task, and "post-task" shows the trajectory during 55 s after the task.

In FIG. 64, the hybrid angle (H angle) at Channel 9 of the left brain primary motor area (M1) shows the most oxygen exchange efficiency during the task. The area surrounding Channel 9 shows, if anything, negative oxygen exchange efficiency, and a relationship of low oxygen exchange.

In addition, it is possible to see when the most efficient oxygen consumption occurred during the time when the 2 organs are working together (20 s).

[Evaluation Based on Two-Dimensional Diagrams Using Products of OE and BV of the Muscle and the Brain]

Because the load consumed by the brain and muscle [physiological oxygen consumption load (MOE×COE) or blood volume load (MBV×CBV)] represents a synthesis of the energy load from the center and the periphery of the living body, the ability to display and visualize it in real time is significant.

The following results are also clear:

1) Multiplied OE and multiplied BV do not peak at the same time.

2) Peaks for OE of the muscle and OE of the brain are not the same.

This evaluation has the following effects:

1) Timewise, it can be seen that the increase curves of BV and OE at the primary motor areas M1 (Channel 9 in the left brain and Channel 21 in the right brain) do not coincide during the task; the 2 indices are regulated independently (OE increases more rapidly than BV).

2) By measuring simultaneously, it can be seen, for example, that the increase in OE in the muscle is earlier than that in the brain, and it may act as a trigger for the increase in OE in the brain, and so on.

Imaging based on multiplication makes it possible to evaluate the amount of load (physiological oxygen consumption load) consumed by the brain and muscle.

3) BV×OE on a brain/muscle two-dimensional plane is a vector cross product; the power output by the brain and muscle is obtained by calculating the area. Using OE(ΔD− ΔO), new evaluations are made possible by multiplying OE loads, synthesizing the center and the periphery by reflecting the OE loads of both the brain and the muscle.

FIG. 65(A) is a color-coded view representing time series changes in the products of multiplying blood volume concentration changes (MBV×CBV), and (B) is a color-coded view representing time series changes in the products of multiplying oxygen exchange concentration changes (MOE×COE), which are obtained from the muscle (biceps of the arm) and the left brain primary motor area and its surrounding area (Channels 6-12 [Ch6-Ch12]), upon performance of a task of lifting a 14.5 kg dumbbell.

Figure 65:
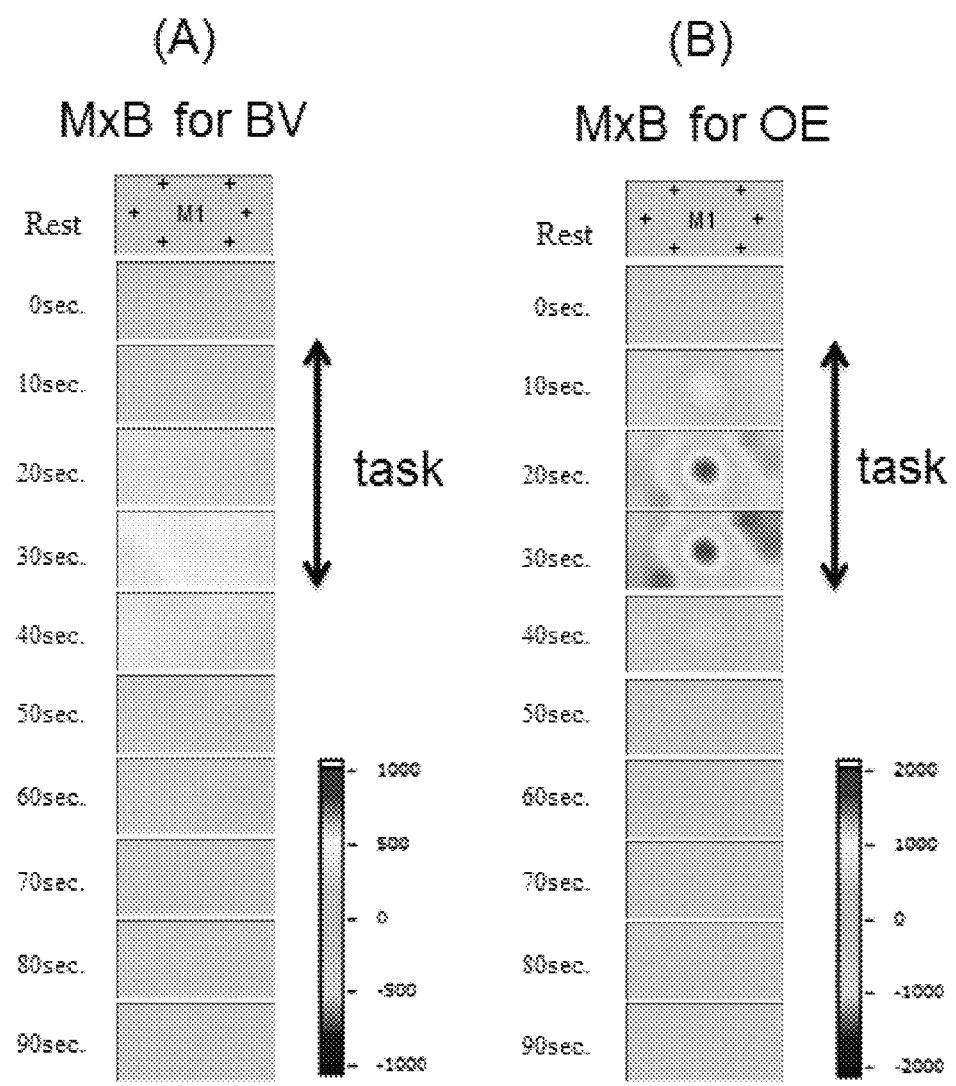
FIG. 65(A) is a color-coded view representing time series changes in the products of multiplying blood volume concentration changes (MBV×CBV), and (B) is a color-coded view representing time series changes in the products of multiplying oxygen exchange concentration changes (MOE×COE), which are obtained from the muscle (biceps of the arm) and from the left brain primary motor area and its surrounding area (Channels 6-12 [Ch6-Ch12]), upon performance of a task of lifting a 14.5 kg dumbbell.

In FIG. 65, an arrangement of 7 channels is visualized in each frame.

Color-coding in FIG. 65(A) is done, for example, by changing the color according to the magnitude of the product of multiplication as follows: red (product value 1000), orange (product value 750), yellow (product value 500), green (product value 0.0), light blue (product value −500), blue (product value −1000).

In FIG. 65(B), for example, it is done by changing the color according to the magnitude of the product of multiplication as follows: red (product value 2000), orange (product value 1500), yellow (product value 1000), green (product value 0.0), light blue (product value −1000), blue (product value −2000).

The images in FIG. 65 are examples of hybrid imaging in which functions at different sites of a living body are visualized simultaneously.

FIG. 66(A) is a color-coded view representing time series changes in the products of multiplying L, and (B) is a color-coded view representing of time series changes in the hybrid angle (H angle), which are obtained from the muscle (biceps of the arm) and the left brain primary motor area and its surrounding area (Channels 6-12 [Ch6-Ch12]), upon performance of a task of lifting a 14.5 kg dumbbell.

Figure 66:
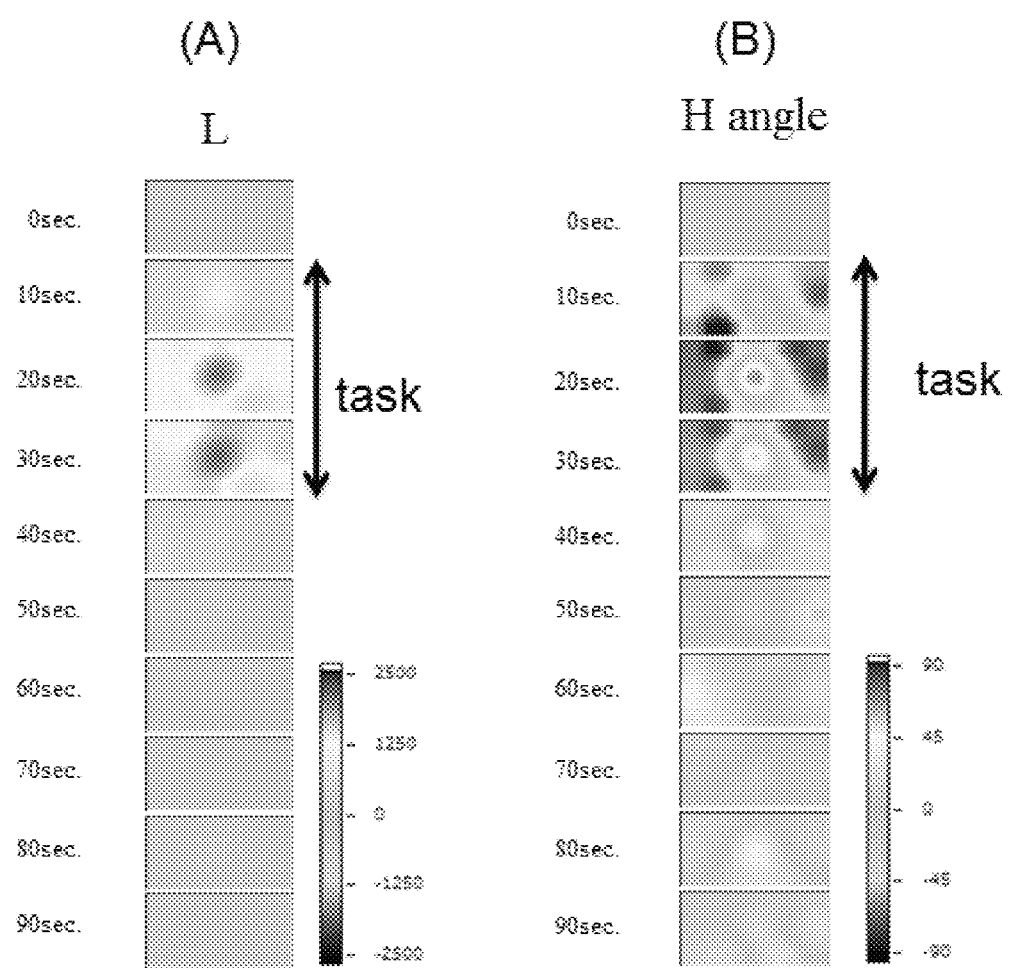
FIG. 66(A) is a color-coded view representing time series changes in the products of multiplying L, and (B) is a color-coded view representing of time series changes in the hybrid angle (H angle), which are obtained from the muscle (biceps of the arm) and the left brain primary motor area and its surrounding area (Channels 6-12 [Ch6-Ch12]), upon performance of a task of lifting a 14.5 kg dumbbell.

In FIG. 66, an arrangement of 7 channels is visualized in each frame.

Color-coding in FIG. 66(A) is done, for example, by changing the color according to the magnitude of the product of multiplication as follows: red (product value 2500), orange (product value 1750), yellow (product value 1250), green (product value 0.0), light blue (product value −1250), blue (product value −2500).

In FIG. 66(B), for example, it is done by changing the color according to the size of ∠H angle: red (90 degrees), orange (65 degrees), yellow (45 degrees), green (0.0 degrees), light blue (−45 degrees), blue (−90 degrees).

The images of FIG. 66 are examples of hybrid imaging, in which functions of different sites of a living body are visualized simultaneously.

As shown in FIG. 66(A), the sites where the values for L are high coincide with the primary motor area (M1), and the values increase gradually as the exercise continues. At completion of the exercise, they flatten at once, showing that the brain and muscle are active simultaneously, and the strength of that activity. The image at 30 s shows the peak of activity.

As shown in FIG. 66(B), the hybrid angle (H angle) makes evaluation possible by selecting out the time when the brain and the muscle are consuming oxygen and working most efficiently.

In this case, it can be seen to be 20 s after the start of exercise. Namely, the angle H is an excellent index for quantitatively evaluating and measuring oxygen exchange efficiency when different sites or different organs are working together.

[Program]

Program 12 of the embodiment of the present invention shown in FIG. 1 is wherein it implements the processing described above by the controller 7 of said apparatus K for evaluating biological function.

This Program 12 may also be recorded on a recording media such as a magnetic disk, CD-ROM, semiconductor memory, or the like, and it may also be downloaded over a communications network.

The present invention is not limited to the embodiment described above, and various modifications are possible within the scope of the technical particulars as claimed in the Claims.

For example, the types of physiological indices (amounts of change, parameters), the degree of adjustment of physiological indices by means of adjusting part 11, the combinations of physiological indices to be compared and adjusted, the combinations for correlation coefficients between physiological indices and multiplication of physiological indices, etc., as claimed in the Specification and the Drawings, are illustrative examples, and the present invention is not limited to these.

In addition, a "plurality of sites with different biological functions" refers to sites where the biological function differs to an extent that requires adjustment of their physiological indices by means of adjusting part 11; they are not only the muscle and the brain, but also include different sites in the brain and different muscle sites (for example, arm and leg), etc.

Furthermore, physiological indices for 3 or more sites may also be calculated, adjusted, and displayed on display part 9 by 3-dimensional volumetric images.

INDUSTRIAL APPLICABILITY

The apparatus and program for evaluating biological function of the present invention can be used for simultaneously measuring, evaluating, imaging and displaying the biological function of a plurality of sites with different biological functions, such as the brain and the muscle, different parts of the brain, different muscle locations, and the like.

EXPLANATION OF REFERENCE NUMERALS

K: apparatus for evaluating biological function
1: Living body probe
2: Apparatus body
3: Light intensity adjustor
4: Selector-adjustor
6: A/D converter
7: Controller
8: Memory part
9: Display part
10: Calculating part
11: Adjusting part
12: Program

I claim:

1. An apparatus for evaluating biological function having a plurality of living body probes for irradiating light to and receiving emitted light from a brain site and a muscle site with different biological functions of a living body, and an apparatus body for entering light information detected by means of said plurality of living body probes and performing calculation, control and memory operations, and utilizing a near-infrared spectroscopy method, wherein said apparatus body comprises:

a calculating part for calculating a change in oxyhemoglobin concentration, a change in deoxyhemoglobin concentration, and physiological indices including a variety of parameters derived from the relationships between the change in oxyhemoglobin concentration and the change in deoxyhemoglobin concentration, based on light information from said plurality of living body probes;

an adjusting part for adjusting a display form of the physiological indices calculated by means of said calculating part and corresponding to said brain site and said muscle site in such a way that they can be compared as different axes of a graph respectively, wherein the adjusting part adjusts the unit or interval of the scale of the axes at least; and a display part for displaying images based on the information of the physiological indices adjusted by means of said adjusting part.

2. The apparatus for evaluating biological function as claimed in claim 1, wherein said adjusting part adjusts the same physiological indices at the brain site and the muscle site in such a way that they can be compared.

3. The apparatus for evaluating biological function as claimed in claim 1, wherein said adjusting part adjusts different physiological indices at the brain site and the muscle site in such a way that they can be compared.

4. The apparatus for evaluating biological function as claimed in claim 1, wherein said calculating part calculates correlation coefficients of said physiological indices at the brain site and the muscle site, and said display part displays correlation information concerning said correlation coefficients.

5. The apparatus for evaluating biological function as claimed in claim 1, wherein said calculating part multiplies together the same physiological indices at the brain site and the muscle site, and said display part displays product information concerning products of said multiplication.

6. The apparatus for evaluating biological function as claimed in claim 1, wherein said calculating part multiplies together different physiological indices at the brain site and the muscle site, and said display part displays product information concerning products of said multiplication.

7. The apparatus for evaluating biological function as claimed in claim 1, wherein said muscle site includes at least two different muscle sites.

8. The apparatus for evaluating biological function as claimed in claim 1, wherein said brain site includes at least two different brain sites.

9. The apparatus for evaluating biological function as claimed in claim 1, wherein said calculating part calculates change in blood volume concentration ($\Delta BV$) at a region of interest (ROI) by Equation 1:

$$\Delta BV = \Delta[Hb] + \Delta[HbO_2] \qquad \text{(Equation 1)}$$

wherein $\Delta[Hb]$ is change in deoxyhemoglobin concentration, and $\Delta[HbO_2]$ is change in oxyhemoglobin concentration.

10. The apparatus for evaluating biological function as claimed in claim 9, wherein said calculating part calculates a time of maximum muscle blood volume and a time of maximum cerebral blood volume at a desired region of interest (ROI) from a two-dimensional vector diagram showing a relationship between changes in blood volume concentration ($\Delta BV$) at the brain site and the muscle site.

11. The apparatus for evaluating biological function as claimed in claim 1, wherein said calculating part calculates change in oxygen exchange concentration ($\Delta OE$) at a region of interest (ROI) by Equation 2:

$$\Delta OE = \Delta[Hb] - \Delta[HbO_2] \qquad \text{(Equation 2)}$$

wherein $\Delta[Hb]$ is change in deoxyhemoglobin concentration, and $\Delta[HbO_2]$ is change in oxyhemoglobin concentration.

12. The apparatus for evaluating biological function as claimed in claim 11, wherein said calculating part calculates a time of maximum muscle oxygen exchange and a time of maximum cerebral oxygen exchange at a desired region of interest (ROI) from a two-dimensional vector diagram showing a relationship between changes in oxygen exchange concentration (ΔOE) at the brain site and the muscle site.

13. The apparatus for evaluating biological function as claimed in claim 1, wherein said calculating part calculates a ratio e, which is a ratio between change in oxygen exchange concentration (ΔOE) and change in blood volume concentration (ΔBV) at a region of interest (ROI) by Equation 3:

$$e=\Delta OE/\Delta BV=(\Delta[Hb]-\Delta[HbO_2])/(\Delta[Hb]+\Delta[HbO_2]) \quad \text{(Equation 3)}$$

where Δ[Hb] is change in deoxyhemoglobin concentration, and Δ[HbO$_2$] is change in oxyhemoglobin concentration.

14. The apparatus for evaluating biological function as claimed in claim 13, wherein said calculating part calculates an angle E by Equation 3a:

$$E=\arctan(e) \quad \text{(Equation 3a)}$$

15. The apparatus for evaluating biological function as claimed in claim 14, wherein said calculating part calculates a hybrid angle E (EH), which is an angle formed on a two-dimensional diagram, obtained by taking a first angle E of one of two different sites of said living body as a vertical axis and a second angle E of the other site as a horizontal axis and plotting them over time, between a first angle E [E$_1$] and a second angle E [E$_2$], by Equation 3b:

$$EH=\arctan(\angle E_1/\angle E_2) \quad \text{(Equation 3b)}$$

16. The apparatus for evaluating biological function as claimed in claim 1, wherein said calculating part multiplies the same physiological index at two different sites and calculates a first hybrid angle (H$_1$), which is an angle formed on a two-dimensional diagram, obtained by taking a first multiplied value of one of the two different sites of said living body as the vertical axis and a second multiplied value from the other site as a horizontal axis and plotting them over time, between the first multiplied value and the second multiplied value, by Equation 3c:

$$H_1=\arctan \text{ the first(multiplied value}_1\text{/the second multiplied value}_2) \quad \text{(Equation 3c)}$$

17. The apparatus for evaluating biological function as claimed in claim 1, wherein said calculating part multiplies different physiological indices at two different sites and calculates a second hybrid angle (H$_2$), which is an angle formed on a two-dimensional diagram, obtained by taking a third multiplied value of one of the two different sites of said living body as a vertical axis and a fourth multiplied value from the other site as a horizontal axis and plotting them over time, between the third multiplied value and the fourth multiplied value, by Equation 3d:

$$\text{second hybrid angle } H_2=\arctan(\text{the third multiplied value}_3\text{/the fourth multiplied value}_4) \quad \text{(Equation 3d)}$$

18. The apparatus for evaluating biological function as claimed in claim 1, wherein said calculating part calculates a brain/muscle oxygen load ratio (M/B(1)) and a scalar PL$_1$ (power) during exercise at a plurality of regions of interest (ROIs) of the brain site and the muscle site, from on a two-dimensional diagram and by Equation 4:

$$M/B(1)=[\text{change in muscle oxygen exchange MOE}]/[\text{change in cerebral oxygen exchange COE}] \quad \text{(Equation 4)}$$

19. The apparatus for evaluating biological function as claimed in claim 1, wherein said calculating part calculates a brain/muscle blood volume load ratio (M/B(2)) and a scalar PL$_2$ (power) during exercise at a plurality of regions of interest (ROIs) of the brain site and the muscle site, from on a two-dimensional diagram and by Equation 5:

$$M/B(2)=[\text{change in muscle blood volume MBV}]/[\text{change in cerebral blood volume CBV}] \quad \text{(Equation 5)}$$

20. The apparatus for evaluating biological function as claimed in claim 1, wherein said calculating part calculates degree of oxygen saturation Y from a two-dimensional diagram, in which the horizontal axis is an amount of oxyhemoglobin (O) in a region of interest (ROI) and a vertical axis is an amount of deoxyhemoglobin (D) in the ROI, as a slope Y angle on an O/D plane, by Equation 6:

$$\text{Degree of oxygen saturation } Y=1/(1+\tan Y \text{ angle}) \quad \text{(Equation 6)}$$

21. The apparatus for evaluating biological function as claimed in claim 1, wherein said calculating part calculates a ratio E (ratio of oxygen exchange to blood volume), which is defined as a proportion of oxygen exchange (D−O) to total hemoglobin (D+O) at a measurement starting point E$_0$, from a two-dimensional diagram in which a horizontal axis is an amount of oxyhemoglobin (O) in a region of interest (ROI) and a vertical axis is an amount of deoxyhemoglobin (D) in the ROI, by Equation 7:

$$E=(D-O)/(D+O) \quad \text{(Equation 7)}$$

22. The apparatus for evaluating biological function as claimed in claim 1, wherein said calculating part calculates change in the degree of oxygen saturation Y (ΔY), from a graph showing a relationship of change in degree of oxygen saturation Y to changes in oxyhemoglobin (ΔO) and changes in deoxyhemoglobin (D), in which a horizontal axis is an amount of oxyhemoglobin (O) in a region of interest (ROI) and a vertical axis is an amount of deoxyhemoglobin (D) in the ROI, by Equation 8:

$$\text{Change in oxygen saturation } \Delta Y=1/(1+\sin^2 \Delta Y \text{ angle}) \quad \text{(Equation 8)}$$

23. The apparatus for evaluating biological function as claimed in claim 1, wherein said calculating part calculates an arbitrary hypothetical maximum change in the hematocrit (ΔHt$_{max}$) with respect to a maximum change in blood volume (ΔBVmax) which is an actual measured value at a region on interest (ROI), by substituting the blood volume at an start of measurement (BV$_0$) at the ROI into Equation 9:

$$\Delta Ht_{max}=[(\Delta O+\Delta D)_{max}/(O+D)]=\Delta BV_{max}/BV_0 \quad \text{(Equation 9)}$$

24. The apparatus for evaluating biological function as claimed in claim 23, wherein said ΔBV$_{max}$ is selected as the maximum change from within a plurality of ROIs.

25. The apparatus for evaluating biological function as claimed in claim 23, wherein an estimated hematocrit value is set for a desired ROI.

26. The apparatus for evaluating biological function as claimed in claim 1, wherein said calculating part calculates an estimated change in degree of oxygen saturation ΔY at a region of interest (ROI) by substituting the blood volume at a start of measurement (BV$_0$) at the ROI into Equation 10 or Equation 11, and said adjusting part adjusts the graphs showing time series changes in ΔY at the brain site and the muscle site in such a way that they can be displayed by means of said display part, $$\Delta Y = (-1/2)[\Delta OE/(BV_0 + \Delta BV)] + \quad \text{(Equation 10)}$$
$$(E_0/2)[\Delta BV/(BV_0 + \Delta BV)]$$
$$\approx (-1/2)[\Delta OE/(BV_0 + \Delta BV)] \quad \text{(Equation 11)}$$

wherein ΔOE is change in oxygen exchange concentration, $BV_0$ is blood volume at the start of measurement, ΔBV is change in blood volume concentration, and $E_0$ is a ratio E (ratio of oxygen exchange to blood volume), which is defined as a ratio of oxygen exchange (Δ[Hb]−Δ[HbO$_2$]) to total hemoglobin (Δ[Hb]+Δ[HbO$_2$]), at the start of measurement.

27. The apparatus for evaluating biological function as claimed in claim 26, wherein said adjusting part adjusts graphs showing time series changes in ΔY at the brain site and the muscle site in such a way that they can be displayed by means of said display part.

28. The apparatus for evaluating biological function as claimed in claim 1, wherein said calculating part calculates ΔL, which is defined by Equation 12, and said adjusting part adjusts said physiological indices from the brain site and the muscle site in such a way that they can be compared and displayed on unit circles of the same size, based on a maximum measured value of ΔL:

$$(\Delta L)^2 = (\Delta[Hb])^2 + (\Delta[HbO_2])^2 \qquad \text{(Equation 12).}$$

29. The apparatus for evaluating biological function as claimed in claim 1, wherein said adjusting part adjusts graphs showing changes in products of multiplication of said physiological indices of the brain site and the muscle site in such a way that they can be displayed on said display part.

30. The apparatus for evaluating biological function as claimed in claim 1, wherein said display part displays graphs showing time series changes, in which a vertical axis is said physiological indices and a horizontal axis is time.

31. The apparatus for evaluating biological function as claimed in claim 1, wherein said display part displays two-dimensional diagrams obtained by taking one of said two different physiological indices as a vertical axis and the other as a horizontal axis and plotting them over time.

32. The apparatus for evaluating biological function as claimed in claim 1, wherein said display part displays images that are color-coded according to a size of values of said physiological indices.

33. The apparatus for evaluating biological function as claimed in claim 1, wherein said display part displays changes in said physiological indices at rest, when there is a task load on said living body, and during recovery, on the same graph.

34. The apparatus for evaluating biological function as claimed in claim 1, wherein said display part displays changes in said physiological indices at rest, when there is a task load on said living body, and during recovery, as a dynamic state as a wave motion and rotational motion of hemoglobin-related parameters on a vector space, and displays the direction and strength of those changes on different graphs and/or image displays.

35. A computer-readable storage device comprising executable instructions that, in response to execution, cause a system comprising a processor to perform operations, comprising:

calculating a change in oxyhemoglobin concentration, a change in deoxyhemoglobin concentration, and physiological indices including a variety of parameters derived from the relationships between the change in oxyhemoglobin concentration and the change in deoxyhemoglobin concentration, based on light information from a plurality of living body probes;

adjusting a display form of the physiological indices calculated by means of said calculating and corresponding to said brain site and said muscle site in such a way that they can be compared as different axes of a graph respectively, wherein the adjusting adjusts the unit or interval of the scale of the axes at least; and displaying images based on the information of the physiological indices adjusted by means of said adjusting.

* * * * *